United States Patent
Cao et al.

(10) Patent No.: US 11,944,645 B2
(45) Date of Patent: Apr. 2, 2024

(54) MODIFIED CELL AND USE THEREOF IN GENE AND CELL THERAPY

(71) Applicants: Innovative Cellular Therapeutics Holdings, Ltd., Grand Cayman (KY); Innovative Cellular Therapeutics, Inc., Rockville, MD (US)

(72) Inventors: Zhiyuan Cao, Shanghai (CN); Lei Xiao, Rockville, MD (US); Yuzhe Peng, Shanghai (CN); Wei Ding, Shanghai (CN); Wensheng Wang, Shanghai (CN)

(73) Assignees: Innovative Cellular Therapeutics Holdings, Ltd., George Town (KY); Innovative Cellular Therapeutics, Inc., Rockville, MD (US)

( * ) Notice: Subject to any disclaimer, the term of this patent is extended or adjusted under 35 U.S.C. 154(b) by 258 days.

(21) Appl. No.: 17/490,582

(22) Filed: Sep. 30, 2021

(65) Prior Publication Data
US 2022/0105134 A1    Apr. 7, 2022

Related U.S. Application Data

(60) Provisional application No. 63/086,343, filed on Oct. 1, 2020.

(51) Int. Cl.
*A61K 35/17* (2015.01)
*C07K 14/47* (2006.01)
*C07K 14/725* (2006.01)

(52) U.S. Cl.
CPC .......... *A61K 35/17* (2013.01); *C07K 14/4702* (2013.01); *C07K 14/7051* (2013.01)

(58) Field of Classification Search
CPC ............ A61K 35/17; A61K 2039/5156; A61K 39/0011; A61K 39/001112; C07K 14/4702; C07K 14/7051; C07K 2319/03; A61P 35/00
See application file for complete search history.

(56) References Cited

PUBLICATIONS

Somerville et al. ZBED2 is an antagonist of interferon regulatory factor 1 and modifies cell identity in pancreatic cancer. 2020. PNAS, vol. 117; No. 21: pp. 11470-11482 (Year: 2020).*
An et al. Cavin3 Suppresses Breast Cancer Metastasis via Inhibiting AKT Pathway. 2020. Front. Pharmacol. vol. 11: 01228. (Year: 2020).*
Li et al. Dysfunctional CD8 T Cells Form a Proliferative, Dynamically Regulated Compartment within Human Melanoma. 2019. Cell vol. 176, pp. 775-789. (Year: 2019).*
Chow et al. Clinical implications of T cell exhaustion for cancer immunotherapy. 2022. Nature Reviews, vol. 19, pp. 775-790. (Year: 2022).*
Chen et al. CAR-T: What Is Next? 2023. Cancers vol. 15, No. 663, pp. 1-20. (Year: 2023).*

* cited by examiner

*Primary Examiner* — Benjamin P Blumel
*Assistant Examiner* — Amber K Faust
(74) *Attorney, Agent, or Firm* — Lee & Hayes P.C.

(57) ABSTRACT

The present disclosure describes compositions and methods for treating cancer. Embodiments relate to a cell modified to express one or more molecules at a level that is higher or lower than the level of the one or more molecules expressed by a cell that has not been modified to express the one or more molecules, wherein the one or more molecules comprise Cavin3, ZBED2, and MYC.

20 Claims, 43 Drawing Sheets
Specification includes a Sequence Listing.

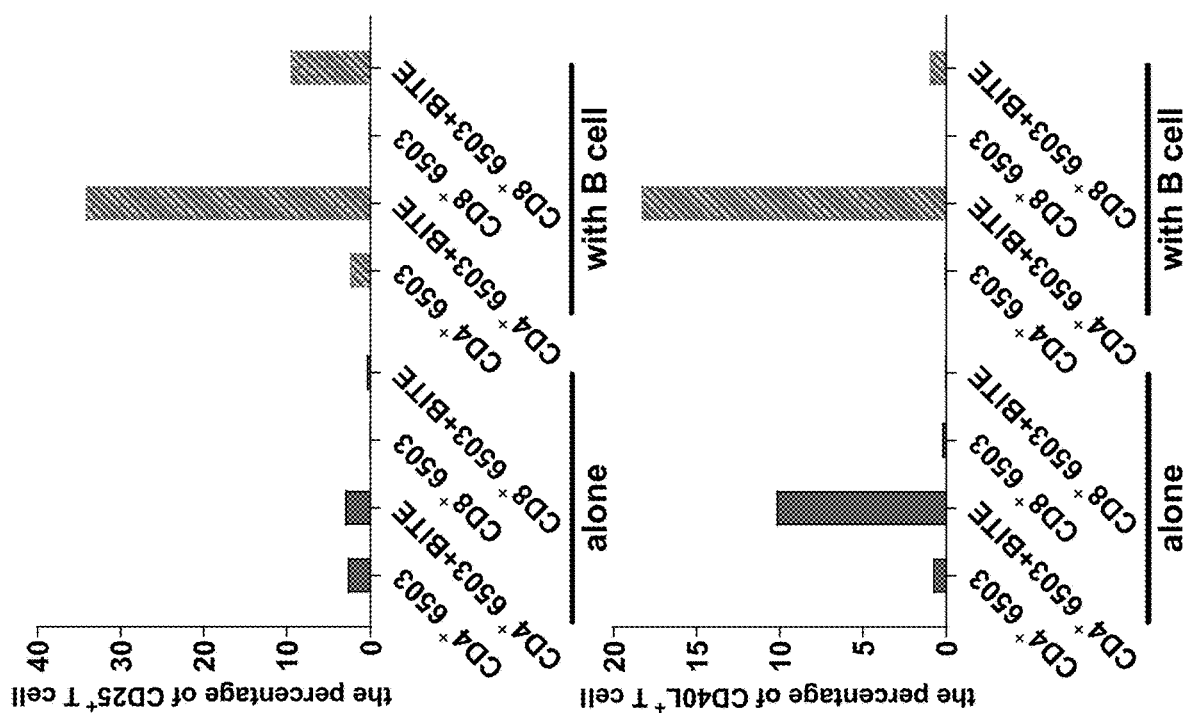
FIG. 13B
FIG. 13D
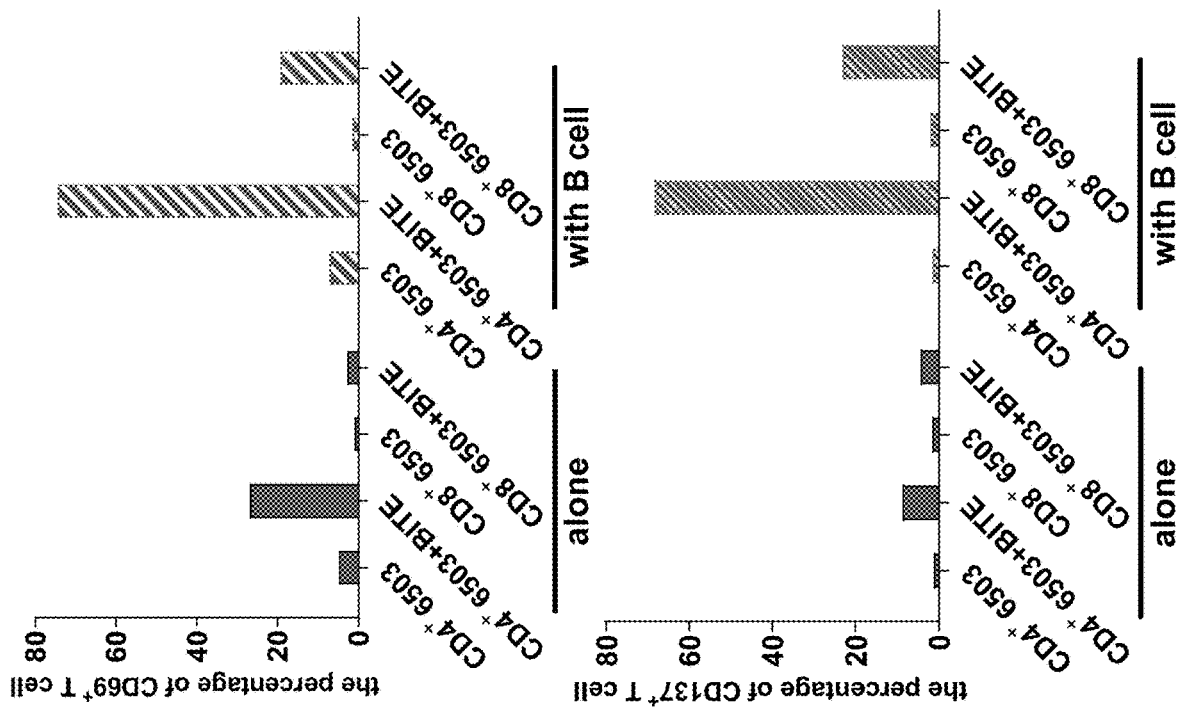
FIG. 13A
FIG. 13C

| Gene | Pvalue | Mean(C1) | std(C1) | Mean(others) | std(others) | lgF2C |
|---|---|---|---|---|---|---|
| IL2 | 1.95E-15 | 0.16 | 0.462 | 0.044 | 0.239 | 1.856 |
| CCR4 | 6.59E-115 | 1.064 | 0.986 | 0.296 | 0.513 | 1.846 |
| CCR4 | 6.59E-115 | 1.064 | 0.986 | 0.296 | 0.513 | 1.846 |
| IL18R1 | 3.14E-60 | 0.605 | 0.789 | 0.184 | 0.406 | 1.72 |
| IL3 | 2.29E-74 | 0.973 | 1.058 | 0.321 | 0.677 | 1.6 |
| CCR8 | 2.90E-49 | 0.573 | 0.783 | 0.199 | 0.408 | 1.526 |
| CCR8 | 2.90E-49 | 0.573 | 0.783 | 0.199 | 0.408 | 1.526 |
| IL1RAP | 2.53E-30 | 0.351 | 0.609 | 0.128 | 0.326 | 1.458 |
| CCR1 | 6.77E-11 | 0.152 | 0.451 | 0.059 | 0.243 | 1.368 |
| CCR1 | 6.77E-11 | 0.152 | 0.451 | 0.059 | 0.243 | 1.368 |
| CXCL9 | 8.50E-10 | 0.159 | 0.497 | 0.062 | 0.302 | 1.366 |
| CXCL9 | 8.50E-10 | 0.159 | 0.497 | 0.062 | 0.302 | 1.366 |
| CXCR6 | 2.95E-21 | 0.386 | 0.78 | 0.151 | 0.421 | 1.353 |
| CXCR6 | 2.95E-21 | 0.386 | 0.78 | 0.151 | 0.421 | 1.353 |
| CCL17 | 3.26E-14 | 0.214 | 0.533 | 0.084 | 0.319 | 1.343 |
| CCL17 | 3.26E-14 | 0.214 | 0.533 | 0.084 | 0.319 | 1.343 |
| CCL22 | 3.80E-31 | 0.49 | 0.774 | 0.198 | 0.478 | 1.31 |
| CCL22 | 3.80E-31 | 0.49 | 0.774 | 0.198 | 0.478 | 1.31 |
| CCL1 | 7.14E-87 | 1.309 | 1.125 | 0.533 | 0.846 | 1.296 |
| CCL1 | 7.14E-87 | 1.309 | 1.125 | 0.533 | 0.846 | 1.296 |
| CCR2 | 1.45E-14 | 0.251 | 0.588 | 0.107 | 0.331 | 1.227 |
| CCR2 | 1.45E-14 | 0.251 | 0.588 | 0.107 | 0.331 | 1.227 |
| TNFRSF9 | 1.24E-17 | 0.288 | 0.592 | 0.126 | 0.353 | 1.196 |
| IL6ST | 1.22E-41 | 0.625 | 0.784 | 0.276 | 0.49 | 1.178 |
| FASLG | 3.07E-10 | 0.156 | 0.435 | 0.069 | 0.244 | 1.172 |
| XCL2 | 2.81E-29 | 0.538 | 0.807 | 0.24 | 0.544 | 1.167 |
| XCL2 | 2.81E-29 | 0.538 | 0.807 | 0.24 | 0.544 | 1.167 |
| BMPR1A | 5.78E-07 | 0.103 | 0.356 | 0.047 | 0.195 | 1.126 |
| CD40 | 4.54E-06 | 0.102 | 0.369 | 0.047 | 0.235 | 1.107 |
| CSF2 | 6.33E-92 | 1.694 | 1.224 | 0.806 | 1.018 | 1.071 |
| CSF1 | 2.66E-20 | 0.435 | 0.741 | 0.213 | 0.473 | 1.03 |
| TGFBR2 | 1.19E-41 | 0.722 | 0.8 | 0.365 | 0.515 | 0.985 |
| IL13 | 3.48E-41 | 1.288 | 1.401 | 0.653 | 1.034 | 0.981 |
| XCL1 | 4.82E-58 | 1.378 | 1.21 | 0.703 | 0.98 | 0.971 |
| XCL1 | 4.82E-58 | 1.378 | 1.21 | 0.703 | 0.98 | 0.971 |
| IL17RB | 9.01E-06 | 0.158 | 0.544 | 0.082 | 0.326 | 0.958 |
| CCL3 | 1.31E-64 | 1.294 | 1.054 | 0.674 | 0.827 | 0.941 |
| CCL3 | 1.31E-64 | 1.294 | 1.054 | 0.674 | 0.827 | 0.941 |

FIG 23

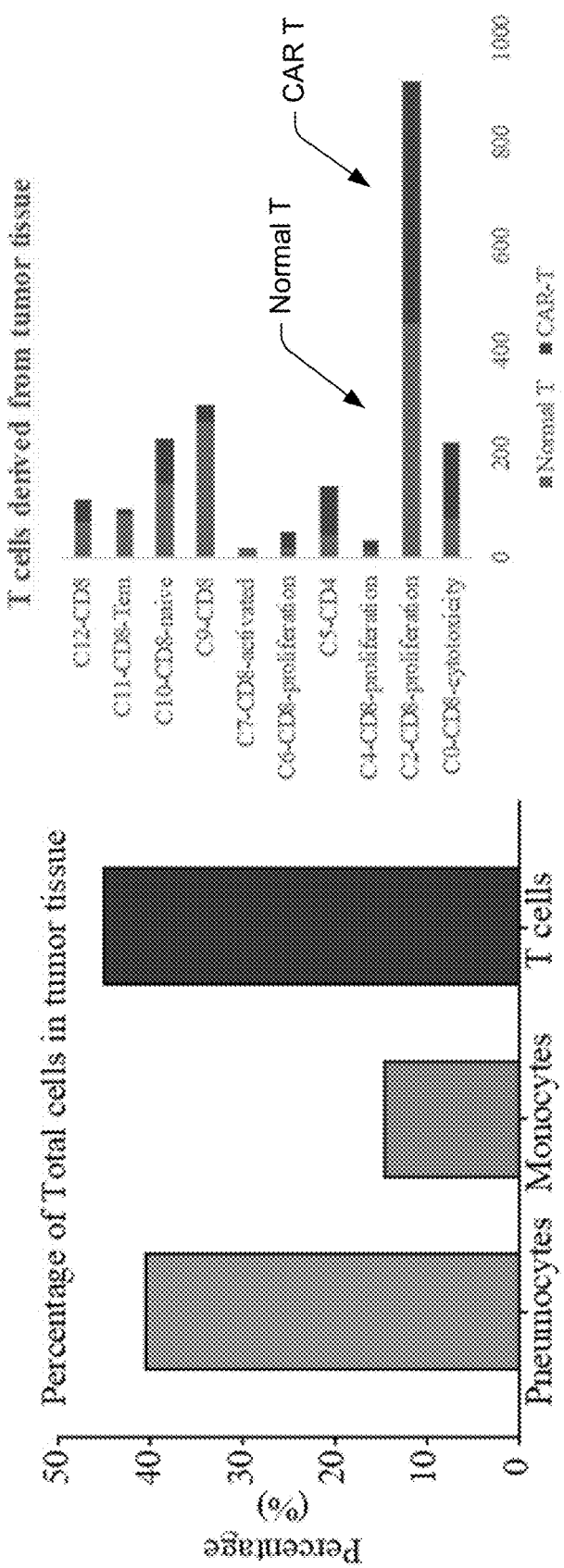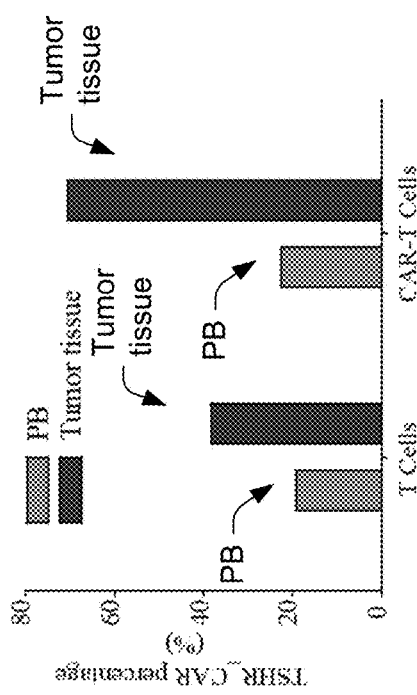
FIG. 26A
FIG. 26B
FIG. 26C

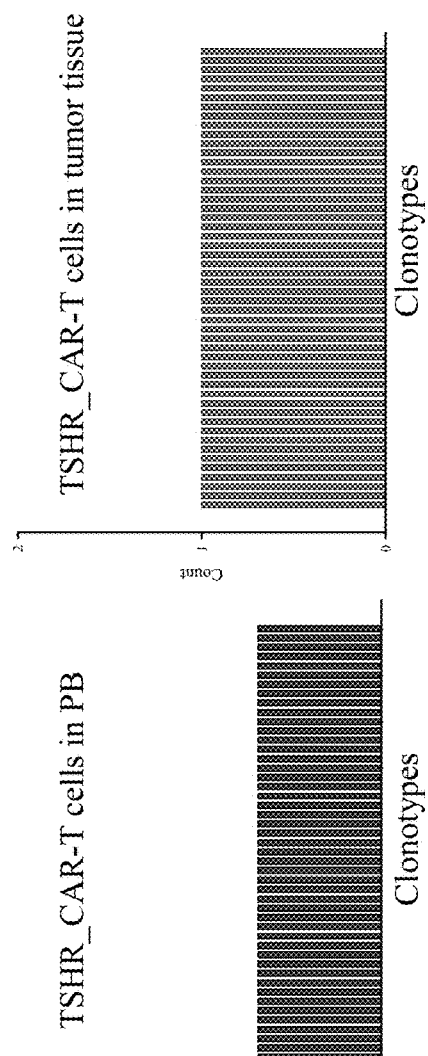
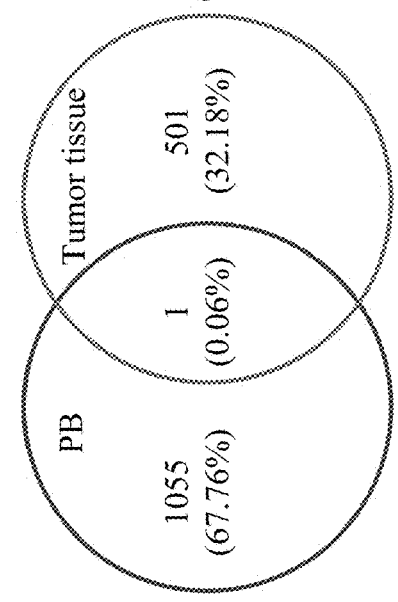
FIG. 27A
FIG. 27B
FIG. 27C
| Clonotype | PB | Tumor tissue | TRA_cdr3 | TRB_cdr3 |
|---|---|---|---|---|
| 1 | TSHR_CAR | TSHR_CAR | CAVRSGGYQKVTF | CASSSGQGVTYEQYF |
FIG. 27D

SEQUENCE LISTING

```
<160> NUMBER OF SEQ ID NOS: 55

<210> SEQ ID NO 1
<211> LENGTH: 21
<212> TYPE: PRT
<213> ORGANISM: Homo sapiens

<400> SEQUENCE: 1

Ile Thr Leu Gly Leu Leu Val Ala Gly Val Leu Val Leu Leu Val Ser
1               5                   10                  15

Leu Gly Val Ala Ile
            20

<210> SEQ ID NO 2
<211> LENGTH: 21
```

```
<212> TYPE: PRT
<213> ORGANISM: Homo sapiens

<400> SEQUENCE: 2

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 3
<211> LENGTH: 22
<212> TYPE: PRT
<213> ORGANISM: Homo sapiens

<400> SEQUENCE: 3

Ala Leu Val Val Ile Pro Ile Ile Phe Gly Ile Leu Phe Ala Ile Leu
1               5                   10                  15

Leu Val Leu Val Phe Ile
            20

<210> SEQ ID NO 4
<211> LENGTH: 22
<212> TYPE: PRT
<213> ORGANISM: Homo sapiens

<400> SEQUENCE: 4

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 5
<211> LENGTH: 30
<212> TYPE: PRT
<213> ORGANISM: Homo sapiens

<400> SEQUENCE: 5

Ala Gly Leu Ala Ala Gly Thr Val Ala Ser Ile Ile Leu Ala Leu Val
1               5                   10                  15

Leu Leu Val Val Leu Val Val Cys Gly Pro Leu Ala Tyr
            20                  25                  30

<210> SEQ ID NO 6
<211> LENGTH: 21
<212> TYPE: PRT
<213> ORGANISM: Homo sapiens

<400> SEQUENCE: 6

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 7
<211> LENGTH: 19
<212> TYPE: PRT
<213> ORGANISM: Homo sapiens

<400> SEQUENCE: 7

Val Ala Val Gly Leu Gly Ser Cys Leu Ala Ile Leu Ile Leu Ala Ile
1               5                   10                  15

Cys Gly Leu
```

<210> SEQ ID NO 8
<211> LENGTH: 27
<212> TYPE: PRT
<213> ORGANISM: Homo sapiens

<400> SEQUENCE: 8

Phe Trp Ala Leu Val Val Ala Gly Val Leu Phe Cys Tyr Gly Leu
1               5                   10                  15

Leu Val Thr Val Ala Leu Cys Val Ile Trp Thr
            20                  25

<210> SEQ ID NO 9
<211> LENGTH: 23
<212> TYPE: PRT
<213> ORGANISM: Homo sapiens

<400> SEQUENCE: 9

Gly Ala Ile Gly Gly Ala Gly Val Thr Ala Leu Leu Ala Leu Cys Leu
1               5                   10                  15

Cys Leu Ile Phe Phe Ile Val
            20

<210> SEQ ID NO 10
<211> LENGTH: 21
<212> TYPE: PRT
<213> ORGANISM: Homo sapiens

<400> SEQUENCE: 10

Val Leu Phe Tyr Leu Ala Val Gly Ile Met Phe Leu Val Asn Thr Val
1               5                   10                  15

Leu Trp Val Thr Ile
            20

<210> SEQ ID NO 11
<211> LENGTH: 21
<212> TYPE: PRT
<213> ORGANISM: Homo sapiens

<400> SEQUENCE: 11

Leu Leu Pro Ser Trp Ala Ile Thr Leu Ile Ser Val Asn Gly Ile Phe
1               5                   10                  15

Val Ile Cys Cys Leu
            20

<210> SEQ ID NO 12
<211> LENGTH: 21
<212> TYPE: PRT
<213> ORGANISM: Homo sapiens

<400> SEQUENCE: 12

Trp Ile Thr Ala Val Leu Pro Thr Val Ile Ile Cys Val Met Val Phe
1               5                   10                  15

Cys Leu Ile Leu Trp
            20

<210> SEQ ID NO 13
<211> LENGTH: 21
<212> TYPE: PRT
<213> ORGANISM: Homo sapiens

<400> SEQUENCE: 13

```
Val Ala Ala Ile Leu Gly Leu Gly Leu Val Leu Gly Leu Leu Gly Pro
1               5                   10                  15

Leu Ala Ile Leu Leu
            20

<210> SEQ ID NO 14
<211> LENGTH: 27
<212> TYPE: PRT
<213> ORGANISM: Homo sapiens

<400> SEQUENCE: 14

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 15
<211> LENGTH: 24
<212> TYPE: PRT
<213> ORGANISM: Homo sapiens

<400> SEQUENCE: 15

Ile Phe Met Tyr Leu Leu Thr Val Phe Leu Ile Thr Gln Met Ile Gly
1               5                   10                  15

Ser Ala Leu Phe Ala Val Tyr Leu
            20

<210> SEQ ID NO 16
<211> LENGTH: 185
<212> TYPE: PRT
<213> ORGANISM: Homo sapiens

<400> SEQUENCE: 16

Ser Tyr Leu Asp Leu Pro Trp Tyr Leu Arg Met Val Cys Gln Trp Thr
1               5                   10                  15

Gln Thr Arg Arg Arg Ala Arg Asn Ile Pro Leu Glu Glu Leu Gln Arg
            20                  25                  30

Asn Leu Gln Phe His Ala Phe Ile Ser Tyr Ser Gly His Asp Ser Phe
        35                  40                  45

Trp Val Lys Asn Glu Leu Leu Pro Asn Leu Glu Lys Glu Gly Met Gln
    50                  55                  60

Ile Cys Leu His Glu Arg Asn Phe Val Pro Gly Lys Ser Ile Val Glu
65                  70                  75                  80

Asn Ile Ile Thr Cys Ile Glu Lys Ser Tyr Lys Ser Ile Phe Val Leu
                85                  90                  95

Ser Pro Asn Phe Val Gln Ser Glu Trp Cys His Tyr Glu Leu Tyr Phe
            100                 105                 110

Ala His His Asn Leu Phe His Glu Gly Ser Asn Ser Leu Ile Leu Ile
        115                 120                 125

Leu Leu Glu Pro Ile Pro Gln Tyr Ser Ile Pro Ser Ser Tyr His Lys
    130                 135                 140

Leu Lys Ser Leu Met Ala Arg Arg Thr Tyr Leu Glu Trp Pro Lys Glu
145                 150                 155                 160

Lys Ser Lys Arg Gly Leu Phe Trp Ala Asn Leu Arg Ala Ala Ile Asn
                165                 170                 175

Ile Lys Leu Thr Glu Gln Ala Lys Lys
            180                 185
```

```
<210> SEQ ID NO 17
<211> LENGTH: 175
<212> TYPE: PRT
<213> ORGANISM: Homo sapiens

<400> SEQUENCE: 17

His Arg Phe His Gly Leu Trp Tyr Met Lys Met Met Trp Ala Trp Leu
1               5                   10                  15

Gln Ala Lys Arg Lys Pro Arg Lys Ala Pro Ser Arg Asn Ile Cys Tyr
            20                  25                  30

Asp Ala Phe Val Ser Tyr Ser Glu Arg Asp Ala Tyr Trp Val Glu Asn
        35                  40                  45

Leu Met Val Gln Glu Leu Glu Asn Phe Asn Pro Pro Phe Lys Leu Cys
    50                  55                  60

Leu His Lys Arg Asp Phe Ile Pro Gly Lys Trp Ile Ile Asp Asn Ile
65                  70                  75                  80

Ile Asp Ser Ile Glu Lys Ser His Lys Thr Val Phe Val Leu Ser Glu
                85                  90                  95

Asn Phe Val Lys Ser Glu Trp Cys Lys Tyr Glu Leu Asp Phe Ser His
            100                 105                 110

Phe Arg Leu Phe Asp Glu Asn Asn Asp Ala Ala Ile Leu Ile Leu Leu
        115                 120                 125

Glu Pro Ile Glu Lys Lys Ala Ile Pro Gln Arg Phe Cys Lys Leu Arg
    130                 135                 140

Lys Ile Met Asn Thr Lys Thr Tyr Leu Glu Trp Pro Met Asp Glu Ala
145                 150                 155                 160

Gln Arg Glu Gly Phe Trp Val Asn Leu Arg Ala Ala Ile Lys Ser
                165                 170                 175

<210> SEQ ID NO 18
<211> LENGTH: 179
<212> TYPE: PRT
<213> ORGANISM: Homo sapiens

<400> SEQUENCE: 18

Glu Gly Trp Arg Ile Ser Phe Tyr Trp Asn Val Ser Val His Arg Val
1               5                   10                  15

Leu Gly Phe Lys Glu Ile Asp Arg Gln Thr Glu Gln Phe Glu Tyr Ala
            20                  25                  30

Ala Tyr Ile Ile His Ala Tyr Lys Asp Lys Asp Trp Val Trp Glu His
        35                  40                  45

Phe Ser Ser Met Glu Lys Glu Asp Gln Ser Leu Lys Phe Cys Leu Glu
    50                  55                  60

Glu Arg Asp Phe Glu Ala Gly Val Phe Glu Leu Glu Ala Ile Val Asn
65                  70                  75                  80

Ser Ile Lys Arg Ser Arg Lys Ile Ile Phe Val Ile Thr His His Leu
                85                  90                  95

Leu Lys Asp Pro Leu Cys Lys Arg Phe Lys Val His His Ala Val Gln
            100                 105                 110

Gln Ala Ile Glu Gln Asn Leu Asp Ser Ile Ile Leu Val Phe Leu Glu
        115                 120                 125

Glu Ile Pro Asp Tyr Lys Leu Asn His Ala Leu Cys Leu Arg Arg Gly
    130                 135                 140

Met Phe Lys Ser His Cys Ile Leu Asn Trp Pro Val Gln Lys Glu Arg
145                 150                 155                 160

Ile Gly Ala Phe Arg His Lys Leu Gln Val Ala Leu Gly Ser Lys Asn
```

```
                165                 170                 175

Ser Val His

<210> SEQ ID NO 19
<211> LENGTH: 187
<212> TYPE: PRT
<213> ORGANISM: Homo sapiens

<400> SEQUENCE: 19

Lys Phe Tyr Phe His Leu Met Leu Leu Ala Gly Cys Ile Lys Tyr Gly
1               5                   10                  15

Arg Gly Glu Asn Ile Tyr Asp Ala Phe Val Ile Tyr Ser Ser Gln Asp
            20                  25                  30

Glu Asp Trp Val Arg Asn Glu Leu Val Lys Asn Leu Glu Glu Gly Val
        35                  40                  45

Pro Pro Phe Gln Leu Cys Leu His Tyr Arg Asp Phe Ile Pro Gly Val
    50                  55                  60

Ala Ile Ala Ala Asn Ile Ile His Glu Gly Phe His Lys Ser Arg Lys
65                  70                  75                  80

Val Ile Val Val Ser Gln His Phe Ile Gln Ser Arg Trp Cys Ile
                85                  90                  95

Phe Glu Tyr Glu Ile Ala Gln Thr Trp Gln Phe Leu Ser Ser Arg Ala
            100                 105                 110

Gly Ile Ile Phe Ile Val Leu Gln Lys Val Glu Lys Thr Leu Leu Arg
        115                 120                 125

Gln Gln Val Glu Leu Tyr Arg Leu Leu Ser Arg Asn Thr Tyr Leu Glu
    130                 135                 140

Trp Glu Asp Ser Val Leu Gly Arg His Ile Phe Trp Arg Arg Leu Arg
145                 150                 155                 160

Lys Ala Leu Leu Asp Gly Lys Ser Trp Asn Pro Glu Gly Thr Val Gly
                165                 170                 175

Thr Gly Cys Asn Trp Gln Glu Ala Thr Ser Ile
            180                 185

<210> SEQ ID NO 20
<211> LENGTH: 198
<212> TYPE: PRT
<213> ORGANISM: Homo sapiens

<400> SEQUENCE: 20

Thr Lys Phe Arg Gly Phe Cys Phe Ile Cys Tyr Lys Thr Ala Gln Arg
1               5                   10                  15

Leu Val Phe Lys Asp His Pro Gln Gly Thr Glu Pro Asp Met Tyr Lys
            20                  25                  30

Tyr Asp Ala Tyr Leu Cys Phe Ser Ser Lys Asp Phe Thr Trp Val Gln
        35                  40                  45

Asn Ala Leu Leu Lys His Leu Asp Thr Gln Tyr Ser Asp Gln Asn Arg
    50                  55                  60

Phe Asn Leu Cys Phe Glu Glu Arg Asp Phe Val Pro Gly Glu Asn Arg
65                  70                  75                  80

Ile Ala Asn Ile Gln Asp Ala Ile Trp Asn Ser Arg Lys Ile Val Cys
                85                  90                  95

Leu Val Ser Arg His Phe Leu Arg Asp Gly Trp Cys Leu Glu Ala Phe
            100                 105                 110

Ser Tyr Ala Gln Gly Arg Cys Leu Ser Asp Leu Asn Ser Ala Leu Ile
        115                 120                 125
```

Met Val Val Gly Ser Leu Ser Gln Tyr Gln Leu Met Lys His Gln
130                 135                 140

Ser Ile Arg Gly Phe Val Gln Lys Gln Gln Tyr Leu Arg Trp Pro Glu
145                 150                 155                 160

Asp Phe Gln Asp Val Gly Trp Phe Leu His Lys Leu Ser Gln Gln Ile
                165                 170                 175

Leu Lys Lys Glu Lys Glu Lys Lys Asp Asn Asn Ile Pro Leu Gln
            180                 185                 190

Thr Val Ala Thr Ile Ser
            195

<210> SEQ ID NO 21
<211> LENGTH: 189
<212> TYPE: PRT
<213> ORGANISM: Homo sapiens

<400> SEQUENCE: 21

Tyr Leu Asp Leu Pro Trp Tyr Leu Arg Met Val Cys Gln Trp Thr Gln
1               5                   10                  15

Thr Arg Arg Arg Ala Arg Asn Ile Pro Leu Glu Glu Leu Gln Arg Asn
            20                  25                  30

Leu Gln Phe His Ala Phe Ile Ser Tyr Ser Glu His Asp Ser Ala Trp
        35                  40                  45

Val Lys Ser Glu Leu Val Pro Tyr Leu Glu Lys Glu Asp Ile Gln Ile
50                  55                  60

Cys Leu His Glu Arg Asn Phe Val Pro Gly Lys Ser Ile Val Glu Asn
65                  70                  75                  80

Ile Ile Asn Cys Ile Glu Lys Ser Tyr Lys Ser Ile Phe Val Leu Ser
                85                  90                  95

Pro Asn Phe Val Gln Ser Glu Trp Cys His Tyr Glu Leu Tyr Phe Ala
            100                 105                 110

His His Asn Leu Phe His Glu Gly Ser Asn Asn Leu Ile Leu Ile Leu
        115                 120                 125

Leu Glu Pro Ile Pro Gln Asn Ser Ile Pro Asn Lys Tyr His Lys Leu
130                 135                 140

Lys Ala Leu Met Thr Gln Arg Thr Tyr Leu Gln Trp Pro Lys Glu Lys
145                 150                 155                 160

Ser Lys Arg Gly Leu Phe Trp Ala Asn Ile Arg Ala Ala Phe Asn Met
                165                 170                 175

Lys Leu Thr Leu Val Thr Glu Asn Asn Asp Val Lys Ser
            180                 185

<210> SEQ ID NO 22
<211> LENGTH: 189
<212> TYPE: PRT
<213> ORGANISM: Homo sapiens

<400> SEQUENCE: 22

His Leu Tyr Phe Trp Asp Val Trp Tyr Ile Tyr His Phe Cys Lys Ala
1               5                   10                  15

Lys Ile Lys Gly Tyr Gln Arg Leu Ile Ser Pro Asp Cys Cys Tyr Asp
            20                  25                  30

Ala Phe Ile Val Tyr Asp Thr Lys Asp Pro Ala Val Thr Glu Trp Val
        35                  40                  45

Leu Ala Glu Leu Val Ala Lys Leu Glu Asp Pro Arg Glu Lys His Phe
50                  55                  60

```
Asn Leu Cys Leu Glu Glu Arg Asp Trp Leu Pro Gly Gln Pro Val Leu
 65                  70                  75                  80

Glu Asn Leu Ser Gln Ser Ile Gln Leu Ser Lys Lys Thr Val Phe Val
                 85                  90                  95

Met Thr Asp Lys Tyr Ala Lys Thr Glu Asn Phe Lys Ile Ala Phe Tyr
            100                 105                 110

Leu Ser His Gln Arg Leu Met Asp Glu Lys Val Asp Val Ile Ile Leu
            115                 120                 125

Ile Phe Leu Glu Lys Pro Phe Gln Lys Ser Lys Phe Leu Gln Leu Arg
            130                 135                 140

Lys Arg Leu Cys Gly Ser Ser Val Leu Glu Trp Pro Thr Asn Pro Gln
145                 150                 155                 160

Ala His Pro Tyr Phe Trp Gln Cys Leu Lys Asn Ala Leu Ala Thr Asp
                165                 170                 175

Asn His Val Ala Tyr Ser Gln Val Phe Lys Glu Thr Val
            180                 185
```

<210> SEQ ID NO 23
<211> LENGTH: 193
<212> TYPE: PRT
<213> ORGANISM: Homo sapiens

<400> SEQUENCE: 23

```
His His Leu Phe Tyr Trp Asp Val Trp Phe Ile Tyr Asn Val Cys Leu
  1               5                  10                  15

Ala Lys Val Lys Gly Tyr Arg Ser Leu Ser Thr Ser Gln Thr Phe Tyr
                 20                  25                  30

Asp Ala Tyr Ile Ser Tyr Asp Thr Lys Asp Ala Ser Val Thr Asp Trp
             35                  40                  45

Val Ile Asn Glu Leu Arg Tyr His Leu Glu Glu Ser Arg Asp Lys Asn
 50                  55                  60

Val Leu Leu Cys Leu Glu Glu Arg Asp Trp Asp Pro Gly Leu Ala Ile
 65                  70                  75                  80

Ile Asp Asn Leu Met Gln Ser Ile Asn Gln Ser Lys Lys Thr Val Phe
                 85                  90                  95

Val Leu Thr Lys Lys Tyr Ala Lys Ser Trp Asn Phe Lys Thr Ala Phe
            100                 105                 110

Tyr Leu Ala Leu Gln Arg Leu Met Asp Glu Asn Met Asp Val Ile Ile
            115                 120                 125

Phe Ile Leu Leu Glu Pro Val Leu Gln His Ser Gln Tyr Leu Arg Leu
            130                 135                 140

Arg Gln Arg Ile Cys Lys Ser Ser Ile Leu Gln Trp Pro Asp Asn Pro
145                 150                 155                 160

Lys Ala Glu Gly Leu Phe Trp Gln Thr Leu Arg Asn Val Val Leu Thr
                165                 170                 175

Glu Asn Asp Ser Arg Tyr Asn Asn Met Tyr Val Asp Ser Ile Lys Gln
            180                 185                 190

Tyr
```

<210> SEQ ID NO 24
<211> LENGTH: 193
<212> TYPE: PRT
<213> ORGANISM: Homo sapiens

<400> SEQUENCE: 24

-continued

Gly Trp Asp Leu Trp Tyr Cys Phe His Leu Cys Leu Ala Trp Leu Pro
1               5                   10                  15

Trp Arg Gly Arg Gln Ser Gly Arg Asp Glu Asp Ala Leu Pro Tyr Asp
            20                  25                  30

Ala Phe Val Val Phe Asp Lys Thr Gln Ser Ala Val Ala Asp Trp Val
            35                  40                  45

Tyr Asn Glu Leu Arg Gly Gln Leu Glu Glu Cys Arg Gly Arg Trp Ala
    50                  55                  60

Leu Arg Leu Cys Leu Glu Arg Asp Trp Leu Pro Gly Lys Thr Leu
65                  70                  75                  80

Phe Glu Asn Leu Trp Ala Ser Val Tyr Gly Ser Arg Lys Thr Leu Phe
                85                  90                  95

Val Leu Ala His Thr Asp Arg Val Ser Gly Leu Leu Arg Ala Ser Phe
                100                 105                 110

Leu Leu Ala Gln Gln Arg Leu Leu Glu Asp Arg Lys Asp Val Val Val
            115                 120                 125

Leu Val Ile Leu Ser Pro Asp Gly Arg Arg Ser Arg Tyr Val Arg Leu
            130                 135                 140

Arg Gln Arg Leu Cys Arg Gln Ser Val Leu Leu Trp Pro His Gln Pro
145                 150                 155                 160

Ser Gly Gln Arg Ser Phe Trp Ala Gln Leu Gly Met Ala Leu Thr Arg
                165                 170                 175

Asp Asn His His Phe Tyr Asn Arg Asn Phe Cys Gln Gly Pro Thr Ala
                180                 185                 190

Glu

<210> SEQ ID NO 25
<211> LENGTH: 214
<212> TYPE: PRT
<213> ORGANISM: Homo sapiens
<400> SEQUENCE: 25

Cys Leu His Phe Asp Leu Pro Trp Tyr Leu Arg Met Leu Gly Gln Cys
1               5                   10                  15

Thr Gln Thr Trp His Arg Val Arg Lys Thr Thr Gln Glu Gln Leu Lys
            20                  25                  30

Arg Asn Val Arg Phe His Ala Phe Ile Ser Tyr Ser Glu His Asp Ser
            35                  40                  45

Leu Trp Val Lys Asn Glu Leu Ile Pro Asn Leu Glu Lys Glu Asp Gly
    50                  55                  60

Ser Ile Leu Ile Cys Leu Tyr Glu Ser Tyr Phe Asp Pro Gly Lys Ser
65                  70                  75                  80

Ile Ser Glu Asn Ile Val Ser Phe Ile Glu Lys Ser Tyr Lys Ser Ile
                85                  90                  95

Phe Val Leu Ser Pro Asn Phe Val Gln Asn Glu Trp Cys His Tyr Glu
                100                 105                 110

Phe Tyr Phe Ala His His Asn Leu Phe His Glu Asn Ser Asp His Ile
            115                 120                 125

Ile Leu Ile Leu Leu Glu Pro Ile Pro Phe Tyr Cys Ile Pro Thr Arg
            130                 135                 140

Tyr His Lys Leu Lys Ala Leu Leu Glu Lys Lys Ala Tyr Leu Glu Trp
145                 150                 155                 160

Pro Lys Asp Arg Arg Lys Cys Gly Leu Phe Trp Ala Asn Leu Arg Ala
                165                 170                 175

```
Ala Ile Asn Val Asn Val Leu Ala Thr Arg Glu Met Tyr Glu Leu Gln
            180                 185                 190

Thr Phe Thr Glu Leu Asn Glu Glu Ser Arg Gly Ser Thr Ile Ser Leu
            195                 200                 205

Met Arg Thr Asp Cys Leu
    210
```

<210> SEQ ID NO 26
<211> LENGTH: 172
<212> TYPE: PRT
<213> ORGANISM: Homo sapiens

<400> SEQUENCE: 26

```
Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170
```

<210> SEQ ID NO 27
<211> LENGTH: 712
<212> TYPE: PRT
<213> ORGANISM: Homo sapiens

<400> SEQUENCE: 27

```
Met Ala Cys Thr Gly Pro Ser Leu Pro Ser Ala Phe Asp Ile Leu Gly
1               5                   10                  15

Ala Ala Gly Gln Asp Lys Leu Leu Tyr Leu Lys His Lys Leu Lys Thr
            20                  25                  30

Pro Arg Pro Gly Cys Gln Gly Gln Asp Leu Leu His Ala Met Val Leu
        35                  40                  45

Leu Lys Leu Gly Gln Glu Thr Glu Ala Arg Ile Ser Leu Glu Ala Leu
    50                  55                  60

Lys Ala Asp Ala Val Ala Arg Leu Val Ala Arg Gln Trp Ala Gly Val
65                  70                  75                  80

Asp Ser Thr Glu Asp Pro Glu Glu Pro Pro Asp Val Ser Trp Ala Val
                85                  90                  95

Ala Arg Leu Tyr His Leu Leu Ala Glu Glu Lys Leu Cys Pro Ala Ser
            100                 105                 110
```

```
Leu Arg Asp Val Ala Tyr Gln Glu Ala Val Arg Thr Leu Ser Ser Arg
        115                 120                 125

Asp Asp His Arg Leu Gly Glu Leu Gln Asp Glu Ala Arg Asn Arg Cys
    130                 135                 140

Gly Trp Asp Ile Ala Gly Asp Pro Gly Ser Ile Arg Thr Leu Gln Ser
145                 150                 155                 160

Asn Leu Gly Cys Leu Pro Pro Ser Ser Ala Leu Pro Ser Gly Thr Arg
                165                 170                 175

Ser Leu Pro Arg Pro Ile Asp Gly Val Ser Asp Trp Ser Gln Gly Cys
            180                 185                 190

Ser Leu Arg Ser Thr Gly Ser Pro Ala Ser Leu Ala Ser Asn Leu Glu
        195                 200                 205

Ile Ser Gln Ser Pro Thr Met Pro Phe Leu Ser Leu His Arg Ser Pro
    210                 215                 220

His Gly Pro Ser Lys Leu Cys Asp Asp Pro Gln Ala Ser Leu Val Pro
225                 230                 235                 240

Glu Pro Val Pro Gly Gly Cys Gln Glu Pro Glu Met Ser Trp Pro
                245                 250                 255

Pro Ser Gly Glu Ile Ala Ser Pro Pro Glu Leu Pro Ser Ser Pro Pro
            260                 265                 270

Pro Gly Leu Pro Glu Val Ala Pro Asp Ala Thr Ser Thr Gly Leu Pro
        275                 280                 285

Asp Thr Pro Ala Ala Pro Glu Thr Ser Thr Asn Tyr Pro Val Glu Cys
    290                 295                 300

Thr Glu Gly Ser Ala Gly Pro Gln Ser Leu Pro Leu Pro Ile Leu Glu
305                 310                 315                 320

Pro Val Lys Asn Pro Cys Ser Val Lys Asp Gln Thr Pro Leu Gln Leu
                325                 330                 335

Ser Val Glu Asp Thr Thr Ser Pro Asn Thr Lys Pro Cys Pro Pro Thr
            340                 345                 350

Pro Thr Thr Pro Glu Thr Ser Pro Pro Pro Pro Pro Pro Pro Pro Ser
        355                 360                 365

Ser Thr Pro Cys Ser Ala His Leu Thr Pro Ser Ser Leu Phe Pro Ser
    370                 375                 380

Ser Leu Glu Ser Ser Ser Glu Gln Lys Phe Tyr Asn Phe Val Ile Leu
385                 390                 395                 400

His Ala Arg Ala Asp Glu His Ile Ala Leu Arg Val Arg Glu Lys Leu
                405                 410                 415

Glu Ala Leu Gly Val Pro Asp Gly Ala Thr Phe Cys Glu Asp Phe Gln
            420                 425                 430

Val Pro Gly Arg Gly Glu Leu Ser Cys Leu Gln Asp Ala Ile Asp His
        435                 440                 445

Ser Ala Phe Ile Ile Leu Leu Leu Thr Ser Asn Phe Asp Cys Arg Leu
    450                 455                 460

Ser Leu His Gln Val Asn Gln Ala Met Met Ser Asn Leu Thr Arg Gln
465                 470                 475                 480

Gly Ser Pro Asp Cys Val Ile Pro Phe Leu Pro Leu Glu Ser Ser Pro
                485                 490                 495

Ala Gln Leu Ser Ser Asp Thr Ala Ser Leu Leu Ser Gly Leu Val Arg
            500                 505                 510

Leu Asp Glu His Ser Gln Ile Phe Ala Arg Lys Val Ala Asn Thr Phe
        515                 520                 525

Lys Pro His Arg Leu Gln Ala Arg Lys Ala Met Trp Arg Lys Glu Gln
```

-continued

```
                530                 535                 540
Asp Thr Arg Ala Leu Arg Glu Gln Ser Gln His Leu Asp Gly Glu Arg
545                 550                 555                 560

Met Gln Ala Ala Ala Leu Asn Ala Ala Tyr Ser Ala Tyr Leu Gln Ser
                565                 570                 575

Tyr Leu Ser Tyr Gln Ala Gln Met Glu Gln Leu Gln Val Ala Phe Gly
                580                 585                 590

Ser His Met Ser Phe Gly Thr Gly Ala Pro Tyr Gly Ala Arg Met Pro
                595                 600                 605

Phe Gly Gly Gln Val Pro Leu Gly Ala Pro Pro Phe Pro Thr Trp
610                 615                 620

Pro Gly Cys Pro Gln Pro Pro Leu His Ala Trp Gln Ala Gly Thr
625                 630                 635                 640

Pro Pro Pro Pro Ser Pro Gln Pro Ala Ala Phe Pro Gln Ser Leu Pro
                645                 650                 655

Phe Pro Gln Ser Pro Ala Phe Pro Thr Ala Ser Pro Ala Pro Pro Gln
                660                 665                 670

Ser Pro Gly Leu Gln Pro Leu Ile Ile His His Ala Gln Met Val Gln
675                 680                 685

Leu Gly Leu Asn Asn His Met Trp Asn Gln Arg Gly Ser Gln Ala Pro
690                 695                 700

Glu Asp Lys Thr Gln Glu Ala Glu
705                 710
```

<210> SEQ ID NO 28
<211> LENGTH: 374
<212> TYPE: PRT
<213> ORGANISM: Homo sapiens

<400> SEQUENCE: 28

```
Met Ala Ile Arg Lys Lys Ser Thr Lys Ser Pro Pro Val Leu Ser His
1               5                   10                  15

Glu Phe Val Leu Gln Asn His Ala Asp Ile Val Ser Cys Val Ala Met
                20                  25                  30

Val Phe Leu Leu Gly Leu Met Phe Glu Ile Thr Ala Lys Ala Ser Ile
            35                  40                  45

Ile Phe Val Thr Leu Gln Tyr Asn Val Thr Leu Pro Ala Thr Glu Glu
        50                  55                  60

Gln Ala Thr Glu Ser Val Ser Leu Tyr Tyr Gly Ile Lys Asp Leu
65                  70                  75              80

Ala Thr Val Phe Phe Tyr Met Leu Val Ala Ile Ile His Ala Val
                85                  90                  95

Ile Gln Glu Tyr Met Leu Asp Lys Ile Asn Arg Arg Met His Phe Ser
            100                 105                 110

Lys Thr Lys His Ser Lys Phe Asn Glu Ser Gly Gln Leu Ser Ala Phe
        115                 120                 125

Tyr Leu Phe Ala Cys Val Trp Gly Thr Phe Ile Leu Ile Ser Glu Asn
    130                 135                 140

Tyr Ile Ser Asp Pro Thr Ile Leu Trp Arg Ala Tyr Pro His Asn Leu
145                 150                 155                 160

Met Thr Phe Gln Met Lys Phe Tyr Ile Ser Gln Leu Ala Tyr Trp
                165                 170                 175

Leu His Ala Phe Pro Glu Leu Tyr Phe Gln Lys Thr Lys Lys Glu Asp
            180                 185                 190
```

```
Ile Pro Arg Gln Leu Val Tyr Ile Gly Leu Tyr Leu Phe His Ile Ala
            195                 200                 205

Gly Ala Tyr Leu Leu Asn Leu Asn His Leu Gly Leu Val Leu Leu Val
        210                 215                 220

Leu His Tyr Phe Val Glu Phe Leu Phe His Ile Ser Arg Leu Phe Tyr
225                 230                 235                 240

Phe Ser Asn Glu Lys Tyr Gln Lys Gly Phe Ser Leu Trp Ala Val Leu
                245                 250                 255

Phe Val Leu Gly Arg Leu Leu Thr Leu Ile Leu Ser Val Leu Thr Val
            260                 265                 270

Gly Phe Gly Leu Ala Arg Ala Glu Asn Gln Lys Leu Asp Phe Ser Thr
        275                 280                 285

Gly Asn Phe Asn Val Leu Ala Val Arg Ile Ala Val Leu Ala Ser Ile
    290                 295                 300

Cys Val Thr Gln Ala Phe Met Met Trp Lys Phe Ile Asn Phe Gln Leu
305                 310                 315                 320

Arg Arg Trp Arg Glu His Ser Ala Phe Gln Ala Pro Ala Val Lys Lys
                325                 330                 335

Lys Pro Thr Val Thr Lys Gly Arg Ser Ser Lys Lys Gly Thr Glu Asn
            340                 345                 350

Gly Val Asn Gly Thr Leu Thr Ser Asn Val Ala Asp Ser Pro Arg Asn
        355                 360                 365

Lys Lys Glu Lys Ser Ser
        370

<210> SEQ ID NO 29
<211> LENGTH: 221
<212> TYPE: PRT
<213> ORGANISM: Homo sapiens

<400> SEQUENCE: 29

Met Ala Ser Ser Thr Ser Leu Pro Ala Pro Gly Ser Arg Pro Lys Lys
1               5                   10                  15

Pro Leu Gly Lys Met Ala Asp Trp Phe Arg Gln Thr Leu Leu Lys Lys
            20                  25                  30

Pro Lys Lys Arg Pro Asn Ser Pro Glu Ser Thr Ser Ser Asp Ala Ser
        35                  40                  45

Gln Pro Thr Ser Gln Asp Ser Pro Leu Pro Pro Ser Leu Ser Ser Val
    50                  55                  60

Thr Ser Pro Ser Leu Pro Pro Thr His Ala Ser Asp Ser Gly Ser Ser
65                  70                  75                  80

Arg Trp Ser Lys Asp Tyr Asp Val Cys Val Cys His Ser Glu Glu Asp
                85                  90                  95

Leu Val Ala Ala Gln Asp Leu Val Ser Tyr Leu Glu Gly Ser Thr Ala
            100                 105                 110

Ser Leu Arg Cys Phe Leu Gln Leu Arg Asp Ala Thr Pro Gly Gly Ala
        115                 120                 125

Ile Val Ser Glu Leu Cys Gln Ala Leu Ser Ser Ser His Cys Arg Val
    130                 135                 140

Leu Leu Ile Thr Pro Gly Phe Leu Gln Asp Pro Trp Cys Lys Tyr Gln
145                 150                 155                 160

Met Leu Gln Ala Leu Thr Glu Ala Pro Gly Ala Glu Gly Cys Thr Ile
                165                 170                 175

Pro Leu Leu Ser Gly Leu Ser Arg Ala Ala Tyr Pro Pro Glu Leu Arg
            180                 185                 190
```

```
Phe Met Tyr Tyr Val Asp Gly Arg Gly Pro Asp Gly Gly Phe Arg Gln
        195                 200                 205

Val Lys Glu Ala Val Met Arg Tyr Leu Gln Thr Leu Ser
210                 215                 220

<210> SEQ ID NO 30
<211> LENGTH: 15
<212> TYPE: PRT
<213> ORGANISM: Artificial Sequence
<220> FEATURE:
<223> OTHER INFORMATION: Synthesized

<400> SEQUENCE: 30

Gly Gly Gly Gly Ser Gly Gly Gly Ser Gly Gly Gly Gly Ser
1               5                   10                  15

<210> SEQ ID NO 31
<211> LENGTH: 261
<212> TYPE: PRT
<213> ORGANISM: Homo sapiens

<400> SEQUENCE: 31

Met Arg Glu Ser Ala Leu Glu Arg Gly Pro Val Pro Glu Ala Pro Ala
1               5                   10                  15

Gly Gly Pro Val His Ala Val Thr Val Val Thr Leu Leu Glu Lys Leu
            20                  25                  30

Ala Ser Met Leu Glu Thr Leu Arg Glu Arg Gln Gly Gly Leu Ala Arg
        35                  40                  45

Arg Gln Gly Gly Leu Ala Gly Ser Val Arg Ile Gln Ser Gly Leu
    50                  55                  60

Gly Ala Leu Ser Arg Ser His Asp Thr Thr Ser Asn Thr Leu Ala Gln
65                  70                  75                  80

Leu Leu Ala Lys Ala Glu Arg Val Ser Ser His Ala Asn Ala Ala Gln
                85                  90                  95

Glu Arg Ala Val Arg Arg Ala Ala Gln Val Gln Arg Leu Glu Ala Asn
            100                 105                 110

His Gly Leu Leu Val Ala Arg Gly Lys Leu His Val Leu Leu Phe Lys
        115                 120                 125

Glu Glu Gly Glu Val Pro Ala Ser Ala Phe Gln Lys Ala Pro Glu Pro
    130                 135                 140

Leu Gly Pro Ala Asp Gln Ser Glu Leu Gly Pro Glu Gln Leu Glu Ala
145                 150                 155                 160

Glu Val Gly Glu Ser Ser Asp Glu Glu Pro Val Glu Ser Arg Ala Gln
                165                 170                 175

Arg Leu Arg Arg Thr Gly Leu Gln Lys Val Gln Ser Leu Arg Arg Ala
            180                 185                 190

Leu Ser Gly Arg Lys Gly Pro Ala Ala Pro Pro Thr Pro Val Lys
        195                 200                 205

Pro Pro Arg Leu Gly Pro Gly Arg Ser Ala Glu Ala Gln Pro Glu Ala
    210                 215                 220

Gln Pro Ala Leu Glu Pro Thr Leu Glu Pro Glu Pro Gln Asp Thr
225                 230                 235                 240

Glu Glu Asp Pro Gly Arg Pro Gly Ala Ala Glu Glu Ala Leu Leu Gln
                245                 250                 255

Met Glu Ser Val Ala
            260
```

<210> SEQ ID NO 32
<211> LENGTH: 218
<212> TYPE: PRT
<213> ORGANISM: Homo sapiens

<400> SEQUENCE: 32

Met Met Arg Arg Glu Asp Glu Glu Glu Gly Thr Met Met Lys Ala
1               5                   10                  15

Lys Gly Asp Leu Glu Met Lys Glu Glu Glu Ile Ser Glu Thr Gly
                20                  25                  30

Glu Leu Val Gly Pro Phe Val Ser Ala Met Pro Thr Pro Met Pro His
                35                  40                  45

Asn Lys Gly Thr Arg Phe Ser Glu Ala Trp Glu Tyr Phe His Leu Ala
            50                  55                  60

Pro Ala Arg Ala Gly His His Pro Asn Gln Tyr Ala Thr Cys Arg Leu
65                  70                  75                  80

Cys Gly Arg Gln Val Ser Arg Gly Pro Gly Val Asn Val Gly Thr Thr
                    85                  90                  95

Ala Leu Trp Lys His Leu Lys Ser Met His Arg Glu Glu Leu Glu Lys
                100                 105                 110

Ser Gly His Gly Gln Ala Gly Gln Arg Gln Asp Pro Arg Pro His Gly
            115                 120                 125

Pro Gln Leu Pro Thr Gly Ile Glu Gly Asn Trp Gly Arg Leu Leu Glu
    130                 135                 140

Gln Val Gly Thr Met Ala Leu Trp Ala Ser Gln Arg Glu Lys Glu Val
145                 150                 155                 160

Leu Arg Arg Glu Arg Ala Val Glu Trp Arg Glu Arg Ala Val Glu Lys
                165                 170                 175

Arg Glu Arg Ala Leu Glu Glu Val Glu Arg Ala Ile Leu Glu Met Lys
            180                 185                 190

Trp Lys Val Arg Ala Glu Lys Gly Ala Cys Gln Arg Glu Lys Glu Leu
        195                 200                 205

Pro Ala Ala Val His Pro Phe His Phe Val
    210                 215

<210> SEQ ID NO 33
<211> LENGTH: 439
<212> TYPE: PRT
<213> ORGANISM: Homo sapiens

<400> SEQUENCE: 33

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
                20                  25                  30

Gln Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Gly Ser Phe Ser Thr Ala
                    85                  90                  95

Asp Gln Leu Glu Met Val Thr Glu Leu Leu Gly Gly Asp Met Val Asn
                100                 105                 110

```
Gln Ser Phe Ile Cys Asp Pro Asp Glu Thr Phe Ile Lys Asn Ile
        115                 120                 125

Ile Ile Gln Asp Cys Met Trp Ser Gly Phe Ser Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ser Glu Cys Ile Asp Pro Ser
                180                 185                 190

Val Val Phe Pro Tyr Pro Leu Asn Asp Ser Ser Pro Lys Ser Cys
        195                 200                 205

Ala Ser Gln Asp Ser Ser Ala Phe Ser Pro Ser Ser Asp Ser Leu Leu
210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Asp Ser Glu Glu Glu Gln
                245                 250                 255

Glu Asp Glu Glu Glu Ile Asp Val Val Ser Val Glu Lys Arg Gln Ala
                260                 265                 270

Pro Gly Lys Arg Ser Glu Ser Gly Ser Pro Ser Ala Gly Gly His Ser
                275                 280                 285

Lys Pro Pro His Ser Pro Leu Val Leu Lys Arg Cys His Val Ser Thr
        290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
                340                 345                 350

Asn Val Lys Arg Arg Thr His Asn Val Leu Glu Arg Gln Arg Arg Asn
                355                 360                 365

Glu Leu Lys Arg Ser Phe Phe Ala Leu Arg Asp Gln Ile Pro Glu Leu
        370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
                420                 425                 430

Gln Leu Arg Asn Ser Cys Ala
        435

<210> SEQ ID NO 34
<211> LENGTH: 750
<212> TYPE: PRT
<213> ORGANISM: Homo sapiens

<400> SEQUENCE: 34

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
                20                  25                  30

Tyr Leu Ala Gln Trp Leu Glu Lys Gln Asp Trp Glu His Ala Ala Asn
        35                  40                  45
```

-continued

```
Asp Val Ser Phe Ala Thr Ile Arg Phe His Asp Leu Leu Ser Gln Leu
 50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
                100                 105                 110

Arg Lys Ile Leu Glu Asn Ala Gln Arg Phe Asn Gln Ala Gln Ser Gly
            115                 120                 125

Asn Ile Gln Ser Thr Val Met Leu Asp Lys Gln Lys Glu Leu Asp Ser
130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
            195                 200                 205

Lys Arg Lys Glu Val Val His Lys Ile Ile Glu Leu Leu Asn Val Thr
210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
            275                 280                 285

Tyr Glu His Asp Pro Ile Thr Lys Asn Lys Gln Val Leu Trp Asp Arg
290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
            355                 360                 365

Asn Glu Arg Asn Thr Val Lys Gly Phe Arg Lys Phe Asn Ile Leu Gly
370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
            435                 440                 445

Glu Thr Thr Ser Leu Pro Val Val Val Ile Ser Asn Val Ser Gln Leu
450                 455                 460
```

```
Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
            485                 490                 495

Gln Leu Ser Glu Val Leu Ser Trp Gln Phe Ser Ser Val Thr Lys Arg
        500                 505                 510

Gly Leu Asn Val Asp Gln Leu Asn Met Leu Gly Glu Lys Leu Leu Gly
    515                 520                 525

Pro Asn Ala Ser Pro Asp Gly Leu Ile Pro Trp Thr Arg Phe Cys Lys
530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
            565                 570                 575

Cys Ile Met Gly Phe Ile Ser Lys Glu Arg Glu Arg Ala Leu Leu Lys
        580                 585                 590

Asp Gln Gln Pro Gly Thr Phe Leu Leu Arg Phe Ser Glu Ser Ser Arg
    595                 600                 605

Glu Gly Ala Ile Thr Phe Thr Trp Val Glu Arg Ser Gln Asn Gly Gly
610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
            645                 650                 655

Glu Asn Ile Pro Glu Asn Pro Leu Lys Tyr Leu Tyr Pro Asn Ile Asp
        660                 665                 670

Lys Asp His Ala Phe Gly Lys Tyr Tyr Ser Arg Pro Lys Glu Ala Pro
    675                 680                 685

Glu Pro Met Glu Leu Asp Gly Pro Lys Gly Thr Gly Tyr Ile Lys Thr
690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
            725                 730                 735

Ile Val Gly Ser Val Glu Phe Asp Ser Met Met Asn Thr Val
        740                 745                 750
```

<210> SEQ ID NO 35
<211> LENGTH: 750
<212> TYPE: PRT
<213> ORGANISM: Artificial Sequence
<220> FEATURE:
<223> OTHER INFORMATION: Synthesized

<400> SEQUENCE: 35

```
Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80
```

```
His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
130                 135                 140

Lys Val Arg Asn Val Lys Asp Lys Val Met Cys Ile Glu His Glu Ile
145                 150                 155                 160

Lys Ser Leu Glu Gly Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Lys Lys Met Tyr Leu Met Leu Asp Asn
        195                 200                 205

Lys Arg Lys Glu Val Val His Lys Ile Ile Glu Leu Leu Asn Val Thr
210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Ile Ser Asn Val Ser Gln Leu
450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
```

```
                500                 505                 510
Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
            530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Pro Leu Trp Asn Asp Gly
                565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
            610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
            645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
            725                 730                 735

Ile Val Gly Ser Val Glu Phe Asp Ser Met Met Asn Thr Val
            740                 745                 750

<210> SEQ ID NO 36
<211> LENGTH: 750
<212> TYPE: PRT
<213> ORGANISM: Artificial Sequence
<220> FEATURE:
<223> OTHER INFORMATION: Synthesized

<400> SEQUENCE: 36

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
```

-continued

```
            115                 120                 125
Asn Ile Gln Ser Thr Val Met Leu Asp Lys Gln Lys Glu Leu Asp Ser
        130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Lys Arg Glu His Glu Thr Asn Gly Val Ala Lys Ser Asp Gln
            180                 185                 190

Lys Gln Glu Gln Leu Leu Lys Lys Met Tyr Leu Met Leu Asp Asn
        195                 200                 205

Lys Arg Lys Glu Val Val His Lys Ile Ile Glu Leu Leu Asn Val Thr
        210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
        290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
        370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Ile Ser Asn Val Ser Gln Leu
        450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
        515                 520                 525

Pro Asn Ala Ser Pro Asp Gly Leu Ile Pro Trp Thr Arg Phe Cys Lys
        530                 535                 540
```

```
Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
            565                 570                 575

Cys Ile Met Gly Phe Ile Ser Lys Glu Arg Glu Arg Ala Leu Leu Lys
        580                 585                 590

Asp Gln Gln Pro Gly Thr Phe Leu Leu Arg Phe Ser Glu Ser Ser Arg
    595                 600                 605

Glu Gly Ala Ile Thr Phe Thr Trp Val Glu Arg Ser Gln Asn Gly Gly
610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
        675                 680                 685

Glu Pro Met Glu Leu Asp Gly Pro Lys Gly Thr Gly Tyr Ile Lys Thr
    690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
            740                 745                 750

<210> SEQ ID NO 37
<211> LENGTH: 750
<212> TYPE: PRT
<213> ORGANISM: Artificial Sequence
<220> FEATURE:
<223> OTHER INFORMATION: Synthesized

<400> SEQUENCE: 37

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Phe Leu Leu Gln
65                  70                  75                  80

His Asn Ile Arg Lys Ser Lys Arg Asn Leu Gln Asp Asn Phe Gln Glu
            85                  90                  95

Asp Pro Ile Gln Met Ser Met Ile Ile Tyr Ser Cys Leu Lys Glu Glu
        100                 105                 110

Arg Lys Ile Leu Glu Asn Ala Gln Arg Phe Asn Gln Ala Gln Ser Gly
    115                 120                 125

Asn Ile Gln Ser Thr Val Met Leu Asp Lys Gln Lys Glu Leu Asp Ser
130                 135                 140

Lys Val Arg Asn Val Lys Asp Lys Val Met Cys Ile Glu His Glu Ile
145                 150                 155                 160
```

```
Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Gln Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Ile Ser Asn Val Ser Gln Leu
    450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
        515                 520                 525

Pro Asn Ala Ser Pro Asp Gly Leu Ile Pro Trp Thr Arg Phe Cys Lys
530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575
```

```
Cys Ile Met Gly Phe Ile Ser Lys Glu Arg Glu Ala Leu Leu Lys
            580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
            610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
            645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
            725                 730                 735

Ile Val Gly Ser Val Glu Phe Asp Ser Met Met Asn Thr Val
            740                 745                 750

<210> SEQ ID NO 38
<211> LENGTH: 750
<212> TYPE: PRT
<213> ORGANISM: Artificial Sequence
<220> FEATURE:
<223> OTHER INFORMATION: Synthesized

<400> SEQUENCE: 38

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190
```

-continued

```
Lys Gln Glu Gln Leu Leu Lys Lys Met Tyr Leu Met Leu Asp Asn
            195                 200                 205
Lys Arg Lys Glu Val Val His Lys Ile Ile Glu Leu Leu Asn Val Thr
210                 215                 220
Glu Leu Thr Gln Asn Ala Leu Ile Asn Asp Glu Leu Val Glu Trp Lys
225                 230                 235                 240
Arg Arg Gln Gln Ser Ala Cys Ile Gly Gly Pro Pro Asn Ala Cys Leu
                245                 250                 255
Asp Gln Leu Gln Asn Trp Phe Thr Ile Val Ala Glu Ser Leu Gln Gln
            260                 265                 270
Val Trp Gln Gln Leu Lys Lys Leu Glu Glu Leu Glu Gln Lys Tyr Thr
        275                 280                 285
Tyr Glu His Asp Pro Ile Thr Lys Asn Lys Gln Val Leu Trp Asp Arg
    290                 295                 300
Thr Phe Ser Leu Phe Gln Gln Leu Ile Gln Ser Ser Phe Val Val Glu
305                 310                 315                 320
Arg Gln Pro Cys Met Pro Thr His Pro Gln Arg Pro Leu Val Leu Lys
                325                 330                 335
Thr Gly Val Gln Phe Thr Val Lys Leu Arg Leu Leu Val Lys Leu Gln
            340                 345                 350
Glu Leu Asn Tyr Asn Leu Lys Val Lys Val Leu Phe Asp Lys Asp Val
        355                 360                 365
Asn Glu Arg Asn Thr Val Lys Gly Phe Arg Lys Phe Asn Ile Leu Gly
    370                 375                 380
Thr His Thr Lys Val Met Asn Met Glu Glu Ser Thr Asn Gly Ser Leu
385                 390                 395                 400
Ala Ala Glu Phe Arg His Leu Gln Leu Lys Glu Gln Lys Asn Ala Gly
                405                 410                 415
Thr Arg Thr Asn Glu Gly Pro Leu Ile Val Thr Glu Glu Leu His Ser
            420                 425                 430
Leu Ser Phe Glu Thr Gln Leu Cys Gln Pro Gly Leu Val Ile Asp Leu
        435                 440                 445
Glu Thr Thr Ser Leu Pro Val Val Val Ile Ser Asn Val Ser Gln Leu
    450                 455                 460
Pro Ser Gly Trp Ala Ser Ile Leu Trp Tyr Asn Met Leu Val Ala Glu
465                 470                 475                 480
Pro Arg Asn Leu Ser Phe Phe Leu Thr Pro Pro Cys Ala Arg Trp Ala
                485                 490                 495
Gln Leu Ser Glu Val Leu Ser Trp Gln Phe Ser Ser Val Thr Lys Arg
            500                 505                 510
Gly Leu Asn Val Asp Gln Leu Asn Met Leu Gly Glu Lys Leu Leu Gly
        515                 520                 525
Pro Asn Ala Ser Pro Asp Gly Leu Ile Pro Trp Thr Arg Phe Cys Lys
    530                 535                 540
Glu Asn Ile Asn Asp Lys Asn Phe Pro Phe Trp Leu Trp Ile Glu Ser
545                 550                 555                 560
Ile Leu Glu Leu Ile Lys Lys His Leu Leu Pro Leu Trp Asn Asp Gly
                565                 570                 575
Cys Ile Met Gly Phe Ile Ser Lys Glu Arg Glu Arg Ala Leu Leu Lys
            580                 585                 590
Asp Gln Gln Pro Gly Thr Phe Leu Leu Arg Phe Ser Glu Ser Ser Arg
        595                 600                 605
Glu Gly Ala Ile Thr Phe Thr Trp Val Glu Arg Ser Gln Asn Gly Gly
```

```
                610                615                620
Glu Pro Asp Phe His Ala Val Glu Pro Tyr Thr Lys Glu Leu Ser
625                630                635                640

Ala Val Thr Phe Pro Asp Ile Ile Arg Asn Tyr Lys Val Met Ala Ala
            645                650                655

Glu Asn Ile Pro Glu Asn Pro Leu Lys Tyr Leu Tyr Pro Asn Ile Asp
                660                665                670

Lys Asp His Ala Phe Gly Lys Tyr Tyr Ser Arg Pro Lys Glu Ala Pro
            675                680                685

Glu Pro Met Glu Leu Asp Gly Pro Lys Gly Thr Gly Tyr Ile Lys Thr
690                695                700

Glu Leu Ile Ser Val Ser Glu Val His Pro Ser Arg Leu Gln Thr Thr
705                710                715                720

Asp Asn Leu Leu Pro Met Ser Pro Glu Glu Phe Asp Glu Val Ser Arg
                725                730                735

Ile Val Gly Ser Val Glu Phe Asp Ser Met Met Asn Thr Val
            740                745                750

<210> SEQ ID NO 39
<211> LENGTH: 750
<212> TYPE: PRT
<213> ORGANISM: Artificial Sequence
<220> FEATURE:
<223> OTHER INFORMATION: Synthesized

<400> SEQUENCE: 39

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
```

```
            225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
                260                 265                 270

Val Arg Gln Gln Leu Glu Lys Leu Glu Glu Leu Glu Gln Lys Tyr Thr
                275                 280                 285

Tyr Glu His Asp Pro Ile Thr Lys Asn Lys Gln Val Leu Trp Asp Arg
            290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
                340                 345                 350

Glu Leu Asn Tyr Asn Leu Lys Val Lys Val Leu Phe Asp Lys Asp Val
                355                 360                 365

Asn Glu Arg Asn Thr Val Lys Gly Phe Arg Lys Phe Asn Ile Leu Gly
            370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
                420                 425                 430

Leu Ser Phe Glu Thr Gln Leu Cys Gln Pro Gly Leu Val Ile Asp Leu
                435                 440                 445

Glu Thr Thr Ser Leu Pro Val Val Val Ile Ser Asn Val Ser Gln Leu
            450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
                500                 505                 510

Gly Leu Asn Val Asp Gln Leu Asn Met Leu Gly Glu Lys Leu Leu Gly
                515                 520                 525

Pro Asn Ala Ser Pro Asp Gly Leu Ile Pro Trp Thr Arg Phe Cys Lys
            530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
                610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655
```

```
Glu Asn Ile Pro Glu Asn Pro Leu Lys Tyr Leu Tyr Pro Asn Ile Asp
            660                 665                 670

Lys Asp His Ala Phe Gly Lys Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
            740                 745                 750

<210> SEQ ID NO 40
<211> LENGTH: 750
<212> TYPE: PRT
<213> ORGANISM: Artificial Sequence
<220> FEATURE:
<223> OTHER INFORMATION: Synthesized

<400> SEQUENCE: 40

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
            35                  40                  45

Asp Val Ser Phe Ala Thr Ile Arg Phe His Asp Leu Leu Ser Gln Leu
50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
            115                 120                 125

Asn Ile Gln Ser Thr Val Met Leu Asp Lys Gln Lys Glu Leu Asp Ser
            130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
            195                 200                 205

Lys Arg Lys Glu Val Val His Lys Ile Ile Glu Leu Leu Asn Val Thr
            210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270
```

```
Val Arg Gln Gln Leu Lys Lys Leu Glu Glu Leu Glu Arg Lys Tyr Thr
    275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
                340                 345                 350

Glu Leu Asn Tyr Asn Leu Lys Val Lys Val Leu Phe Asp Lys Asp Val
            355                 360                 365

Asn Glu Arg Asn Thr Val Lys Gly Phe Arg Lys Phe Asn Ile Leu Gly
        370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
                420                 425                 430

Leu Ser Phe Glu Thr Gln Leu Cys Gln Pro Gly Leu Val Ile Asp Leu
        435                 440                 445

Glu Thr Thr Ser Leu Pro Val Val Ile Ser Asn Val Ser Gln Leu
450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Cys Ala Arg Trp Ala
                485                 490                 495

Gln Leu Ser Glu Val Leu Ser Trp Gln Phe Ser Ser Val Thr Lys Arg
                500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
        530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
        610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
                660                 665                 670

Lys Asp His Ala Phe Gly Lys Tyr Tyr Ser Arg Pro Lys Glu Ala Pro
            675                 680                 685
```

```
Glu Pro Met Glu Leu Asp Gly Pro Lys Gly Thr Gly Tyr Ile Lys Thr
        690             695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
                740                 745                 750

<210> SEQ ID NO 41
<211> LENGTH: 750
<212> TYPE: PRT
<213> ORGANISM: Artificial Sequence
<220> FEATURE:
<223> OTHER INFORMATION: Synthesized

<400> SEQUENCE: 41

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Met Tyr Leu Met Leu Asp Asn
        195                 200                 205

Lys Arg Lys Glu Val Val His Lys Ile Ile Glu Leu Leu Asn Val Thr
210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Asn Gln Val Leu Trp Asp Arg
    290                 295                 300
```

-continued

```
Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
            325                 330                 335

Thr Gly Val Gln Phe Thr Val Lys Leu Arg Leu Leu Val Lys Leu Gln
        340                 345                 350

Glu Leu Asn Tyr Asn Leu Lys Val Lys Val Leu Phe Asp Lys Asp Val
    355                 360                 365

Asn Glu Arg Asn Thr Val Lys Gly Phe Arg Lys Phe Asn Ile Leu Gly
370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Ile Ser Asn Val Ser Gln Leu
    450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
        515                 520                 525

Pro Asn Ala Ser Pro Asp Gly Leu Ile Pro Trp Thr Arg Phe Cys Lys
530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
        595                 600                 605

Glu Gly Ala Ile Thr Phe Thr Trp Val Glu Arg Ser Gln Asn Gly Gly
    610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
        675                 680                 685

Glu Pro Met Glu Leu Asp Gly Pro Lys Gly Thr Gly Tyr Ile Lys Thr
    690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
```

```
                    725                 730                 735
Ile Val Gly Ser Val Glu Phe Asp Ser Met Met Asn Thr Val
                740                 745                 750

<210> SEQ ID NO 42
<211> LENGTH: 750
<212> TYPE: PRT
<213> ORGANISM: Artificial Sequence
<220> FEATURE:
<223> OTHER INFORMATION: Synthesized

<400> SEQUENCE: 42

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
```

Glu Leu Asn Tyr Asn Leu Lys Val Lys Val Leu Phe Asp Lys Asp Val
            340                 345                 350
Asn Glu Arg Asn Thr Val Lys Gly Phe Arg Lys Phe Asn Ile Leu Asp
        355                 360                 365
Thr His Thr Lys Val Met Asn Met Glu Glu Ser Thr Asn Gly Ser Leu
    370                 375                 380
Ala Ala Glu Phe Arg His Leu Gln Leu Lys Glu Gln Lys Asn Ala Gly
385                 390                 395                 400
Thr Arg Thr Asn Glu Gly Pro Leu Ile Val Thr Glu Glu Leu His Ser
            405                 410                 415
Leu Ser Phe Glu Thr Gln Leu Cys Gln Pro Gly Leu Val Ile Asp Leu
        420                 425                 430
Glu Thr Thr Ser Leu Pro Val Val Ile Ser Asn Val Ser Gln Leu
    435                 440                 445
Pro Ser Gly Trp Ala Ser Ile Leu Trp Tyr Asn Met Leu Val Ala Glu
450                 455                 460
Pro Arg Asn Leu Ser Phe Phe Leu Thr Pro Pro Cys Ala Arg Trp Ala
            465                 470                 475             480
Gln Leu Ser Glu Val Leu Ser Trp Gln Phe Ser Ser Val Thr Lys Arg
        485                 490                 495
Gly Leu Asn Val Asp Gln Leu Asn Met Leu Gly Glu Lys Leu Leu Gly
    500                 505                 510
Pro Asn Ala Ser Pro Asp Gly Leu Ile Pro Trp Thr Arg Phe Cys Lys
515                 520                 525
Glu Asn Ile Asn Asp Lys Asn Phe Pro Phe Trp Leu Trp Ile Glu Ser
            530                 535                 540
Ile Leu Glu Leu Ile Lys Lys His Leu Leu Pro Leu Trp Asn Asp Gly
545                 550                 555             560
Cys Ile Met Gly Phe Ile Ser Lys Glu Arg Glu Arg Ala Leu Leu Lys
        565                 570                 575
Asp Gln Gln Pro Gly Thr Phe Leu Leu Arg Phe Ser Glu Ser Ser Arg
    580                 585                 590
Glu Gly Ala Ile Thr Phe Thr Trp Val Glu Arg Ser Gln Asn Gly Gly
595                 600                 605
Glu Pro Asp Phe His Ala Val Glu Pro Tyr Thr Lys Lys Glu Leu Ser
            610                 615                 620
Ala Val Thr Phe Pro Asp Ile Ile Arg Asn Tyr Lys Val Met Ala Ala
625                 630                 635             640
Glu Asn Ile Pro Glu Asn Pro Leu Lys Tyr Leu Tyr Pro Asn Ile Asp
        645                 650                 655
Lys Asp His Ala Phe Gly Lys Tyr Tyr Ser Arg Pro Lys Glu Ala Pro
    660                 665                 670
Glu Pro Met Glu Leu Asp Gly Pro Lys Gly Thr Gly Tyr Ile Lys Thr
675                 680                 685
Glu Leu Ile Ser Val Ser Glu Val His Pro Ser Arg Leu Gln Thr Thr
            690                 695                 700
Asp Asn Leu Leu Pro Met Ser Pro Glu Glu Phe Asp Glu Val Ser Arg
705                 710                 715             720
Ile Val Gly Ser Val Glu Phe Asp Ser Met Met Asn Thr Val
        725                 730                 735

<210> SEQ ID NO 43

```
<211> LENGTH: 750
<212> TYPE: PRT
<213> ORGANISM: Artificial Sequence
<220> FEATURE:
<223> OTHER INFORMATION: Synthesized

<400> SEQUENCE: 43
```

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
    370                 375                 380

Met His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
            405                 410                 415

Thr Arg Thr Asn Glu Gly Pro Leu Ile Val Thr Glu Glu Leu His Ser
        420                 425                 430

Leu Ser Phe Glu Thr Gln Leu Cys Gln Pro Gly Leu Val Ile Asp Leu
    435                 440                 445

Glu Thr Thr Ser Leu Pro Val Val Ile Ser Asn Val Ser Gln Leu
450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Cys Ala Arg Trp Ala
            485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
            565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
            610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
            645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
            725                 730                 735

Ile Val Gly Ser Val Glu Phe Asp Ser Met Met Asn Thr Val
            740                 745                 750

<210> SEQ ID NO 44
<211> LENGTH: 770
<212> TYPE: PRT
<213> ORGANISM: Homo sapiens

<400> SEQUENCE: 44

Met Ala Gln Trp Asn Gln Leu Gln Gln Leu Asp Thr Arg Tyr Leu Glu

-continued

```
1               5                   10                  15
Gln Leu His Gln Leu Tyr Ser Asp Ser Phe Pro Met Glu Leu Arg Gln
                20                  25                  30
Phe Leu Ala Pro Trp Ile Glu Ser Gln Asp Trp Ala Tyr Ala Ala Ser
                35                  40                  45
Lys Glu Ser His Ala Thr Leu Val Phe His Asn Leu Leu Gly Glu Ile
            50                  55                  60
Asp Gln Gln Tyr Ser Arg Phe Leu Gln Glu Ser Asn Val Leu Tyr Gln
65                  70                  75                  80
His Asn Leu Arg Arg Ile Lys Gln Phe Leu Gln Ser Arg Tyr Leu Glu
                85                  90                  95
Lys Pro Met Glu Ile Ala Arg Ile Val Ala Arg Cys Leu Trp Glu Glu
                100                 105                 110
Ser Arg Leu Leu Gln Thr Ala Ala Thr Ala Ala Gln Gln Gly Gly Gln
                115                 120                 125
Ala Asn His Pro Thr Ala Ala Val Val Thr Glu Lys Gln Gln Met Leu
130                 135                 140
Glu Gln His Leu Gln Asp Val Arg Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
                180                 185                 190
Gln Ser Val Thr Arg Gln Lys Met Gln Gln Leu Glu Gln Met Leu Thr
                195                 200                 205
Ala Leu Asp Gln Met Arg Arg Ser Ile Val Ser Glu Leu Ala Gly Leu
210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
                260                 265                 270
Ser Gln Leu Gln Thr Arg Gln Gln Ile Lys Lys Leu Glu Glu Leu Gln
                275                 280                 285
Gln Lys Val Ser Tyr Lys Gly Asp Pro Ile Val Gln His Arg Pro Met
                290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
                340                 345                 350
Val Lys Phe Pro Glu Leu Asn Tyr Gln Leu Lys Ile Lys Val Cys Ile
                355                 360                 365
Asp Lys Asp Ser Gly Asp Val Ala Ala Leu Arg Gly Ser Arg Lys Phe
                370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
                420                 425                 430
```

Thr Glu Glu Leu His Leu Ile Thr Phe Glu Thr Glu Val Tyr His Gln
            435                 440                 445

Gly Leu Lys Ile Asp Leu Glu Thr His Ser Leu Pro Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
            530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
    675                 680                 685

Pro Glu Ser Gln Glu His Pro Glu Ala Asp Pro Gly Ser Ala Ala Pro
            690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
            755                 760                 765

Pro Met
    770

<210> SEQ ID NO 45
<211> LENGTH: 770
<212> TYPE: PRT
<213> ORGANISM: Artificial Sequence
<220> FEATURE:
<223> OTHER INFORMATION: Synthesized

<400> SEQUENCE: 45

Met Ala Gln Trp Asn Gln Leu Gln Gln Leu Asp Thr Arg Tyr Leu Glu
1               5                   10                  15

-continued

```
Gln Leu His Gln Leu Tyr Ser Asp Ser Phe Pro Met Glu Leu Arg Gln
             20                  25                  30
Phe Leu Ala Pro Trp Ile Glu Ser Gln Asp Trp Ala Tyr Ala Ala Ser
         35                  40                  45
Lys Glu Ser His Ala Thr Leu Val Phe His Asn Leu Leu Gly Glu Ile
 50                  55                  60
Asp Gln Gln Tyr Ser Arg Phe Leu Gln Glu Ser Asn Val Leu Tyr Gln
 65                  70                  75                  80
His Asn Leu Arg Arg Ile Lys Gln Phe Leu Gln Ser Arg Tyr Leu Glu
                 85                  90                  95
Lys Pro Met Glu Ile Ala Arg Ile Val Ala Arg Cys Leu Trp Glu Glu
            100                 105                 110
Ser Arg Leu Leu Gln Thr Ala Ala Thr Ala Ala Gln Gln Gly Gly Gln
            115                 120                 125
Ala Asn His Pro Thr Ala Ala Val Val Thr Glu Lys Gln Gln Met Leu
130                 135                 140
Glu Gln His Leu Gln Asp Val Arg Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
            180                 185                 190
Gln Ser Val Thr Arg Gln Lys Met Gln Gln Leu Glu Gln Met Leu Thr
        195                 200                 205
Ala Leu Asp Gln Met Arg Arg Ser Ile Val Ser Glu Leu Ala Gly Leu
    210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
            260                 265                 270
Ser Gln Leu Gln Thr Arg Gln Gln Ile Lys Lys Leu Glu Glu Leu Gln
        275                 280                 285
Gln Lys Val Ser Tyr Lys Gly Asp Pro Ile Val Gln His Arg Pro Met
    290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
        355                 360                 365
Asp Lys Asp Ser Gly Asp Val Ala Ala Leu Arg Gly Ser Arg Lys Phe
    370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
            420                 425                 430
```

```
Thr Glu Glu Leu His Leu Ile Thr Phe Glu Thr Glu Val Tyr His Gln
            435                 440                 445

Gly Leu Lys Ile Asp Leu Glu Thr His Ser Leu Pro Val Val Val Ile
        450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
        610                 615                 620

Glu Lys Asp Ile Ser Gly Lys Thr Gln Ile Gln Ser Val Glu Pro Tyr
625                 630                 635                 640

Thr Lys Gln Gln Leu Asn Ile Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
        690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met
770

<210> SEQ ID NO 46
<211> LENGTH: 770
<212> TYPE: PRT
<213> ORGANISM: Artificial Sequence
<220> FEATURE:
<223> OTHER INFORMATION: Synthesized

<400> SEQUENCE: 46

Met Ala Gln Trp Asn Gln Leu Gln Gln Leu Asp Thr Arg Tyr Leu Glu
1               5                   10                  15
```

```
Gln Leu His Gln Leu Tyr Ser Asp Ser Phe Pro Met Glu Leu Arg Gln
             20                  25                  30

Phe Leu Ala Pro Trp Ile Glu Ser Gln Asp Trp Ala Tyr Ala Ala Ser
             35                  40                  45

Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
             85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
            130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
            165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
            195                 200                 205

Ala Leu Asp Gln Met Arg Arg Ser Ile Val Ser Glu Leu Ala Gly Leu
            210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
            245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
            275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
            325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
            355                 360                 365

Asp Lys Asp Ser Gly Asp Val Ala Ala Leu Arg Gly Ser Arg Lys Phe
            370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
            405                 410                 415

Arg Cys Gly Asn Arg Gly Arg Ala Asn Cys Asp Ala Ser Leu Ile Val
            420                 425                 430

Thr Glu Glu Leu His Leu Ile Thr Phe Glu Thr Glu Val Tyr His Gln
```

```
                    435                 440                 445
Gly Leu Lys Ile Asp Leu Glu Thr His Ser Leu Pro Val Val Ile
    450                 455                 460
Ser Asn Ile Cys Gln Met Pro Asn Ala Trp Ala Ser Ile Leu Trp Tyr
465                 470                 475                 480
Asn Met Leu Thr Asn Asn Pro Lys Asn Val Asn Phe Phe Thr Lys Pro
                    485                 490                 495
Pro Ile Gly Thr Trp Asp Gln Val Ala Glu Val Leu Ser Trp Gln Phe
                500                 505                 510
Ser Ser Thr Thr Lys Arg Gly Leu Ser Ile Glu Gln Leu Thr Thr Leu
                515                 520                 525
Ala Glu Lys Leu Leu Gly Pro Gly Val Asn Tyr Ser Gly Cys Gln Ile
    530                 535                 540
Thr Trp Ala Lys Phe Cys Lys Glu Asn Met Ala Gly Lys Gly Phe Ser
545                 550                 555                 560
Phe Trp Val Trp Leu Asp Asn Ile Ile Asp Leu Val Lys Lys Tyr Ile
                565                 570                 575
Leu Ala Leu Trp Asn Glu Gly Tyr Ile Met Gly Phe Ile Ser Lys Glu
                580                 585                 590
Arg Glu Arg Ala Ile Leu Ser Thr Lys Pro Pro Gly Thr Phe Leu Leu
    595                 600                 605
Arg Phe Ser Glu Ser Ser Lys Glu Gly Gly Val Thr Phe Thr Trp Val
610                 615                 620
Glu Lys Asp Ile Ser Gly Lys Thr Gln Ile Gln Ser Val Glu Pro Tyr
625                 630                 635                 640
Thr Lys Gln Gln Leu Asn Asn Met Ser Phe Ala Glu Ile Ile Met Gly
                645                 650                 655
Tyr Lys Ile Met Asp Ala Thr Asn Ile Leu Val Ser Pro Leu Val Tyr
                660                 665                 670
Leu Tyr Pro Asp Ile Pro Lys Glu Ala Phe Gly Lys Tyr Cys Arg
    675                 680                 685
Pro Glu Ser Gln Glu His Pro Glu Ala Asp Pro Gly Ser Ala Ala Pro
    690                 695                 700
Tyr Leu Lys Thr Lys Phe Ile Cys Val Thr Pro Thr Thr Cys Ser Asn
705                 710                 715                 720
Thr Ile Asp Leu Pro Met Ser Pro Arg Thr Leu Asp Ser Leu Met Gln
                725                 730                 735
Phe Gly Asn Asn Gly Glu Gly Ala Glu Pro Ser Ala Gly Gly Gln Phe
                740                 745                 750
Glu Ser Leu Thr Phe Asp Met Glu Leu Thr Ser Glu Cys Ala Thr Ser
                755                 760                 765
Pro Met
    770

<210> SEQ ID NO 47
<211> LENGTH: 770
<212> TYPE: PRT
<213> ORGANISM: Artificial Sequence
<220> FEATURE:
<223> OTHER INFORMATION: Synthesized

<400> SEQUENCE: 47

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
```

```
            20                  25                  30
Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
            130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
            195                 200                 205

Ala Leu Asp Gln Met Arg Arg Ser Ile Val Ser Glu Leu Ala Gly Leu
            210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
            275                 280                 285

Gln Lys Val Ser Tyr Lys Gly Asp Pro Ile Val Gln His Arg Pro Met
            290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val His Phe Thr Thr Lys Val Arg Leu Leu
            340                 345                 350

Val Lys Phe Pro Glu Leu Asn Tyr Gln Leu Lys Ile Lys Val Cys Ile
            355                 360                 365

Asp Lys Asp Ser Gly Asp Val Ala Ala Leu Arg Gly Ser Arg Lys Phe
            370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
            405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
            435                 440                 445
```

```
Gly Leu Lys Ile Asp Leu Glu Thr His Ser Leu Pro Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
    595                 600                 605

Arg Phe Ser Glu Ser Ser Lys Glu Gly Gly Val Thr Phe Thr Trp Val
610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
    675                 680                 685

Pro Glu Ser Gln Glu His Pro Glu Ala Asp Pro Gly Ser Ala Ala Pro
690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
    755                 760                 765

Pro Met
    770

<210> SEQ ID NO 48
<211> LENGTH: 770
<212> TYPE: PRT
<213> ORGANISM: Artificial Sequence
<220> FEATURE:
<223> OTHER INFORMATION: Synthesized

<400> SEQUENCE: 48

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30
```

```
Phe Leu Ala Pro Trp Ile Glu Ser Gln Asp Trp Ala Tyr Ala Ala Ser
             35                  40                  45

Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
        130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Lys Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445
```

-continued

```
Gly Leu Lys Ile Asp Leu Glu Thr His Ser Leu Pro Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                    485                 490                 495

Pro Ile Gly Thr Trp Asp Gln Val Ala Glu Val Leu Ser Trp Gln Phe
                500                 505                 510

Ser Ser Thr Thr Lys Arg Gly Leu Ser Ile Glu Gln Leu Thr Thr Leu
                515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
                595                 600                 605

Arg Phe Ser Glu Ser Ser Lys Glu Gly Gly Val Thr Phe Thr Trp Val
610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                    645                 650                 655

Tyr Lys Ile Met Asp Ala Thr Asn Ile Leu Val Ser Pro Leu Val Tyr
                660                 665                 670

Leu Tyr Pro Asp Ile Pro Lys Glu Glu Ala Phe Gly Lys Tyr Cys Arg
                675                 680                 685

Pro Glu Ser Gln Glu His Pro Glu Ala Asp Pro Gly Ser Ala Ala Pro
                690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                    725                 730                 735

Phe Gly Asn Asn Gly Glu Gly Ala Glu Pro Ser Ala Gly Gly Gln Phe
                740                 745                 750

Glu Ser Leu Thr Phe Asp Met Glu Leu Thr Ser Glu Cys Ala Thr Ser
                755                 760                 765

Pro Met
    770
```

<210> SEQ ID NO 49
<211> LENGTH: 770
<212> TYPE: PRT
<213> ORGANISM: Artificial Sequence
<220> FEATURE:
<223> OTHER INFORMATION: Synthesized

<400> SEQUENCE: 49

```
Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
                20                  25                  30
```

```
Phe Leu Ala Pro Trp Ile Glu Ser Gln Asp Trp Ala Tyr Ala Ala Ser
             35                  40                  45
Lys Glu Ser His Ala Thr Leu Val Phe His Asn Leu Leu Gly Glu Ile
 50                  55                  60
Asp Gln Gln Tyr Ser Arg Phe Leu Gln Glu Ser Asn Val Leu Tyr Gln
 65                  70                  75                  80
His Asn Leu Arg Arg Ile Lys Gln Phe Leu Gln Ser Arg Tyr Leu Glu
                 85                  90                  95
Lys Pro Met Glu Ile Ala Arg Ile Val Ala Arg Cys Leu Trp Glu Glu
                100                 105                 110
Ser Arg Leu Leu Gln Thr Ala Ala Thr Ala Ala Gln Gln Gly Gly Gln
                115                 120                 125
Ala Asn His Pro Thr Ala Ala Val Val Thr Glu Lys Gln Gln Met Leu
    130                 135                 140
Glu Gln His Leu Gln Asp Val Trp Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
                180                 185                 190
Gln Ser Val Thr Arg Gln Lys Met Gln Gln Leu Glu Gln Met Leu Thr
    195                 200                 205
Ala Leu Asp Gln Met Arg Arg Ser Ile Val Ser Glu Leu Ala Gly Leu
210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
                260                 265                 270
Ser Gln Leu Gln Thr Arg Gln Gln Ile Lys Lys Leu Glu Glu Leu Gln
    275                 280                 285
Gln Lys Val Ser Tyr Lys Gly Asp Pro Ile Val Gln His Arg Pro Met
290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
                340                 345                 350
Val Lys Phe Pro Glu Leu Asn Tyr Gln Leu Lys Ile Lys Val Cys Ile
                355                 360                 365
Asp Lys Asp Ser Gly Asp Val Ala Ala Leu Arg Gly Ser Arg Lys Phe
    370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
                420                 425                 430
Thr Glu Glu Leu His Leu Ile Thr Phe Glu Thr Glu Val Tyr His Gln
    435                 440                 445
Gly Leu Lys Ile Asp Leu Glu Thr His Ser Leu Pro Val Val Val Ile
```

```
                450             455             460
Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
                500                 505                 510

Ser Ser Thr Thr Lys Arg Gly Leu Ser Ile Glu Gln Leu Thr Thr Leu
                515                 520                 525

Ala Glu Lys Leu Leu Gly Pro Gly Val Asn Tyr Ser Gly Cys Gln Ile
            530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
            610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
                660                 665                 670

Leu Tyr Pro Asp Ile Pro Lys Glu Ala Phe Gly Lys Tyr Cys Arg
            675                 680                 685

Pro Glu Ser Gln Glu His Pro Glu Ala Asp Pro Gly Ser Ala Ala Pro
            690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
                740                 745                 750

Glu Ser Leu Thr Phe Asp Met Glu Leu Thr Ser Glu Cys Ala Thr Ser
            755                 760                 765

Pro Met
    770

<210> SEQ ID NO 50
<211> LENGTH: 770
<212> TYPE: PRT
<213> ORGANISM: Artificial Sequence
<220> FEATURE:
<223> OTHER INFORMATION: Synthesized

<400> SEQUENCE: 50

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
```

```
            35                  40                  45
Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Ala Gln Gln Gly Gly Gln
                115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
                180                 185                 190

Gln Ser Val Thr Arg Gln Lys Met Gln Gln Leu Glu Gln Met Leu Thr
                195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
                260                 265                 270

Ser Gln Leu Gln Thr Arg Gln Gln Ile Lys Lys Leu Glu Glu Leu Gln
                275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
                355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
                420                 425                 430

Thr Glu Glu Leu His Leu Ile Thr Phe Glu Thr Glu Val Tyr His Gln
                435                 440                 445

Gly Leu Lys Ile Asp Leu Glu Thr His Ser Leu Pro Val Val Val Ile
    450                 455                 460
```

```
Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
690                 695                 700

Tyr Leu Lys Thr Lys Phe Ile Cys Val Thr Pro Met Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met
    770

<210> SEQ ID NO 51
<211> LENGTH: 770
<212> TYPE: PRT
<213> ORGANISM: Artificial Sequence
<220> FEATURE:
<223> OTHER INFORMATION: Synthesized

<400> SEQUENCE: 51

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45
```

```
Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Gln Gln Gly Gly Gln
            115                 120                 125

Ala Asn His Pro Thr Ala Ala Val Val Thr Glu Lys Gln Gln Met Leu
        130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Lys Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460
```

```
Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
                500                 505                 510

Ser Ser Thr Thr Lys Arg Gly Leu Ser Ile Glu Gln Leu Thr Thr Leu
                515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
    595                 600                 605

Arg Phe Ser Glu Ser Ser Lys Glu Gly Gly Val Thr Phe Thr Trp Val
610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
                660                 665                 670

Leu Tyr Pro Asp Ile Pro Lys Glu Glu Ala Phe Gly Lys Tyr Cys Arg
                675                 680                 685

Pro Glu Ser Gln Glu His Pro Glu Ala Asp Pro Gly Ser Ala Ala Pro
                690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
                740                 745                 750

Glu Ser Leu Thr Phe Asp Met Glu Leu Thr Ser Glu Cys Ala Thr Ser
                755                 760                 765

Pro Met
    770

<210> SEQ ID NO 52
<211> LENGTH: 770
<212> TYPE: PRT
<213> ORGANISM: Artificial Sequence
<220> FEATURE:
<223> OTHER INFORMATION: Synthesized

<400> SEQUENCE: 52

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
                20                  25                  30

Phe Leu Ala Pro Trp Ile Glu Ser Gln Asp Trp Ala Tyr Ala Ala Ser
                35                  40                  45
```

-continued

```
Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Gln Gln Gly Gly Gln
        115                 120                 125

Ala Asn His Pro Thr Ala Ala Val Val Thr Glu Lys Gln Gln Met Leu
130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Phe Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
450                 455                 460

Ser Asn Ile Cys Gln Met Pro Asn Ala Trp Ala Ser Ile Leu Trp Tyr
```

```
                    465                 470                 475                 480
Asn Met Leu Thr Asn Asn Pro Lys Asn Val Asn Phe Phe Thr Lys Pro
                    485                 490                 495
Pro Ile Gly Thr Trp Asp Gln Val Ala Glu Val Leu Ser Trp Gln Phe
                500                 505                 510
Ser Ser Thr Thr Lys Arg Gly Leu Ser Ile Glu Gln Leu Thr Thr Leu
            515                 520                 525
Ala Glu Lys Leu Leu Gly Pro Gly Val Asn Tyr Ser Gly Cys Gln Ile
        530                 535                 540
Thr Trp Ala Lys Phe Cys Lys Glu Asn Met Ala Gly Lys Gly Phe Ser
545                 550                 555                 560
Phe Trp Val Trp Leu Asp Asn Ile Ile Asp Leu Val Lys Lys Tyr Ile
                565                 570                 575
Leu Ala Leu Trp Asn Glu Gly Tyr Ile Met Gly Phe Ile Ser Lys Glu
                580                 585                 590
Arg Glu Arg Ala Ile Leu Ser Thr Lys Pro Pro Gly Thr Phe Leu Leu
                595                 600                 605
Arg Phe Ser Glu Ser Ser Lys Glu Gly Gly Val Thr Phe Thr Trp Val
            610                 615                 620
Glu Lys Asp Ile Ser Gly Lys Thr Gln Ile Gln Ser Val Glu Pro Tyr
625                 630                 635                 640
Thr Lys Gln Gln Leu Asn Asn Met Ser Phe Ala Glu Ile Ile Met Gly
                645                 650                 655
Tyr Lys Ile Met Asp Ala Thr Asn Ile Leu Val Ser Pro Leu Val Tyr
                660                 665                 670
Leu Tyr Pro Asp Ile Pro Lys Glu Glu Ala Phe Gly Lys Tyr Cys Arg
                675                 680                 685
Pro Glu Ser Gln Glu His Pro Glu Ala Asp Pro Gly Ser Ala Ala Pro
            690                 695                 700
Tyr Leu Lys Thr Lys Phe Ile Cys Val Thr Pro Thr Thr Cys Ser Asn
705                 710                 715                 720
Thr Ile Asp Leu Pro Met Ser Pro Arg Thr Leu Asp Ser Leu Met Gln
                725                 730                 735
Phe Gly Asn Asn Gly Glu Gly Ala Glu Pro Ser Ala Gly Gly Gln Phe
                740                 745                 750
Glu Ser Leu Thr Phe Asp Met Glu Leu Thr Ser Glu Cys Ala Thr Ser
            755                 760                 765
Pro Met
    770

<210> SEQ ID NO 53
<211> LENGTH: 748
<212> TYPE: PRT
<213> ORGANISM: Homo sapiens

<400> SEQUENCE: 53

Met Ser Gln Trp Asn Gln Val Gln Gln Leu Glu Ile Lys Phe Leu Glu
1               5                   10                  15
Gln Val Asp Gln Phe Tyr Asp Asp Asn Phe Pro Met Glu Ile Arg His
                20                  25                  30
Leu Leu Ala Gln Trp Ile Glu Asn Gln Asp Trp Glu Ala Ala Ser Asn
            35                  40                  45
Asn Glu Thr Met Ala Thr Ile Leu Leu Gln Asn Leu Leu Ile Gln Leu
        50                  55                  60
```

-continued

```
Asp Glu Gln Leu Gly Arg Val Ser Lys Glu Lys Asn Leu Leu Leu Ile
 65                  70                  75                  80

His Asn Leu Lys Arg Ile Arg Lys Val Leu Gln Gly Lys Phe His Gly
                 85                  90                  95

Asn Pro Met His Val Ala Val Val Ile Ser Asn Cys Leu Arg Glu Glu
            100                 105                 110

Arg Arg Ile Leu Ala Ala Ala Asn Met Pro Val Gln Gly Pro Leu Glu
        115                 120                 125

Lys Ser Leu Gln Ser Ser Ser Val Ser Glu Arg Gln Arg Asn Val Glu
    130                 135                 140

His Lys Val Ala Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Ser Asp Lys Asn Ser Ala Met Val Asn
            180                 185                 190

Gln Glu Val Leu Thr Leu Gln Glu Met Leu Asn Ser Leu Asp Phe Lys
        195                 200                 205

Arg Lys Glu Ala Leu Ser Lys Met Thr Gln Ile Ile His Glu Thr Asp
    210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
                245                 250                 255

Gln Leu Gln Asn Cys Phe Thr Leu Leu Ala Glu Ser Leu Phe Gln Leu
            260                 265                 270

Arg Arg Gln Leu Glu Lys Leu Glu Glu Gln Ser Thr Lys Met Thr Tyr
        275                 280                 285

Glu Gly Asp Pro Ile Pro Met Gln Arg Thr His Met Leu Glu Arg Val
    290                 295                 300

Thr Phe Leu Ile Tyr Asn Leu Phe Lys Asn Ser Phe Val Val Glu Arg
305                 310                 315                 320

Gln Pro Cys Met Pro Thr His Pro Gln Arg Pro Leu Val Leu Lys Thr
                325                 330                 335

Leu Ile Gln Phe Thr Val Lys Leu Arg Leu Leu Ile Lys Leu Pro Glu
            340                 345                 350

Leu Asn Tyr Gln Val Lys Val Lys Ala Ser Ile Asp Lys Asn Val Ser
        355                 360                 365

Thr Leu Ser Asn Arg Arg Phe Val Leu Cys Gly Thr Asn Val Lys Ala
    370                 375                 380

Met Ser Ile Glu Glu Ser Ser Asn Gly Ser Leu Ser Val Glu Phe Arg
385                 390                 395                 400

His Leu Gln Pro Lys Glu Met Lys Ser Ser Ala Gly Lys Gly Asn
                405                 410                 415

Glu Gly Cys His Met Val Thr Glu Glu Leu His Ser Ile Thr Phe Glu
            420                 425                 430

Thr Gln Ile Cys Leu Tyr Gly Leu Thr Ile Asp Leu Glu Thr Ser Ser
        435                 440                 445

Leu Pro Val Val Met Ile Ser Asn Val Ser Gln Leu Pro Asn Ala Trp
    450                 455                 460

Ala Ser Ile Ile Trp Tyr Asn Val Ser Thr Asn Asp Ser Gln Asn Leu
465                 470                 475                 480

Val Phe Phe Asn Asn Pro Pro Ala Thr Leu Ser Gln Leu Leu Glu
```

```
            485                 490                 495
Val Met Ser Trp Gln Phe Ser Ser Tyr Val Gly Arg Gly Leu Asn Ser
            500                 505                 510

Asp Gln Leu His Met Leu Ala Glu Lys Leu Thr Val Gln Ser Ser Tyr
        515                 520                 525

Ser Asp Gly His Leu Thr Trp Ala Lys Phe Cys Lys Glu His Leu Pro
    530                 535                 540

Gly Lys Ser Phe Thr Phe Trp Thr Trp Leu Glu Ala Ile Leu Asp Leu
545                 550                 555                 560

Ile Lys Lys His Ile Leu Pro Leu Trp Ile Asp Gly Tyr Val Met Gly
                565                 570                 575

Phe Val Ser Lys Glu Lys Glu Arg Leu Leu Lys Asp Lys Met Pro
            580                 585                 590

Gly Thr Phe Leu Leu Arg Phe Ser Glu Ser His Leu Gly Gly Ile Thr
            595                 600                 605

Phe Thr Trp Val Asp His Ser Glu Ser Gly Glu Val Arg Phe His Ser
    610                 615                 620

Val Glu Pro Tyr Asn Lys Gly Arg Leu Ser Ala Leu Pro Phe Ala Asp
625                 630                 635                 640

Ile Leu Arg Asp Tyr Lys Val Ile Met Ala Glu Asn Ile Pro Glu Asn
                645                 650                 655

Pro Leu Lys Tyr Leu Tyr Pro Asp Ile Pro Lys Asp Lys Ala Phe Gly
            660                 665                 670

Lys His Tyr Ser Ser Gln Pro Cys Glu Val Ser Arg Pro Thr Glu Arg
            675                 680                 685

Gly Asp Lys Gly Tyr Val Pro Ser Val Phe Ile Pro Ile Ser Thr Ile
        690                 695                 700

Arg Ser Asp Ser Thr Glu Pro His Ser Pro Ser Asp Leu Leu Pro Met
705                 710                 715                 720

Ser Pro Ser Val Tyr Ala Val Leu Arg Glu Asn Leu Ser Pro Thr Thr
                725                 730                 735

Ile Glu Thr Ala Met Lys Ser Pro Tyr Ser Ala Glu
            740                 745

<210> SEQ ID NO 54
<211> LENGTH: 748
<212> TYPE: PRT
<213> ORGANISM: Artificial Sequence
<220> FEATURE:
<223> OTHER INFORMATION: Synthesized

<400> SEQUENCE: 54

Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
            20                  25                  30

Leu Leu Ala Gln Trp Ile Glu Asn Gln Asp Trp Glu Ala Ala Ser Asn
        35                  40                  45

Asn Glu Thr Met Ala Thr Ile Leu Leu Gln Asn Leu Leu Ile Gln Leu
    50                  55                  60

Asp Glu Gln Leu Gly Arg Val Ser Lys Glu Lys Asn Leu Leu Leu Ile
65                  70                  75                  80

His Asn Leu Lys Arg Ile Arg Lys Val Leu Gln Gly Lys Phe His Gly
                85                  90                  95

Asn Pro Met His Val Ala Val Val Ile Ser Asn Cys Leu Arg Glu Glu
```

-continued

```
                100                 105                 110
Arg Arg Ile Leu Ala Ala Ala Asn Met Pro Val Gln Gly Pro Leu Glu
            115                 120                 125

Lys Ser Leu Gln Ser Ser Val Ser Glu Arg Gln Arg Asn Val Glu
130                 135                 140

His Lys Val Ala Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Ser Asp Lys Asn Ser Ala Met Val Asn
            180                 185                 190

Gln Glu Val Leu Thr Leu Gln Glu Met Leu Asn Ser Leu Asp Phe Lys
            195                 200                 205

Arg Lys Glu Ala Leu Ser Lys Met Thr Gln Ile Ile His Glu Thr Asp
210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
                245                 250                 255

Gln Leu Gln Asn Cys Phe Thr Leu Leu Ala Glu Ser Leu Phe Gln Leu
            260                 265                 270

Arg Arg Gln Leu Glu Lys Leu Glu Glu Gln Ser Thr Lys Met Thr Tyr
            275                 280                 285

Glu Gly Asp Pro Ile Pro Met Gln Arg Thr His Met Leu Glu Arg Val
            290                 295                 300

Thr Phe Leu Ile Tyr Asn Leu Phe Lys Asn Ser Phe Val Val Glu Arg
305                 310                 315                 320

Gln Pro Cys Met Pro Thr His Pro Gln Arg Pro Leu Val Leu Lys Thr
                325                 330                 335

Leu Ile Gln Phe Thr Val Lys Leu Arg Leu Leu Ile Lys Leu Pro Glu
            340                 345                 350

Leu Asn Tyr Gln Val Lys Val Lys Ala Ser Ile Asp Lys Asn Val Ser
            355                 360                 365

Thr Leu Ser Asn Arg Arg Phe Val Leu Cys Gly Thr Asn Val Lys Ala
370                 375                 380

Met Ser Ile Glu Glu Ser Ser Asn Gly Ser Leu Ser Val Glu Phe Arg
385                 390                 395                 400

His Leu Gln Pro Lys Glu Met Lys Ser Ser Ala Gly Gly Lys Gly Asn
                405                 410                 415

Glu Gly Cys His Met Val Thr Glu Glu Leu His Ser Ile Thr Phe Glu
            420                 425                 430

Thr Gln Ile Cys Leu Tyr Gly Leu Thr Ile Asp Leu Glu Thr Ser Ser
            435                 440                 445

Leu Pro Val Val Met Ile Ser Asn Val Ser Gln Leu Pro Asn Ala Trp
            450                 455                 460

Ala Ser Ile Ile Trp Tyr Asn Val Ser Thr Asn Asp Ser Gln Asn Leu
465                 470                 475                 480

Val Phe Phe Asn Asn Pro Pro Ala Thr Leu Ser Gln Leu Leu Glu
                485                 490                 495

Val Met Ser Trp Gln Phe Ser Ser Tyr Val Gly Arg Gly Leu Asn Ser
            500                 505                 510

Asp Gln Leu His Met Leu Ala Glu Lys Leu Thr Val Gln Ser Ser Tyr
            515                 520                 525
```

```
Ser Asp Gly His Leu Thr Trp Ala Lys Phe Cys Lys Glu His Leu Pro
        530                 535                 540

Gly Lys Ser Phe Thr Phe Trp Thr Trp Leu Glu Ala Ile Leu Asp Leu
545                 550                 555                 560

Ile Lys Lys His Ile Leu Pro Leu Trp Ile Asp Gly Tyr Val Met Gly
                565                 570                 575

Phe Val Ser Lys Glu Lys Glu Arg Leu Leu Lys Asp Lys Met Pro
        580                 585                 590

Gly Thr Phe Leu Leu Arg Phe Ser Glu Ser His Leu Gly Gly Ile Thr
        595                 600                 605

Phe Thr Trp Val Asp His Ser Glu Ser Gly Glu Val Arg Phe His Ser
        610                 615                 620

Val Glu Pro Tyr Asn Lys Gly Arg Leu Ser Ala Leu Pro Phe Ala Asp
625                 630                 635                 640

Ile Leu Arg Asp Tyr Lys Val Ile Met Ala Glu Asn Ile Pro Glu Asn
                645                 650                 655

Pro Leu Lys Tyr Leu Tyr Pro Asp Ile Pro Lys Asp Lys Ala Phe Gly
                660                 665                 670

Lys His Tyr Ser Ser Gln Pro Cys Glu Val Ser Arg Pro Thr Glu Arg
                675                 680                 685

Gly Asp Lys Gly Asp Val Pro Ser Val Phe Ile Pro Ile Ser Thr Ile
        690                 695                 700

Arg Ser Asp Ser Thr Glu Pro His Ser Pro Ser Asp Leu Leu Pro Met
705                 710                 715                 720

Ser Pro Ser Val Tyr Ala Val Leu Arg Glu Asn Leu Ser Pro Thr Thr
                725                 730                 735

Ile Glu Thr Ala Met Lys Ser Pro Tyr Ser Ala Glu
                740                 745

<210> SEQ ID NO 55
<211> LENGTH: 748
<212> TYPE: PRT
<213> ORGANISM: Artificial Sequence
<220> FEATURE:
<223> OTHER INFORMATION: Synthesized

<400> SEQUENCE: 55

Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
                20                  25                  30

Leu Leu Ala Gln Trp Ile Glu Asn Gln Asp Trp Glu Ala Ala Ser Asn
            35                  40                  45

Asn Glu Thr Met Ala Thr Ile Leu Leu Gln Asn Leu Leu Ile Gln Leu
        50                  55                  60

Asp Glu Gln Leu Gly Arg Val Ser Lys Glu Lys Asn Leu Leu Leu Ile
65                  70                  75                  80

His Asn Leu Lys Arg Ile Arg Lys Val Leu Gln Gly Lys Phe His Gly
                85                  90                  95

Asn Pro Met His Val Ala Val Val Ile Ser Asn Cys Leu Arg Glu Glu
                100                 105                 110

Arg Arg Ile Leu Ala Ala Ala Asn Met Pro Val Gln Gly Pro Leu Glu
            115                 120                 125

Lys Ser Leu Gln Ser Ser Ser Val Ser Glu Arg Gln Arg Asn Val Glu
        130                 135                 140
```

```
His Lys Val Ala Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
            165                 170                 175

Thr Ile Gln Thr Met Asp Gln Ser Asp Lys Asn Ser Ala Met Val Asn
            180                 185                 190

Gln Glu Val Leu Thr Leu Gln Glu Met Leu Asn Ser Leu Asp Phe Lys
            195                 200                 205

Arg Lys Glu Ala Leu Ser Lys Met Thr Gln Ile Ile His Glu Thr Asp
        210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
                245                 250                 255

Gln Leu Gln Asn Cys Phe Thr Leu Leu Ala Glu Ser Leu Phe Gln Leu
            260                 265                 270

Arg Arg Gln Leu Glu Lys Leu Glu Glu Gln Ser Thr Lys Met Thr Tyr
        275                 280                 285

Glu Gly Asp Pro Ile Pro Met Gln Arg Thr His Met Leu Glu Arg Val
        290                 295                 300

Thr Phe Leu Ile Tyr Asn Leu Phe Lys Asn Ser Phe Val Val Glu Arg
305                 310                 315                 320

Gln Pro Cys Met Pro Thr His Pro Gln Arg Pro Leu Val Leu Lys Thr
                325                 330                 335

Leu Ile Gln Phe Thr Val Lys Leu Arg Leu Leu Ile Lys Leu Pro Glu
            340                 345                 350

Leu Asn Tyr Gln Val Lys Val Lys Ala Ser Ile Asp Lys Asn Val Ser
        355                 360                 365

Thr Leu Ser Asn Arg Arg Phe Val Leu Cys Gly Thr Asn Val Lys Ala
    370                 375                 380

Met Ser Ile Glu Glu Ser Ser Asn Gly Ser Leu Ser Val Glu Phe Arg
385                 390                 395                 400

His Leu Gln Pro Lys Glu Met Lys Ser Ser Ala Gly Gly Lys Gly Asn
            405                 410                 415

Glu Gly Cys His Met Val Thr Glu Glu Leu His Ser Ile Thr Phe Glu
            420                 425                 430

Thr Gln Ile Cys Leu Tyr Gly Leu Thr Ile Asp Leu Glu Thr Ser Ser
        435                 440                 445

Leu Pro Val Val Met Ile Ser Asn Val Ser Gln Leu Pro Asn Ala Trp
    450                 455                 460

Ala Ser Ile Ile Trp Tyr Asn Val Ser Thr Asn Asp Ser Gln Asn Leu
465                 470                 475                 480

Val Phe Phe Asn Asn Pro Pro Ala Thr Leu Ser Gln Leu Leu Glu
            485                 490                 495

Val Met Ser Trp Gln Phe Ser Ser Tyr Val Gly Arg Gly Leu Asn Ser
            500                 505                 510

Asp Gln Leu His Met Leu Ala Glu Lys Leu Thr Val Gln Ser Ser Tyr
        515                 520                 525

Ser Asp Gly His Leu Thr Trp Ala Lys Phe Cys Lys Glu His Leu Pro
    530                 535                 540

Gly Lys Ser Phe Thr Phe Trp Thr Trp Leu Glu Ala Ile Leu Asp Leu
545                 550                 555                 560
```

-continued

```
Ile Lys Lys His Ile Leu Pro Leu Trp Ile Asp Gly Tyr Val Met Gly
            565                 570                 575

Phe Val Ser Lys Glu Lys Glu Arg Leu Leu Leu Lys Asp Lys Met Pro
            580                 585                 590

Gly Thr Phe Leu Leu Arg Phe Ser Glu Ser His Leu Gly Gly Ile Thr
            595                 600                 605

Phe Thr Trp Val Asp His Ser Glu Ser Gly Glu Val Arg Phe His Ser
            610                 615                 620

Val Glu Pro Tyr Asn Lys Gly Arg Leu Ser Ala Leu Pro Phe Ala Asp
625                 630                 635                 640

Ile Leu Arg Asp Tyr Lys Val Ile Met Ala Glu Asn Ile Pro Glu Asn
                645                 650                 655

Pro Leu Lys Tyr Leu Tyr Pro Asp Ile Pro Lys Asp Lys Ala Phe Gly
                660                 665                 670

Lys His Tyr Ser Ser Gln Pro Cys Glu Val Ser Arg Pro Thr Glu Arg
                675                 680                 685

Gly Asp Lys Gly Tyr Val Pro Ser Val Phe Ile Pro Ile Ser Thr Ile
            690                 695                 700

Arg Ser Asp Ser Thr Glu Pro His Ser Pro Ser Asp Leu Leu Pro Met
705                 710                 715                 720

Asp Pro Ser Val Tyr Ala Val Leu Arg Glu Asn Leu Ser Pro Thr Thr
                725                 730                 735

Ile Glu Thr Ala Met Lys Ser Pro Tyr Ser Ala Glu
                740                 745
```

MODIFIED CELL AND USE THEREOF IN GENE AND CELL THERAPY

CROSS REFERENCE TO RELATED APPLICATIONS

This application claims the benefit of U.S. Provisional Application 63/086,343, filed Oct. 1, 2020, which is hereby incorporated by reference in its entirety.

SEQUENCE LISTING INFORMATION

A computer readable textfile, entitled "ST25.txt," created on or about Sep. 21, 2021, with a file size of about 41.3 KB, contains the sequence listing for this application and is hereby incorporated by reference in its entirety.

TECHNICAL FIELD

The present disclosure relates to compositions and methods for expanding and maintaining modified cells including genetically modified cells, for example, maintaining the number of modified cells, and uses thereof in the treatment of diseases, including cancer.

BACKGROUND

Chimeric antigen receptor (CAR) T cell therapy made significant progress for treating blood cancer such as leukemia, lymphoma, and myeloma. However, the therapy faces many challenges, such as physical barrier, tumor microenvironment immunosuppression, tumor heterogeneity, target specificity, and cell expansion in vivo for the treatment of solid tumors.

SUMMARY

The present disclosure describes compositions and methods for treating cancer. Embodiments relate to a cell modified to express one or more molecules at a level that is higher or lower than the level of the one or more molecules expressed by a cell that has not been modified to express the one or more molecules, wherein the one or more molecules are identified in single-cell profiling analysis. Embodiments relate to a modified cell engineered to express an antigen binding molecule, wherein the expression and/or function of one or more molecules in the modified cell has been enhanced or reduced (including eliminated), where the one or more molecules are identified in single-cell profiling analysis. In embodiments, the modified cell comprises a disruption in an endogenous gene or addition of an exogenous gene that is associated with a biosynthesis or transportation pathway of one or more molecules. In embodiments, the one more molecules comprise at least one of JAK2, STAT1, STAT2, STAT3, STAT4, PRKCA, PRKCQ, MAP3K1, MAP3K4, MAP3K8, MAPK14, BRAF, SMAD5, IL2RB, IL12RB2, IL18R1, IL21R, IL7R, CD28, Cavin3, ZBED2, MYC, EGFR, HER2, HER3, HER4, VEGFR2, VEGFR3, PDGFRα, PDGFRβ, gp130, IL-23R, IL-7R, CRLF2, βc, GHR, THPOR, EPOR, LepR, CSF3R, TNFR1, TGFBR1, TGFBR2, ACVR1A, BMPR2 ACVR1B, CXCR1, CXCR2, CXCR3, CXCR4, CCR2, CCR5, TOX, TOX2, TOX4, NR4A2, NR4A3, a functional variant of the one or more molecules, or a functional fragment of the one or more molecules. The one or more molecules can be overexpressed or inducibly overexpressed.

Embodiments relate to a cell modified to express one or more molecules at a level that is higher or lower than the level of the one or more molecules expressed by a cell that has not been modified to express the one or more molecules, wherein the one or more molecules comprise at least one of Cavin3, ZBED2, and MYC This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIGS. 13A, 13B, 13C, and 13D show histograms of results of flow cytometry analysis of expression of various markers on T cells and B cells in experiments described in FIG. 12.

FIG. 23 shows highly expressed genes in PAP CAR T cells in TC1.

FIGS. 26A, 26B, and 26C show that TSHR CAR T cells are significantly enriched in tumor tissue, confirming the capacity of CAR T cell infiltration into the tumor. These data are restricted to just TSHR CAR T cells.

FIGS. 27A, 27B, 27C, and 27D show rare clonotype was found to be shared by TSHR CAR T cells in PB and tumor tissue.

DETAILED DESCRIPTION

Figure 1:
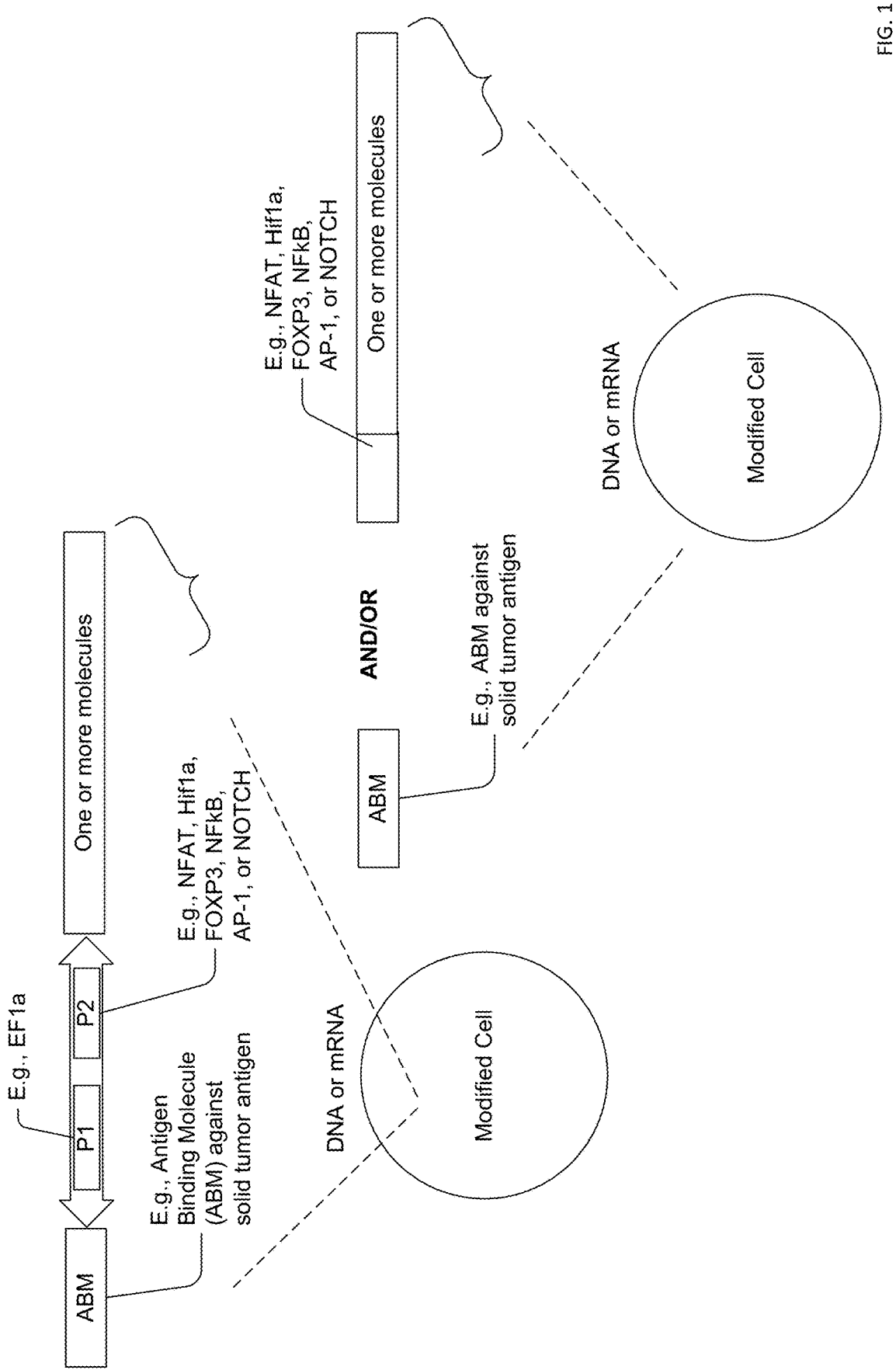
FIG. 1 shows schematic examples of modified cells.
Figure 2:
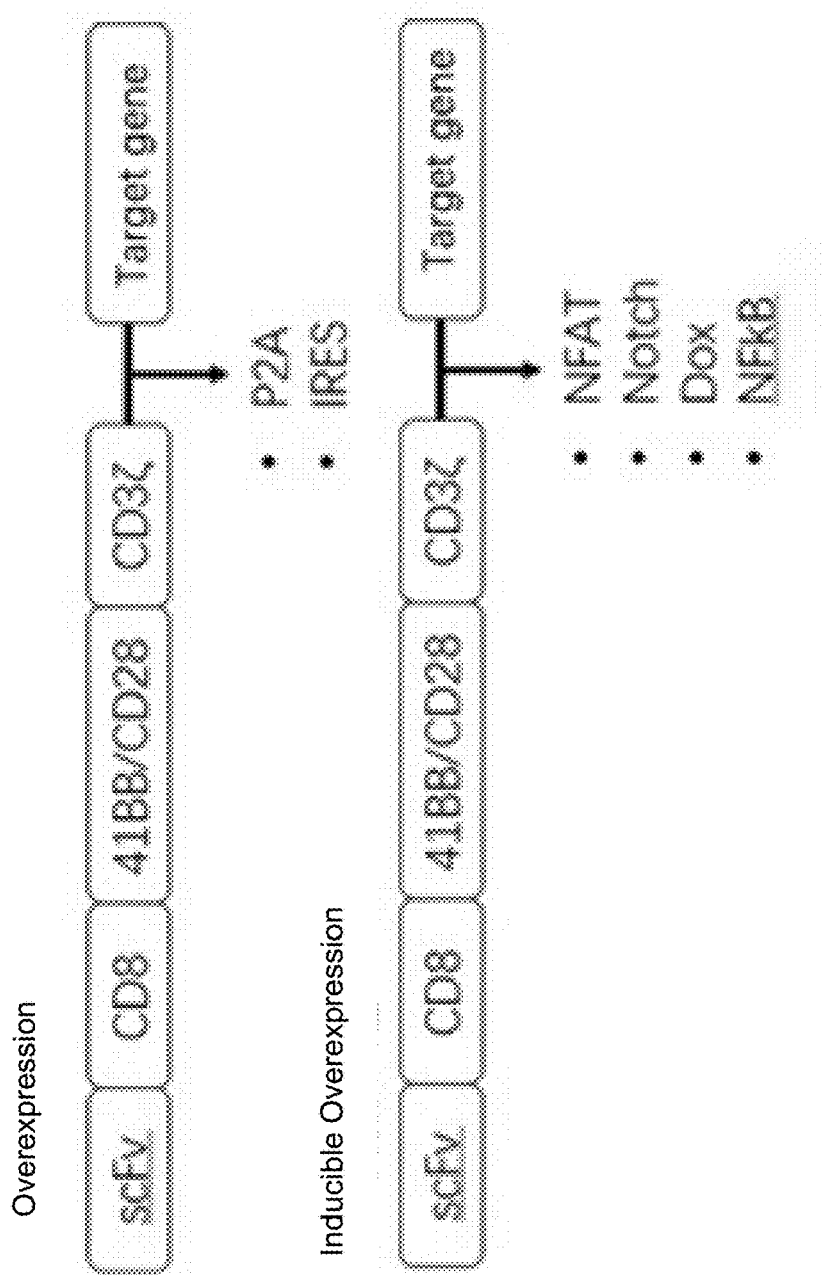
FIG. 2 shows schematic examples of constructs with respect to the embodiments described in FIG. 1.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multispecific antibodies (e.g., bispecific antibodies), and antibody fragments so long as they exhibit the desired biological activity or function. The antibodies in the present disclosure may exist in a variety of forms including, for example, polyclonal antibodies; monoclonal antibodies; Fv, Fab, Fab', and F(ab')$_2$ fragments; as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragments" refers to a portion of a full-length antibody, for example, the antigen binding or variable region of the antibody. Other examples of antibody fragments include Fab, Fab', F(ab')$_2$, and Fv fragments; diabodies; linear antibodies; single-chain antibody molecules; and multispecific antibodies formed from antibody fragments.

The term "Fv" refers to the minimum antibody fragment, which contains a complete antigen-recognition and -binding site. This fragment consists of a dimer of one heavy- and one light-chain variable region domain in a tight, non-covalent association. From the folding of these two domains emanates six hypervariable loops (3 loops each from the H and L chain) that contribute amino acid residues for antigen binding and confer antigen binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and λ light chains refer to the two major antibody light chain isotypes.

The term "synthetic antibody" refers to an antibody that is generated using recombinant DNA technology, such as, for example, an antibody expressed by a bacteriophage. The term also includes an antibody that has been generated by the synthesis of a DNA molecule encoding the antibody and the expression of the DNA molecule to obtain the antibody or to obtain an amino acid encoding the antibody. Synthetic DNA is obtained using technology that is available and well known in the art.

The term "antigen" refers to a molecule that provokes an immune response, which may involve either antibody production, or the activation of specific immunologically competent cells, or both. Antigens include any macromolecule, including all proteins or peptides or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized, or derived from a biological sample including a tissue sample, a tumor sample, a cell, or a biological fluid.

The term "anti-tumor effect," as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an endogenous antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject that is subsequently re-introduced into the same subject.

The term "allogeneic" is used to describe a graft derived from a different subject of the same species. As an example, a donor subject may be related or unrelated to the recipient subject, but the donor subject has immune system markers which are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" is used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes," and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. For example, if the element does not affect the expansion, function, or phenotype of the cells, then the element is not required and is considered optional.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein, or (b) a peptide or polypeptide having an amino acid sequence that is substantially identical to a sequence of amino acids in a reference peptide or protein.

The term "co-stimulatory ligand" refers to a molecule on an antigen-presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor, and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated, then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression or overexpression" refers to the transcription and/or translation of a particular nucleotide sequence into a precursor or mature protein, for example, driven by its promoter. "Overexpression" refers to the production of a gene product in transgenic organisms or cells that exceeds levels of production in normal or non-transformed organisms or cells. As defined herein, the term "expression" refers to expression or overexpression.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses) that incorporate the recombinant polynucleotide.

Viruses can be used to deliver nucleic acids into a cell in vitro and in vivo (in a subject). Examples of viruses useful for delivery of nucleic acids into cells include retrovirus, adenovirus, herpes simplex virus, vaccinia virus, and adeno-associated virus.

There also exist non-viral methods for delivering nucleic acids into a cell, for example, electroporation, gene gun, sonoporation, magnetofection, and the use of oligonucleotides, lipoplexes, dendrimers, and inorganic nanoparticles.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions, and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule, such as a protein or nucleic acid. For example, an "isolated polynucleotide," as used herein, refers to a polynucleotide, which has been purified from the sequences which flank it in a naturally-occurring state, e.g., a DNA fragment that has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some versions contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables the integration of genetic information into the host chromosome, resulting in stably transduced genetic information. HIV, SIV, and FIV are all examples of lentiviruses. Vectors derived from lentiviruses offer the means to achieve significant levels of gene transfer in vivo.

The term "modulating" refers to mediating a detectable increase or decrease in the level of a response in a subject compared with the level of a response in the subject in the absence of a treatment or compound and/or compared with the level of a response in an otherwise identical but untreated subject. The term encompasses perturbing and/or affecting a native signal or response, thereby mediating a beneficial therapeutic response in a subject, preferably a human.

Nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence, or a ribosome binding site is operably linked to a coding sequence if it is positioned so as to facilitate translation.

The term "under transcriptional control" refers to a promoter being operably linked to and in the correct location and orientation in relation to a polynucleotide to control (regulate) the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having a solid tumor or a hematological malignancy characterized by overexpression of the tumor antigen can be determined by standard assays known in the art.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
|---|---|
| PRLR | Breast Cancer |
| CLCA1 | colorectal Cancer |
| MUC12 | colorectal Cancer |
| GUCY2C | colorectal Cancer and other digestive cancer types |
| GPR35 | colorectal Cancer |
| CR1L | Gastric Cancer |
| MUC 17 | Gastric Cancer |
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer, and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesotelioma |
| GPC3 | Lung squamous cell carcinoma |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomas |
| EpCAM | Carcinomas |
| EGFRvIII | Glioma-Glioblastoma |

TABLE 1-continued

| Solid Tumor antigen | Disease tumor |
| --- | --- |
| EGFR | Glioma-NSCL cancer |
| tMUC1 | Cholangiocarcinoma, Pancreatic cancer, Breast |
| PSCA | pancreas, stomach, or prostate cancer |
| FCER2, GPR18, FCRLA, CXCR5, FCRL3, FCRL2, HTR3A, and CLEC17A | breast cancer |
| TRPMI, SLC45A2, and SLC24A5 | Lymphoma |
| DPEP3 | Melanoma |
| KCNK16 | ovarian, testis |
| LIM2 or KCNV2 | Pancreatic |
| SLC26A4 | thyroid cancer |
| CD171 | Neuroblastoma |
| Glypican-3 | Sarcoma |
| IL-13 | Glioma |
| CD79a/b | Lymphoma |
| MAGE A4 | Lung cancer and multiple cancer types |

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein and refer to any human or animal, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals, such as dogs, cats, mice, rats, and transgenic species thereof.

A subject in need of treatment or in need thereof includes a subject having a disease, condition, or disorder that needs to be treated. A subject in need thereof also includes a subject that needs treatment for the prevention of a disease, condition, or disorder.

The term "polynucleotide" or "nucleic acid" refers to mRNA, RNA, cRNA, rRNA, cDNA, or DNA. The term typically refers to a polymeric form of nucleotides of at least 10 bases in length, either ribonucleotides or deoxynucleotides, or a modified form of either type of nucleotide. The term includes all forms of nucleic acids, including single and double-stranded forms of nucleic acids.

The terms "polynucleotide variant" and "variant," and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions, and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The term "promoter" refers to a DNA sequence recognized by the synthetic machinery of the cell or introduced synthetic machinery required to initiate the specific transcription of a polynucleotide sequence. The term "expression control (regulatory) sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody that recognizes a specific antigen but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding" can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

By "statistically significant," it is meant that the result was unlikely to have occurred by chance. Statistical significance can be determined by any method known in art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation" refers to a primary response induced by binding of a stimulatory molecule (e.g., a TCR/CD3 complex) with its cognate ligand, thereby mediating a signal transduction event, such as signal transduction via the TCR/CD3 complex. Stimulation can mediate altered expression of certain molecules, such as downregulation of TGF-β and/or reorganization of cytoskeletal structures.

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen-presenting cell (e.g., an APC, a dendritic cell, a B-cell, and the like.) can specifically bind with a cognate binding partner (referred to herein as a "stimulatory molecule") on a cell, for example, a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease, and its severity, and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one that has been transfected, transformed, or transduced with an exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate the transfer of nucleic acid into cells, such as, for example, polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural functions. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted, making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

A "chimeric antigen receptor" (CAR) molecule is a recombinant polypeptide including at least an extracellular domain, a transmembrane domain, and a cytoplasmic domain or intracellular domain. In embodiments, the domains of the CAR are on the same polypeptide chain, for example, a chimeric fusion protein. In embodiments, the domains are on different polypeptide chains, for example, the domains are not contiguous.

The extracellular domain of a CAR molecule includes an antigen binding domain. The antigen binding domain is for expanding and/or maintaining the modified cells, such as a CAR T cell, or for killing a tumor cell, such as a solid tumor. In embodiments, the antigen binding domain for expanding and/or maintaining modified cells binds an antigen, for example, a cell surface molecule or marker, on the surface of a WBC. In embodiments, the WBC is at least one of GMP (granulocyte macrophage precursor), MDP (monocyte-macrophage/dendritic cell precursors), cMoP (common monocyte precursor), basophil, eosinophil, neutrophil, SatM (Segerate-nucleus-containing atypical monocyte), macrophage, monocyte, CDP (common dendritic cell precursor), cDC (conventional DC), pDC (plasmacytoid DC), CLP (common lymphocyte precursor), B cell, ILC (Innate Lymphocyte), NK cell, megakaryocyte, myeloblast, promyelocyte, myelocyte, meta—myelocyte, band cells, lymphoblast, prolymphocyte, monoblast, megakaryoblast, promegakaryocyte, megakaryocyte, platelets, or MSDC (Myeloid-derived suppressor cell). In embodiments, the WBC is a granulocyte, monocyte, and or lymphocyte. In embodiments, the WBC is a lymphocyte, for example, a B cell. In embodiments, the WBC is a B cell. In embodiments, the cell surface molecule of a B cell includes CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the B cell is CD19, CD20, CD22, or BCMA. In embodiments, the cell surface molecule of the B cell is CD19.

The cells described herein, including modified cells such as CAR cells and modified T cells, can be derived from stem cells. Stem cells may be adult stem cells, embryonic stem cells, more particularly non-human stem cells, cord blood stem cells, progenitor cells, bone marrow stem cells, induced pluripotent stem cells, totipotent stem cells, or hematopoietic stem cells. A modified cell may also be a dendritic cell, an NK-cell, a B-cell, or a T cell selected from the group consisting of inflammatory T-lymphocytes, cytotoxic T-lymphocytes, regulatory T lymphocytes, or helper T-lymphocytes. In embodiments, Modified cells may be derived from the group consisting of CD4+ T lymphocytes and CD8+ T lymphocytes. Prior to expansion and genetic modification of the cells, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art may be used. In embodiments, modified cells may be derived from a healthy donor, from a patient diagnosed with cancer, or from a patient diagnosed with an infection. In embodiments, a modified cell is part of a mixed population of cells that present different phenotypic characteristics.

A population of cells refers to a group of two or more cells. The cells of the population could be the same, such that the population is a homogenous population of cells. The cells of the population could be different, such that the population is a mixed population or a heterogeneous population of cells. For example, a mixed population of cells could include modified cells comprising a first CAR and cells comprising a second CAR, wherein the first CAR and the second CAR bind different antigens.

The term "stem cell" refers to any of certain types of cells which have the capacity for self-renewal and the ability to differentiate into other kind(s) of a cell. For example, a stem cell gives rise either to two daughter stem cells (as occurs in vitro with embryonic stem cells in culture) or to one stem cell and a cell that undergoes differentiation (as occurs, e.g., in hematopoietic stem cells, which give rise to blood cells). Different categories of stem cells may be distinguished on the basis of their origin and/or on the extent of their capacity for differentiation into other types of cells. For example, stem cells may include embryonic stem (ES) cells (i.e., pluripotent stem cells), somatic stem cells, induced pluripotent stem cells, and any other types of stem cells.

The pluripotent embryonic stem cells are found in the inner cell mass of a blastocyst and have an innate capacity for differentiation. For example, pluripotent embryonic stem cells have the potential to form any type of cell in the body. When grown in vitro for long periods of time, ES cells maintain pluripotency as progeny cells retain the potential for multilineage differentiation.

Somatic stem cells can include fetal stem cells (from the fetus) and adult stem cells (found in various tissues, such as bone marrow). These cells have been regarded as having a capacity for differentiation that is lower than that of the pluripotent ES cells—with the capacity of fetal stem cells being greater than that of adult stem cells. Somatic stem cells apparently differentiate into only a limited number of types of cells and have been described as multipotent. The "tissue-specific" stem cells normally give rise to only one type of cell. For example, embryonic stem cells may be differentiated into blood stem cells (e.g., hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing an expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be obtained from adult stomach, liver, skin, and blood cells.

In embodiments, the antigen binding domain for killing a tumor binds an antigen on the surface of a tumor, for example, a tumor antigen or tumor marker. Tumor antigens are proteins that are produced by tumor cells that elicit an immune response, particularly T cell mediated immune responses. Tumor antigens are well known in the art and include, for example, tumor associated MUC1 (tMUC1), a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, surviving, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, CD19, and mesothelin. For example, when the tumor antigen is CD19, the CAR thereof can be referred to as CD19 CAR (19CAR, CD19 CAR, or CD19-CAR), which is a CAR molecule that includes an antigen binding domain that binds CD19.

In embodiments, the extracellular antigen binding domain of a CAR includes at least one scFv or at least a single domain antibody. As an example, there can be two scFvs on a CAR. The scFv includes a light chain variable (VL) region and a heavy chain variable (VH) region of a target antigen-specific monoclonal antibody joined by a flexible linker. Single chain variable region fragments can be made by linking light and/or heavy chain variable regions by using a short linking peptide (Bird et al., Science 242:423-426, 1988). An example of a linking peptide is the GS linker having the amino acid sequence (GGGGS)$_3$ (SEQ ID NO: 30), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. The single chain variants can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect, or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The cytoplasmic domain of the CAR molecules described herein includes one or more co-stimulatory domains and one or more signaling domains. The co-stimulatory and signaling domains function to transmit the signal and activate molecules, such as T cells, in response to antigen binding. The one or more co-stimulatory domains are derived from stimulatory molecules and/or co-stimulatory molecules, and the signaling domain is derived from a primary signaling domain, such as the CD3 zeta domain. In embodiments, the signaling domain further includes one or more functional signaling domains derived from a co-stimulatory molecule. In embodiments, the co-stimulatory molecules are cell surface molecules (other than antigens receptors or their ligands) that are required for activating a cellular response to an antigen.

In embodiments, the co-stimulatory domain includes the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, or any combination thereof. In embodiments, the signaling domain includes a CD3 zeta domain derived from a T cell receptor.

The CAR molecules described herein also include a transmembrane domain. The incorporation of a transmembrane domain in the CAR molecules stabilizes the molecule. In embodiments, the transmembrane domain of the CAR molecules is the transmembrane domain of a CD28 or 4-1BB molecule.

Between the extracellular domain and the transmembrane domain of the CAR, there may be incorporated a spacer domain. As used herein, the term "spacer domain" generally means any oligo- or polypeptide that functions to link the transmembrane domain to the extracellular domain and/or the cytoplasmic domain on the polypeptide chain. A spacer domain may include up to 300 amino acids, preferably 10 to 100 amino acids, and most preferably 25 to 50 amino acids.

At present, in order to help expand CAR T cells in vivo, it is necessary to express antigen to stimulate the proliferation of CAR T cells, such as DC vaccine/lipid chain integrating antigen on the surface of DC/overexpression in certain immune cells Methods such as tumor cell surface antigens 3-5. This long-term amplification method that relies on TCR signals can stimulate the expansion of T cells in a large amount, but it will cause the cells to be exhausted and apoptosis very quickly, leaving the cells in a dysfunctional state. The expression of cytokines such as IL2/IL7/IL12/IL15/IL18/IL23/is one of the methods 6-9. Although IL12 and IL18 will rapidly expand cells, they will also lead to rapid cell differentiation and increase CAR—The exhaustion and toxicity of T cells, the expression of IL7/IL15 will keep the cells in the memory state, but it does not result in a good expansion of the cell number. At present, there is no way to maintain the cell memory state and rapidly expand.

We found the source genes of antigen-independent expansion through single-cell sequencing, which cannot be achieved by conventional methods such as overexpression factors. The present invention combines the downstream activation form molecules or persistent activation receptors of signals such as cytokine with solid tumor CAR to continuously express or induce the expression of persistent activation molecules in CAR to expand T cells. By inducing expression in CAR T to replace the role of cytokine, CAR T can be amplified in the state of naïve without or with little cytokine, enhancing its amplification effect and reducing side effects. After CAR T is amplified to a sufficient amount, the inducing factors are removed to further control its expansion. Also, the present invention expresses or knocks out transcription factors in solid tumor CAR. Allows CAR T to expand in the state of naïve without or with little cytokine, enhances its expansion effect and reduces side effects, and can reprogram T cells so that the depleted T cells can return to the state of naïve. In embodiments, by infecting T cells with multiple viruses, multiple gene expression composite T cells can be obtained from the T cell population, thereby achieving a stronger amplification effect.

The present disclosure describes compositions and methods for treating cancer. Embodiments relate to a cell modified to express one or more molecules at a level that is higher or lower than the level of the one or more expressed by a cell that has not been modified to express the one or more molecules, wherein the one or more molecules are identified in single-cell profiling analysis. Embodiments relate to a modified cell engineered to express an antigen binding molecule, wherein the expression and/or function of one or more molecules in the modified cell has been enhanced or reduced (including eliminated), where the one or more molecules are identified in single-cell profiling analysis. In embodiments, the modified cell comprises a disruption in an endogenous gene or addition of exogenous gene that is associated with a biosynthesis or transportation pathway of the one or more molecules. Embodiments relate to a pharmaceutical composition comprising the population of the cells.

Examples of overexpressed molecules include PLEKHN1, IL2, IL17F, IL31, IL3, CCL22, TNFSF4, PMCH, CCL1, XCL2, CCL17, TNIP3, IL5, G0S2, IL22, CSF2, CAVIN3, CCL4, CCL3, CCL4L2, IFNG, XCL1, CXCL10, ZBED2, CXCL9, CD40, FSCN1, GNLY, TPRG1, AL031777.3, LYN, LTA, CRTAM, GZMB, MIR155HG, MT2A, IL13, ELL2, RGS16, IER3, DUSP4, FABP5, LMNA, DUSP2, MYC, PHLDA2, BCL2A1, BCAT1, NPM3, CCDC50, HSP90AB1, ODC1, TXN, PIM3, RAN, NAMPT, H2AFZ, PRDX1, LGALS1, MIF, EIF4G2, CCL5, TAGLN2, TRAF1, TUBB, CDC42, TUBA1B, FTL, NFKBIA, PGAM1, PTMA, YWHAZ, TCP1, TPT1, CD70, PPIA, SEC61B, TMSB4X, PFN1, LDHA, HNRNPAB, BIRC3, NME2, TUBA1C, ATP5MC3, ANP32E, PTGES3, H3F3B, IL2RA, PKM, SH3BGRL3, HMGB1, ACTG1, ENO1, VIM, TMSB10, EIF1, SERBP1, TPM3, BTF3, CFL1, MYL6, ATP5MC2, ACTB, OAZ1, S100A4, and PGK1.

Embodiments relate to a method or use of polynucleotide, the method comprising providing a viral particle (e.g., AAV, lentivirus or their variants) comprising a vector genome, the vector genome comprising the polynucleotide encoding the one more molecules and a polynucleotide encoding an antigen binding molecule, the polynucleotide operably linked to an expression control element conferring transcription of the polynucleotides; and administering an amount of the viral particle to a subject such that the polynucleotide is expressed in the subject, where the one or more molecules are identified in single-cell profiling analysis. In embodiments, the AAV preparation may include AAV vector particles, empty capsids, and host cell impurities, thereby providing an AAV product substantially free of AAV empty capsids.

Embodiments relate to a method of causing or eliciting T cell response in a subject in need thereof and/or treating a tumor of the subject, the method comprising administering an effective amount of the composition of embodiment 6 to the subject. Embodiments relate to an isolated nucleic acid encoding one or more molecules associated with the metabolism of the modified cell.

In embodiments, the one more molecules comprise at least one of (overexpression or inducible overexpression) JAK2, STAT1, STAT2, STAT3, STAT4, PRKCA, PRKCQ, MAP3K1, MAP3K4, MAP3K8, MAPK14, BRAF, SMAD5, IL2RB, IL12RB2, IL18R1, IL21R, IL7R, CD28, Cavin3, ZBED2, MYC, EGFR, HER2, HER3, HER4, VEGFR2, VEGFR3, PDGFRα, PDGFRβ, gp130, IL-23R, IL-7R, CRLF2, βc, GHR, THPOR, EPOR, LepR, CSF3R, TNFR1, TGFBR1, TGFBR2, ACVR1A, BMPR2 ACVR1B, CXCR1, CXCR2, CXCR3, CXCR4, CCR2, and CCR5; and/or (knock out or knockdown) TOX, TOX2, TOX4, NR4A2, NR4A3, a functional variant of the one or more molecules, or a functional fragment of the one or more molecules.

In embodiments, the modified cell comprises an exogenous polynucleotide encoding modified STAT 1, STAT 2, and/or STAT 3. For example, one or more point mutations may be made such that the modified STAT 1, STAT 2, and/or STAT 3 can auto-phosphorylate to allow their signaling to be activated independently to enhance cell expansion and anti-apoptosis of the modified cell. In embodiments, the modified cell comprises at least one of SEQ ID NO: 35-43, 45-52, 54, and 55.

In embodiments, the cell modified to express one or more molecules at a level that is higher than the level of the one or more expressed by a cell that has not been modified to express the one or more molecules, the one more molecules comprise at least one of JAK2, STAT1, STAT2, STAT3, STAT4, PRKCA, PRKCQ, MAP3K1, MAP3K4, MAP3K8, MAPK14, BRAF, SMAD5, IL2RB, IL12RB2, IL18R1, IL21R, IL7R, CD28.

In embodiments, the cell modified to express one or more molecules at a level that is higher than the level of the one or more expressed by a cell that has not been modified to express the one or more molecules, the one more molecules comprise at least one of Cavin3, ZBED2, MYC.

In embodiments, the cell modified to express one or more molecules at a level that is higher than the level of the one or more expressed by a cell that has not been modified to express the one or more molecules, the one more molecules comprise at least one of EGFR, HER2, HER3, HER4, VEGFR2, VEGFR3, PDGFRα, PDGFRβ, gp130, IL-23R, IL-7R, CRLF2, βc, GHR, THPOR, EPOR, LepR, CSF3R, TNFR1, TGFBR1, TGFBR2, ACVR1A, BMPR2 ACVR1B, CXCR1, CXCR2, CXCR3, CXCR4, CCR2, and CCR5.

In embodiments, the cell modified to express one or more molecules at a level that is lower than the level of the one or more expressed by a cell that has not been modified to express the one or more molecules, the one more molecules comprise at least one of TOX, TOX2, TOX4, NR4A2, NR4A3.

In embodiments, the modified cell comprises an antigen binding molecule. In embodiments, the antigen binding molecule is the CAR, which comprises an antigen-binding domain, a transmembrane domain, and an intracellular signaling domain. In embodiments, the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRCSD, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LACE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1. In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D In embodiments, the modified cell comprises the antigen binding molecule, the antigen binding molecule is a modified TCR (TCR) or TCR (TIL). In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof.

In embodiments, wherein the cell is an immune effector cell (e.g., a population of immune effector cells). In embodiments, the immune effector cell is a DC, macrophage, T cell, or NK cell. In embodiments, the immune effector cell is a T cell. In embodiments, the T cell is a CD4+ T cell, a CD8+ T cell, or a combination thereof. In embodiments, the cell is a human cell.

In embodiments, the enhanced expression and/or function of the one or more molecules is implemented by introducing a nucleic acid encoding the one or more molecules and/or the binding molecule, which is present in the modified cell in a recombinant DNA construct, in an mRNA, or in a viral vector. In embodiments, the nucleic acid is an mRNA, which is not integrated into the genome of the modified cell. In embodiments, the nucleic acid is associated with an oxygen-sensitive polypeptide domain. In embodiments, the oxygen-sensitive polypeptide domain comprises HIF VHL binding domain. In embodiments, the nucleic acid is regulated by a promoter comprising a binding site for a transcription modulator that modulates the expression and/or secretion of the therapeutic agent in the cell. In embodiments, the transcription modulator is or includes Hif1a, NFAT, FOXP3, and/or NFkB.

Embodiments relate to a modified DC comprising a polynucleotide encoding an antigen binding molecule, which comprises an antigen-binding domain, a transmembrane domain, and an intracellular signaling domain. Some embodiments relate to an isolated nucleic acid encoding an antigen binding molecule, which comprises an antigen-binding domain, a transmembrane domain, and an intracellular signaling domain. Some embodiments relate to a pharmaceutical composition comprising the population of the cells. Some embodiments relate to a method of enhancing T cell response in a subject in need thereof and/or treating a tumor of the subject, the method comprising administering an effective amount of the composition to the subject. Some embodiments relate to a method or use of polynucleotide, the method comprising providing a viral particle (e.g., AAV, lentivirus or their variants) comprising a vector genome, the vector genome comprising the nucleic acid, the polynucleotide operably linked to an expression control element conferring transcription of the polynucleotides; and administering an amount of the viral particle to a subject such that the polynucleotide is expressed in the subject, where the one or more molecules are overexpressed in cancer cells, associated with recruitment of immune cells, and/or associated with autoimmunity. In embodiments, the AAV preparation may include AAV vector particles, empty capsids, and host cell impurities, thereby providing an AAV product substantially free of AAV empty capsids.

In embodiments, the expression of one or more molecules is regulated by one or more promoters. In embodiments, the polynucleotide comprises a promoter comprising a binding site for a transcription modulator that modulates the expression and/or secretion of the one or more molecules in the cell. For example, the transcription modulator is or includes Hif1a, NFAT, FOXP3, and/or NFkB. For example, the one or more molecules comprise at least one cytokine associated with an oxygen-sensitive polypeptide domain, and the oxygen-sensitive polypeptide domain comprises HIF VHL binding domain.

In embodiments, the polynucleotide may integrate into the genome of the modified cell, and descendants of the modified cell will also express the polynucleotide, resulting in a stably transfected modified cell. In embodiments, the modified cell may express the polynucleotide encoding the CAR, but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

At present, the most effective method for treating cancer is CAR T, but there are several problems in CAR T in solid tumors: 1. How to migrate into tumor cells; 2. Need DC cells to provide some special factors (such as IL12) 3. The ability to present new antigens by themselves. How to fully activate DC cells, before doing CAR-DC-like articles or CAR T CAR molecules, the activation of these two cells is very different (T cells mainly rely on TCR). The main signal of DC cells is derived from TOLL like Receptor). 2. The proportion of DC cells in peripheral blood is less than that of T cells, which is difficult to purify and culture. The present invention allows DC to specifically recognize tumors, enhance the function of DC cells, recruit other modified and unmodified immune cells through DC, and release various cytokines (IL12, etc.) through DC to promote immune system function through DC activation. Other immune cells, thereby enhancing the effectiveness of immunotherapy. Related experiments include: 1. nCAR-DC killing experiment, 2. tCAR-DC (TraditionCAR) killing experiment, 3. nCAR-DC+NT killing experiment, 4. tCAR-DC+ NT killing experiment, 5. nCAR-DC+CAR-T killing experiment, 6. tCAR-DC+CAR T killing experiment. The present invention is based on a CAR designed by Toll-Like Receptor (TLR) to fully activate DC cells and to promote the function of DC cells to recognize tumors. At the same time, we can also express in DC cells with the structure of CAR suitable for CAR T, thereby activating DC cells and promoting the function of DC cells. It can also be a combination of CAR-DC and CAR T, TIL, TCR, and other cell therapies. The Signal domain includes 10 different TLRs; TLR1-10 (planned experiments using TLR9 or Myd88). Myd88: Myeloid differentiation factor, with the same TIR domain as the intracellular domain of the TLR molecule, is a key linker molecule in the TLR and plays a key role in transmitting downstream information. TRIF can produce IFN-[beta] and an adaptor protein containing a TIR domain.

In embodiments, the transmembrane domain comprises a transmembrane domain of at least one of the molecules listed in the following table (e.g., CD8 CD40).

| Molecules | Sequences of Transmembrane Domain |
|---|---|
| CD8b | SEQ ID NO: 1 |
| CD8a | SEQ ID NO: 2 |
| CD40 | SEQ ID NO: 3 |
| CD4 | SEQ ID NO: 4 |
| CD5 | SEQ ID NO: 5 |
| CD3zeta | SEQ ID NO: 6 |
| CD22 | SEQ ID NO: 7 |
| CD28 | SEQ ID NO: 8 |
| CD33 | SEQ ID NO: 9 |
| CD64 | SEQ ID NO: 10 |
| CD80 | SEQ ID NO: 11 |
| CD86 | SEQ ID NO: 12 |
| CD134 | SEQ ID NO: 13 |
| CD137 | SEQ ID NO: 14 |
| CD154 | SEQ ID NO: 15 |

In embodiments, the intracellular signaling domain comprises a signaling domain of at least one of TLR1, TLR2, TLR3, TLR4, TLR5, TLR6, TLR7, TLR8, TLR9, TLR10, TLR11, MYD88, TRIF, TRAM, and TIRAP. In embodiments, the intracellular signaling domain comprises a signaling domain of at least one of TLR9 and MYD88. In embodiments, the intracellular signaling domain comprises a signaling domain of at least one of the molecules listed in the following table.

| Molecules | Sequences of Signaling Domain |
|---|---|
| TLR1 | SEQ ID NO: 16 |
| TLR2 | SEQ ID NO: 17 |
| TLR3 | SEQ ID NO: 18 |
| TLR4 | SEQ ID NO: 19 |

-continued

| Molecules | Sequences of Signaling Domain |
|---|---|
| TLR5 | SEQ ID NO: 20 |
| TLR6 | SEQ ID NO: 21 |
| TLR7 | SEQ ID NO: 22 |
| TLR8 | SEQ ID NO: 23 |
| TLR9 | SEQ ID NO: 24 |
| TLR10 | SEQ ID NO: 25 |
| MYD88 | SEQ ID NO: 26 |
| TRIF | SEQ ID NO: 27 |
| TRAM | SEQ ID NO: 28 |
| TIRAP | SEQ ID NO: 29 |

In embodiments, the intracellular signaling domain comprises at least one of CD40 and RAGE In embodiments, the antigen binding molecule is a CAR. In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D In embodiments, the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, W1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In embodiments, the antigen binding molecule further comprises a CD3 zeta domain. In embodiments, the antigen binding molecule is a modified TCR. In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof.

In embodiments, the cell is a human cell. In embodiments, the enhanced expression and/or function of the one or more molecules is implemented by introducing a nucleic acid encoding the one or more molecules and/or the binding molecule, which is present in the modified cell in a recombinant DNA construct, in an mRNA, or in a viral vector. In embodiments, the nucleic acid is an mRNA, which is not integrated into the genome of the modified cell.

Embodiments relate to a cell modified to express one or more molecules at a level that is higher or lower than the level of the one or more expressed by a cell that has not been modified to express the one or more molecules, wherein the one or more molecules are identified in single-cell profiling analysis.

Embodiments relate to a modified cell engineered to express an antigen binding molecule, wherein the expression and/or function of one or more molecules in the modified cell has been enhanced or reduced (including eliminated), wherein the one or more molecules are identified in single-cell profiling analysis.

Embodiments relate to a method or use of polynucleotide, the method comprising providing a viral particle (e.g., AAV, lentivirus or their variants) comprising a vector genome, the vector genome comprising the polynucleotide encoding the one more molecules and a polynucleotide encoding an antigen binding molecule, the polynucleotide operably linked to an expression control element conferring transcription of the polynucleotides; and administering an amount of the viral particle to a subject such that the polynucleotide is expressed in the subject, where the one or more molecules are identified in single-cell profiling analysis.

Embodiments relate to a pharmaceutical composition comprising the population of the cells.

Embodiments relate to a method of causing or eliciting T cell response in a subject in need thereof and/or treating a tumor of the subject, the method comprising administering an effective amount of the composition to the subject.

Embodiments relate to an isolated nucleic acid encoding one or more molecules associated with the metabolism of the modified cell.

In embodiments, the modified cell comprises a disruption in an endogenous gene or addition of exogenous gene that is associated with a biosynthesis or transportation pathway of the one or more molecules.

In embodiments, the AAV preparation may include AAV vector particles, empty capsids, and host cell impurities, thereby providing an AAV product substantially free of AAV empty capsids.

In embodiments, the one more molecules comprise at least one of (overexpression or inducible overexpression) JAK2, STAT1, STAT2, STAT3, STAT4, PRKCA, PRKCQ, MAP3K1, MAP3K4, MAP3K8, MAPK14, BRAF, SMAD5, IL2RB, IL12RB2, IL18R1, IL21R, IL7R, CD28, Cavin3, ZBED2, MYC, EGFR, HER2, HER3, HER4, VEGFR2, VEGFR3, PDGFRα, PDGFRβ, gp130, IL-23R, IL-7R, CRLF2, βc, GHR, THPOR, EPOR, LepR, CSF3R, TNFR1, TGFBR1, TGFBR2, ACVR1A, BMPR2 ACVR1B, CXCR1, CXCR2, CXCR3, CXCR4, CCR2, and CCR5; and/or (knock out or knockdown) TOX, TOX2, TOX4, NR4A2, NR4A3, a functional variant of the one or more molecules, or a functional fragment of the one or more molecules.

In embodiments, the cell modified to express one or more molecules at a level that is higher than the level of the one or more expressed by a cell that has not been modified to express the one or more molecules, the one more molecules comprise at least one of JAK2, STAT1, STAT2, STAT3, STAT4, PRKCA, PRKCQ, MAP3K1, MAP3K4, MAP3K8, MAPK14, BRAF, SMAD5, IL2RB, IL12RB2, IL18R1, IL21R, IL7R, CD28.

In embodiments, the cell modified to express one or more molecules at a level that is higher than the level of the one or more expressed by a cell that has not been modified to express the one or more molecules, the one more molecules comprise at least one of Cavin3, ZBED2, MYC.

In embodiments, the cell modified to express one or more molecules at a level that is higher than the level of the one or more expressed by a cell that has not been modified to express the one or more molecules, the one more molecules comprise at least one of EGFR, HER2, HER3, HER4, VEGFR2, VEGFR3, PDGFRα, PDGFRβ, gp130, IL-23R, IL-7R, CRLF2, βc, GHR, THPOR, EPOR, LepR, CSF3R, TNFR1, TGFBR1, TGFBR2, ACVR1A, BMPR2 ACVR1B, CXCR1, CXCR2, CXCR3, CXCR4, CCR2, and CCR5.

In embodiments, the cell modified to express one or more molecules at a level that is lower than the level of the one or more expressed by a cell that has not been modified to express the one or more molecules, the one more molecules comprise at least one of TOX, TOX2, TOX4, NR4A2, NR4A3.

In embodiments, the modified cell comprises an antigen binding molecule.

In embodiments, the antigen binding molecule is the CAR, which comprises an antigen-binding domain, a transmembrane domain, and an intracellular signaling domain.

In embodiments, the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRCSD, CXORF61, CD97, CD179a, ALK, Polysialic acid, PLAC1, GloboH, NY-BR-1, UPK2, HAVCR1, ADRB3, PANX3, GPR20, LY6K, OR51 E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D In embodiments, the modified cell comprises the antigen binding molecule, the antigen binding molecule is a modified TCR (TCR) or TCR (TIL).

In embodiments, the TCR is derived from spontaneously occurring tumor-specific T cells in patients.

In embodiments, the TCR binds to a tumor antigen.

In embodiments, the tumor antigen comprises CEA, gp100, MART-1, p53, MACE-A3, or NY-ESO-1.

In embodiments, the TCR comprises TCRγ and TCRδ Chains or TCRα and TCRβ chains, or a combination thereof.

In embodiments, the cell is an immune effector cell (e.g., a population of immune effector cells).

In embodiments, the immune effector cell is a DC, macrophage, T cell, or NK cell.

In embodiments, the immune effector cell is a T cell.

In embodiments, the T cell is a CD4+ T cell, a CD8+ T cell, or a combination thereof.

In embodiments, the cell is a human cell.

In embodiments, the enhanced expression and/or function of the one or more molecules is implemented by introducing a nucleic acid encoding the one or more molecules and/or the binding molecule, which is present in the modified cell in a recombinant DNA construct, in an mRNA, or in a viral vector.

In embodiments, the nucleic acid is an mRNA, which is not integrated into the genome of the modified cell.

In embodiments, the nucleic acid is associated with an oxygen-sensitive polypeptide domain.

In embodiments, the oxygen-sensitive polypeptide domain comprises HIF VHL binding domain.

In embodiments, the nucleic acid is regulated by a promoter comprising a binding site for a transcription modulator that modulates the expression and/or secretion of the therapeutic agent in the cell.

In embodiments, the transcription modulator is or includes Hif1a, NFAT, FOXP3, and/or NFkB.

Embodiments relate to a modified DC comprising a nucleic acid encoding an antigen binding molecule, which comprises an antigen-binding domain, a transmembrane domain, and an intracellular signaling domain.

Embodiments relate to an isolated nucleic acid encoding an antigen binding molecule, which comprises an antigen-binding domain, a transmembrane domain, and an intracellular signaling domain.

Embodiments relate to a method or use of polynucleotide, the method comprising providing a viral particle (e.g., AAV, lentivirus or their variants) comprising a vector genome, the vector genome comprising the nucleic acid, the polynucleotide operably linked to an expression control element conferring transcription of the polynucleotides; and administering an amount of the viral particle to a subject such that the polynucleotide is expressed in the subject, where the one or more molecules are overexpressed in cancer cells, associated with recruitment of immune cells, and/or associated with autoimmunity.

In embodiments, the AAV preparation may include AAV vector particles, empty capsids, and host cell impurities, thereby providing an AAV product substantially free of AAV empty capsids.

Embodiments relate to a pharmaceutical composition comprising the population of the cells.

Embodiments relate to a method of enhancing T cell response in a subject in need thereof and/or treating a tumor of the subject, the method comprising administering an effective amount of the composition to the subject.

In embodiments, the transmembrane domain comprises a transmembrane domain of CD8 or CD40.

In embodiments, the intracellular signaling domain comprises a signaling domain of at least one of TLR1, TLR2, TLR3, TLR4, TLR5, TLR6, TLR7, TLR8, TLR9, TLR10, TLR11, MYD88, TRIF, TRAM, and TIRAP.

In embodiments, the intracellular signaling domain comprises a signaling domain of at least one of TLR9 and MYD88.

In embodiments, the intracellular signaling domain comprises at least one of CD40 and RAGE In embodiments, the antigen binding molecule is the CAR.

In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D In embodiments, the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51 E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In embodiments, the antigen binding molecule further comprises a CD3 zeta domain.

In embodiments, the antigen binding molecule is a modified TCR.

In embodiments, the TCR is derived from spontaneously occurring tumor-specific T cells in patients.

In embodiments, the TCR binds to a tumor antigen.

In embodiments, the tumor antigen comprises CEA, gp100, MART-1, p53, MACE-A3, or NY-ESO-1.

In embodiments, the TCR comprises TCRγ and TCRδ Chains or TCRα and TCRβ chains, or a combination thereof.

In embodiments, the cell is a human cell.

In embodiments, the enhanced expression and/or function of the one or more molecules is implemented by introducing a nucleic acid encoding the one or more molecules and/or the binding molecule, which is present in the modified cell in a recombinant DNA construct, in an mRNA, or in a viral vector.

In embodiments, the nucleic acid is an mRNA, which is not integrated into the genome of the modified cell.

Embodiments relate to lymphocytes comprising one or more exogenous polynucleotides encoding MYC proto-oncogene, bHLH transcription factor (MYC), Caveolae Associated Protein 3 (CAVIN3) and/or Zinc finger bed-type containing 2 (ZBED2).

Embodiments relate to a method of enhancing an anti-tumor effect of a lymphocyte, the method comprising: introducing one or more exogenous polynucleotides encoding Caveolae Associated Protein 3 (CAVIN3) and/or Zinc finger bed-type containing 2 (ZBED2) into lymphocytes to obtain modified lymphocytes; contacting the modified lymphocytes with tumor cells that the modified lymphocytes bind; and allowing the modified lymphocytes to generate an anti-tumor effect, wherein the anti-tumor effect are enhanced as compared to those of lymphocytes without overexpressing CAVIN3 and ZBED2.

In embodiments, the exogenous polynucleotide comprises the amino acid of SEQ ID NO: 31, 32, and/or 33.

In embodiments, the lymphocytes are T cells or NK cells.

In embodiments, the anti-tumor effect is manifested by at least one of reduced cell exhaustion, enhanced cell expansion, and enhanced tumor growth inhibition.

In embodiments, a cell exhaustion level of the modified lymphocytes is lower than that of lymphocytes without overexpressing CAVIN3 and ZBED2.

In embodiments, a cell expansion level of the modified lymphocytes is higher than that of lymphocytes without overexpressing CAVIN3 and ZBED2.

In embodiments, tumor growth inhibition of the modified lymphocytes is greater than that of lymphocytes without overexpressing CAVIN3 and ZBED2.

In embodiments, a level of cytokine released by the modified lymphocytes is not significantly greater than that of lymphocytes without overexpressing CAVIN3 and ZBED2.

In embodiments, a level of activation of the modified lymphocytes is not significantly greater than that of lymphocytes without overexpressing CAVIN3 and ZBED2.

In embodiments, the lymphocytes comprise an antigen binding molecule.

In embodiments, the lymphocytes comprise a nucleic acid sequence encoding a dominant negative form of an inhibitory immune checkpoint molecule or a receptor thereof, and the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160.

In embodiments, the lymphocytes comprise a nucleic acid sequence encoding hTERT or a nucleic acid encoding SV40LT, or a combination thereof.

In embodiments, the lymphocytes comprise a nucleic acid sequence encoding a cytokine. In embodiments, the cytokine comprises IL-6, IL-7, IL-15, IL-12, or IFNγ.

In embodiments, the lymphocytes comprise a first population of T cells comprising a CAR binding a cell surface molecule of a white blood cell (WBC) and a second population of T cells comprising a CAR binding a solid tumor antigen.

EXAMPLES

CoupledCAR®: T Cell Expansion Via CD19 CAR T and B Cells

Figures 3A, 3B:
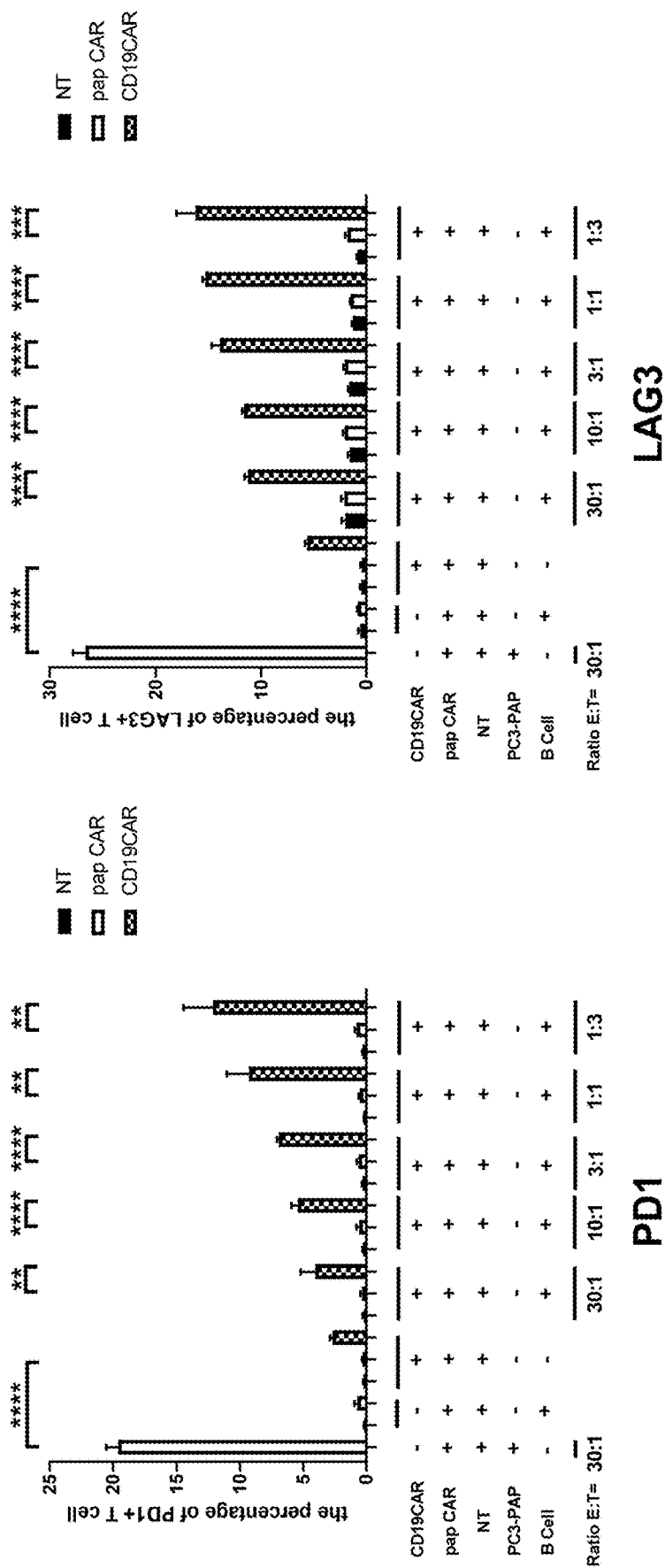
FIGS. 3A and 3B show the expression of markers for exhaustion on various cells (P value<0.05=*, <0.01=, <0.001=*, <0.0001=****; P≥0.05=no significance=NS).

FIG. 3 shows the expression of exhaustion markers on various cells. PAP CAR T cells, non-transferred T (NT) cells, and CD19 CART cells were co-cultured with B cells and/or substrate cells, respectively, and the expression of PD1 and Lag3 on these cells were measured (P-value<0.05=*, <0.01=, <0.001=*, <0.0001=****; P≥0.05=no significance=NS). Flow cytometry analysis was used to measure exhaustion levels of the cells. The results showed that in a CoupledCAR® system, the CD19 CART cells killed the B cells and up-regulated PD1 and LAG3. These markers were not up-regulated in NT cells and PAP CAR T cells as compared to CD19 CAR T cells, indicating that the stimulation of PAP CAR T cells in the CoupledCAR® system did not rely on antigens and that expansion of PAP CAR T cells was with little exhaustion.

Figure 4B:
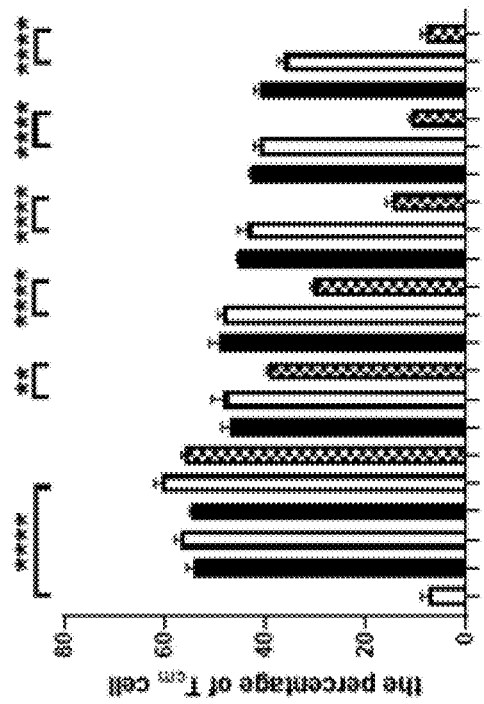
FIGS. 4A, 4B, 5, 6A, and 6B show the proportion of memory T cells, central memory T (Tcm) cells, and stem-like central memory T (Tscm) cells of the various cultured cells of FIG. 3.
Figure 4A:
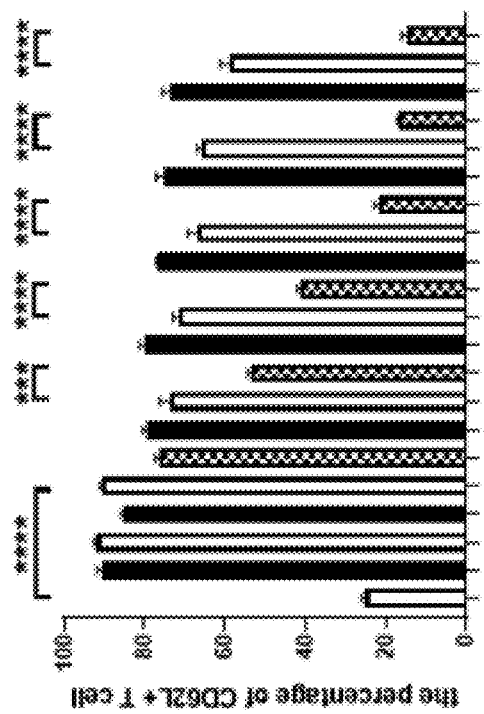
Figure 5:
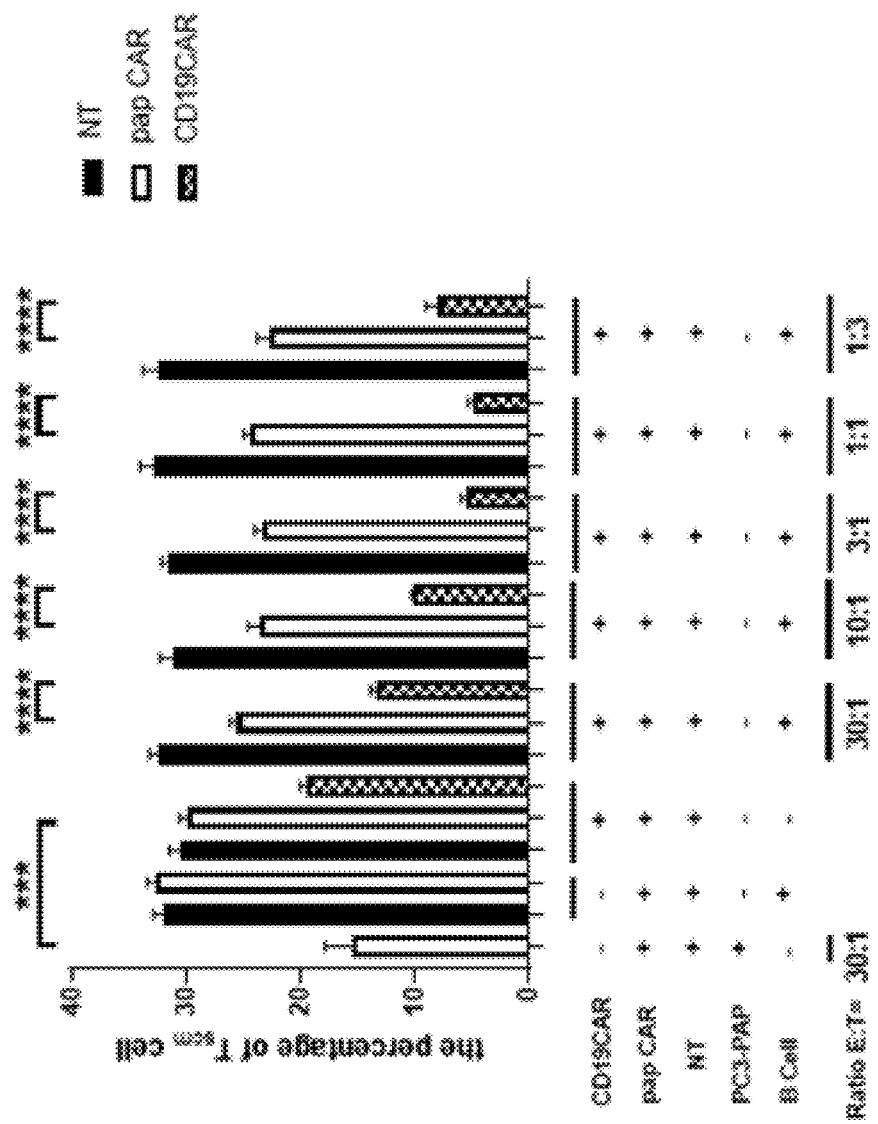
Figures 6A, 6B:
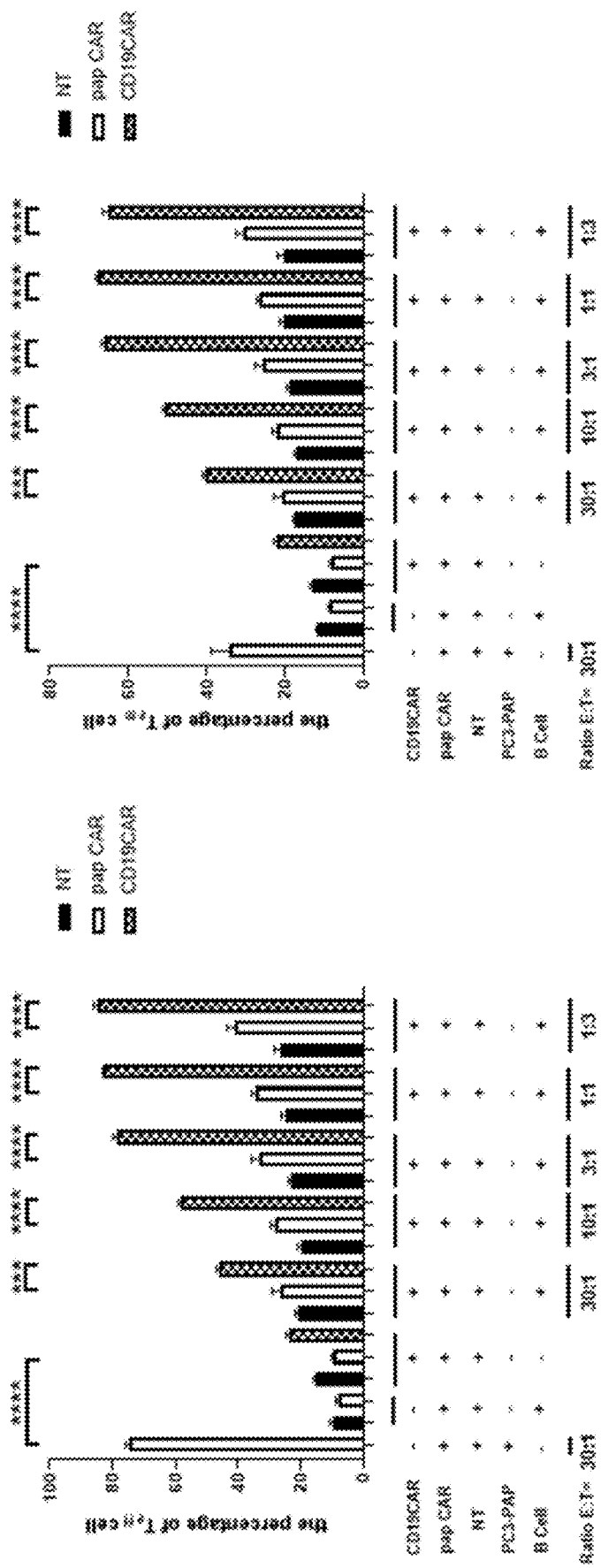

FIGS. 4-6 show the proportion of memory T cell, central memory T (Tcm) cell, and stem-like central memory T (Tscm) cell in various cells cultured as described for FIG. 3 (P-value<0.05=*, <0.01=, <0.001=*, <0.0001=****; P≥0.05=no significance=NS). Flow cytometry analysis results showed that in the CoupledCAR® system, CD19 CART cells were differentiated into effector cells by killing B cells while few memory cells were observed. PAP CAR T cells and NT cells were not differentiated into effector cells and maintained a high proportion of memory cells and memory cells with stem cell phenotypes. Thus, the CoupledCAR® system helped PAP CAR T cells maintain high differentiation potential until contact with solid tumors.

Figures 7A, 7B, 7C:
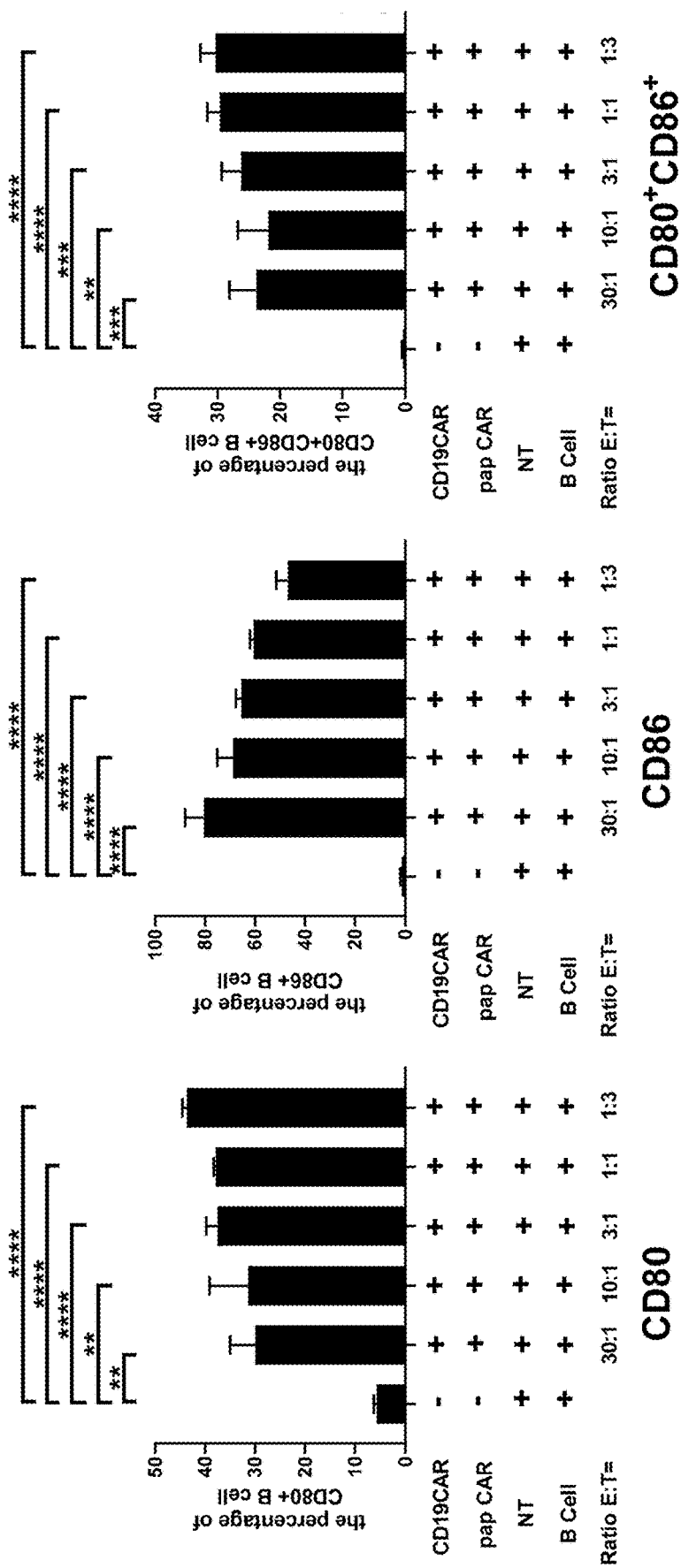
FIGS. 7A, 7B, and 7C show activation of B cells that are cultured with various cells.

FIG. 7 shows activation of B cells that are cultured with various cells (P value<0.05=*, <0.01=, <0.001=*, <0.0001=****; P≥0.05=no significance=NS). Results of flow cytometry analysis showed that the expression of CD80 and CD86 are up-regulated on B cells. CD80 and CD86 are expressed as cell surface molecules by APCs (e.g., B cells) and are responsible for delivering signals to T cells. For example, along with CD80, CD86 provides co-stimulatory signals necessary for T-cell activation and survival. Thus, in the CoupledCAR® system, B cells are also activated, and these activated B cells interact with T cells by providing signals (e.g., co-stimulatory signals) to enhance T cell activation and/or expansion and survival.

These results show that, in the CoupledCAR® system, CD19 CAR up-regulated expression inhibition markers such as PD1 and LAG3 after activation of CAR-mediated TCR. But surprisingly, few of these inhibition markers were expressed on PAP CAR T and NT cells. Moreover, compared with CD19 CART cells, PAP CAR T and NT cells inhibited more phenotypes of Tscm and Tcm cells and fewer phenotypes of effector cells. Also, the CoupledCAR® system did not significantly reduce the number of memory cells of PAP CAR T and NT cells as compared to a non-coupled CAR system. In hematological malignancies, CAR T cells are directed against lineage antigens of B cells and encounter the antigens on normal and malignant B cells of the subject. These B cells act as antigen-presenting cells (APCs) that provide strong proliferation signals to expand CAR T cells and lead to the persistence of CAR T cells. These results demonstrate the role of B cells in the CoupledCAR® system and indicate that CAR T cells targeting other B cell antigen (e.g., BCMA, CD22, CD20, etc.) may replace CD19 CART cells in a CoupledCAR® system (CD19 CART and PAP CART cells) as shown in FIGS. 3-7.

In embodiments, compositions, methods, and sequences associated with CoupledCAR® system are described in PCT Publication Nos: WO2020106843 and WO2020146743, which are incorporated by reference in their entirety.

T Cell Expansion Via Bispecific Antibody and B Cells

On day 0, the peripheral blood of healthy volunteers was drawn, and CD3+ T cells were sorted with Pan T Kit. 100 ul of T cell Transact™ (for activating and expanding human T cells via CD3 and CD28) were added per $1 \times 10^7$ T cells. On day 1, $4 \times 10^6$ 1234 T cells were transduced with a lentivirus vector encoding CD19 CAR (Table 2), and the multiplicity of infection (MOI) was 10. $4 \times 10^6$ 6503 T cells were transduced with lentivirus vectors encoding PAP CAR (Table 10), and the MOI was 49.98. $4 \times 10^6$ T cells were non-transduced T cells (NT cells). On day 2, the media were changed to remove lentivirus vectors and T cell TransAct™.

TABLE 2

| Name | Construction | Notes |
| --- | --- | --- |
| 1234 | CAR-h19-bbz | Humanized CD19 scFv and 4-1BB |
| 6503 | CAR-ACPP-bbz | ACPP (or PAP) scFv and 4-1BB |

Figure 8:
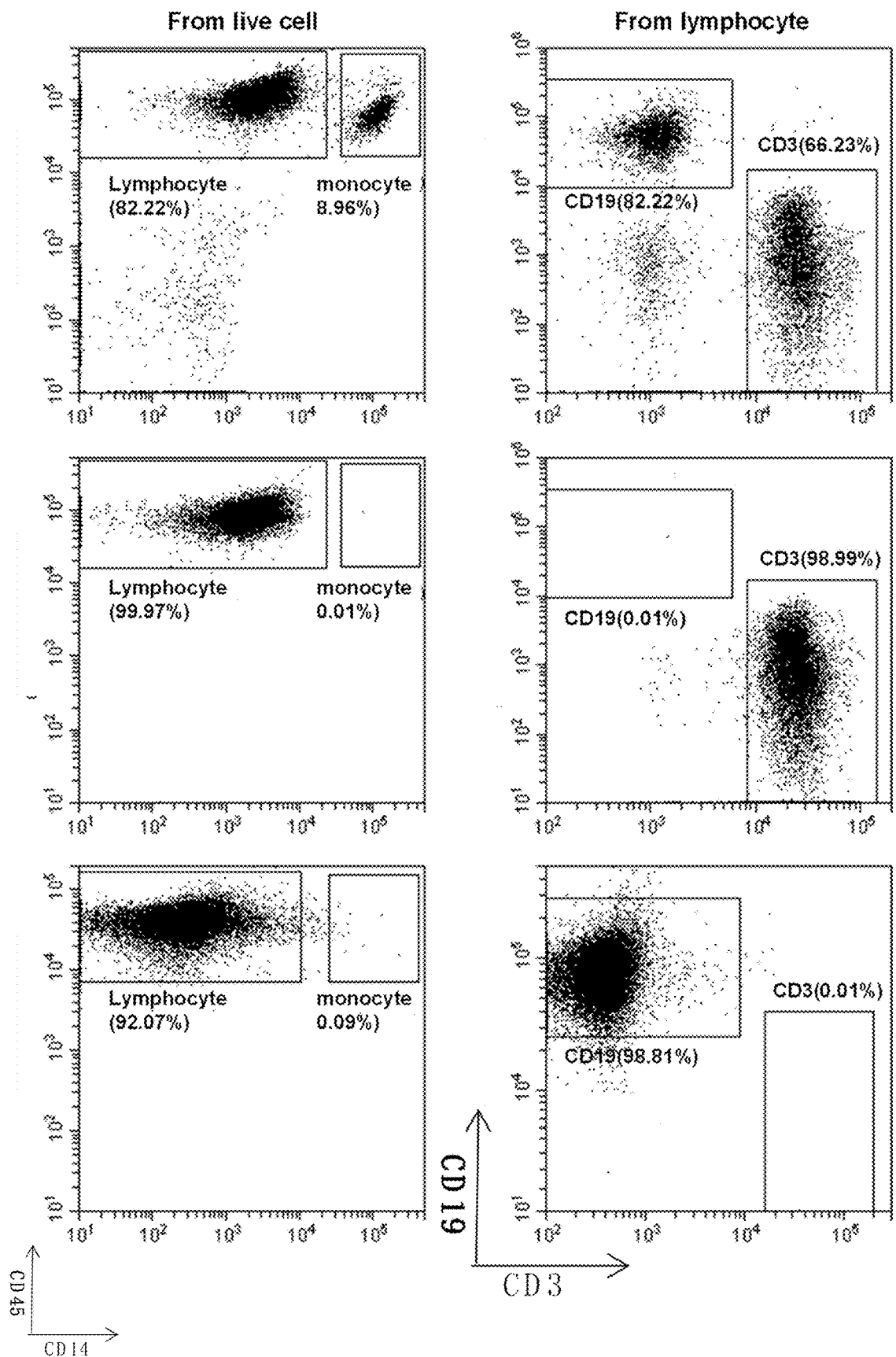
FIG. 8 shows results of flow cytometry analysis of sorting of B cells and T cells.
Figure 9:
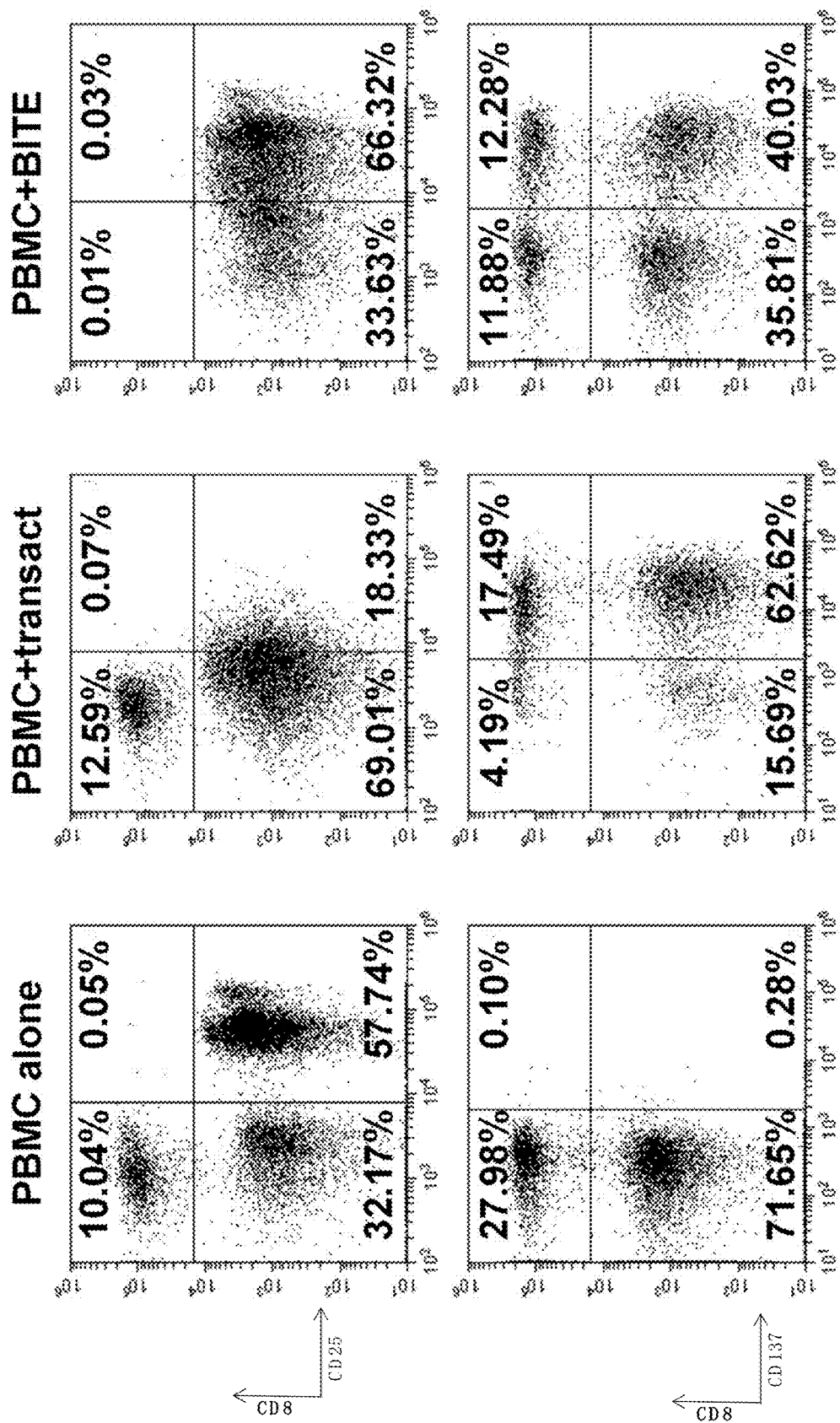
FIGS. 9 and 10 show results of flow cytometry analysis of expression of cell markers of co-cultured cells, including B cells and T cells in the presence or absence of CD3-CD19 bispecific antibody
Figure 10:
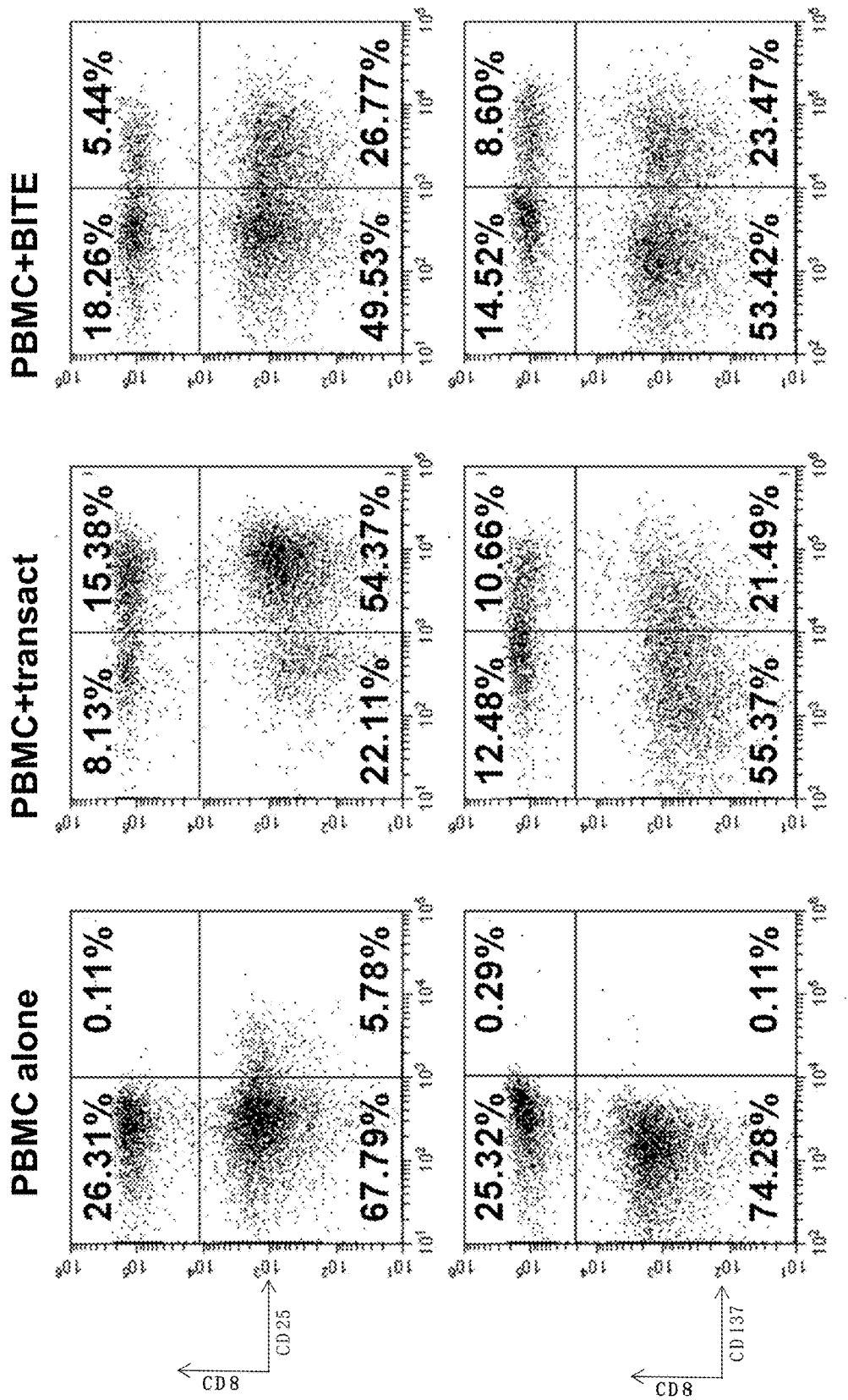
Figure 11:
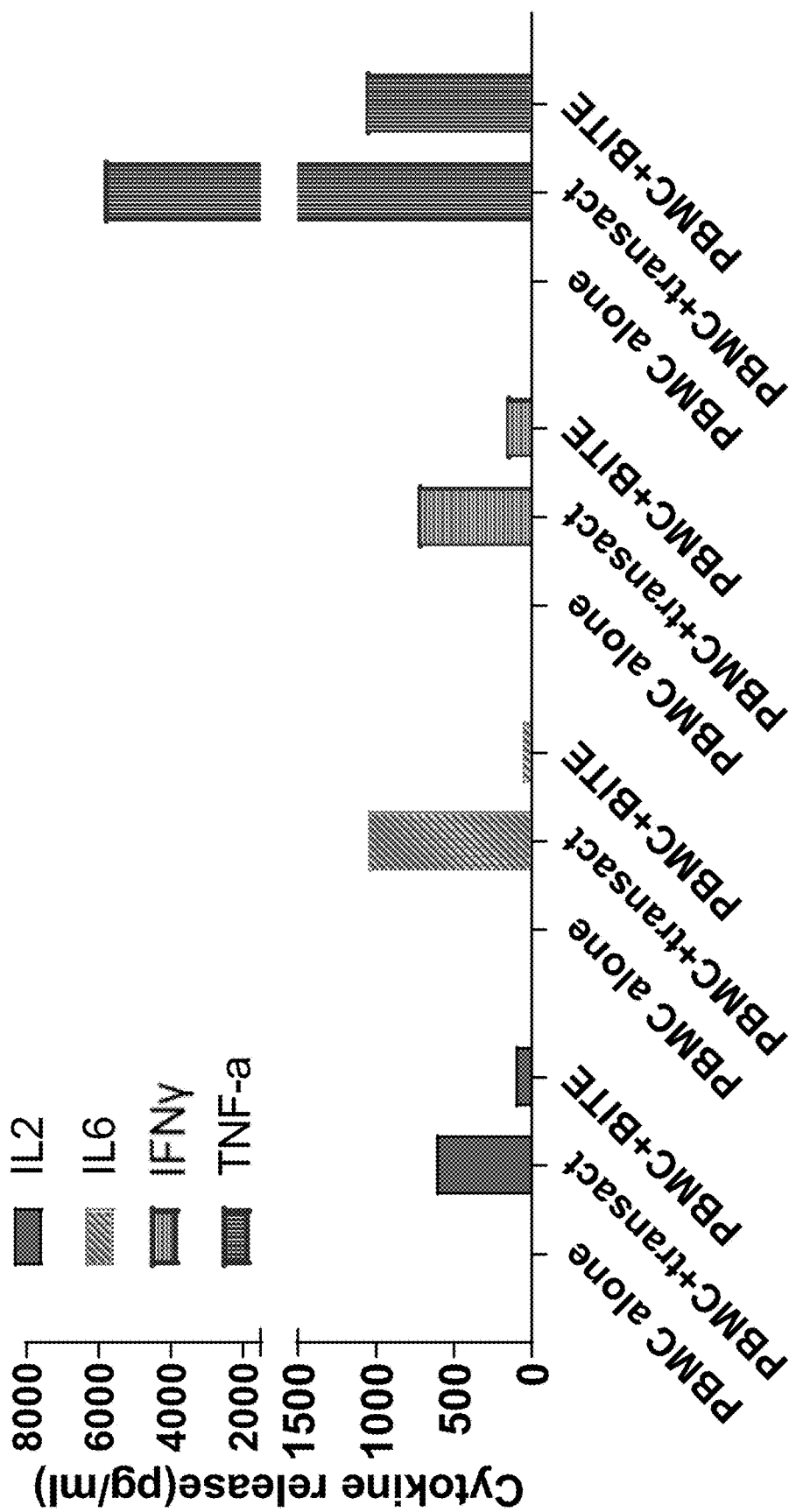
FIG. 11 shows results of flow cytometry analysis of cytokine release by the cells of FIGS. 9 and 10.

FIG. 8 shows results of flow cytometry analysis of sorting of B cells and T cells. FIGS. 9 and 10 show results of flow cytometry analysis of expression of cell markers of co-cultured cells including B cells and T cells in the absence and presence of CD3-CD19 bispecific antibody (CD3-CD19 bispecific antibody), which was purchased from Biointron (catalog number of B302001). FIG. 11 shows flow cytokine results of cytokine release in the experiments of FIGS. 9 and 10. These results show CD3 positive T cells and CD19 positive B cells are connected via CD3-CD19 bispecific antibody, resulting in activation of T cells and cytokine release to lyse B cells.

Figure 12:
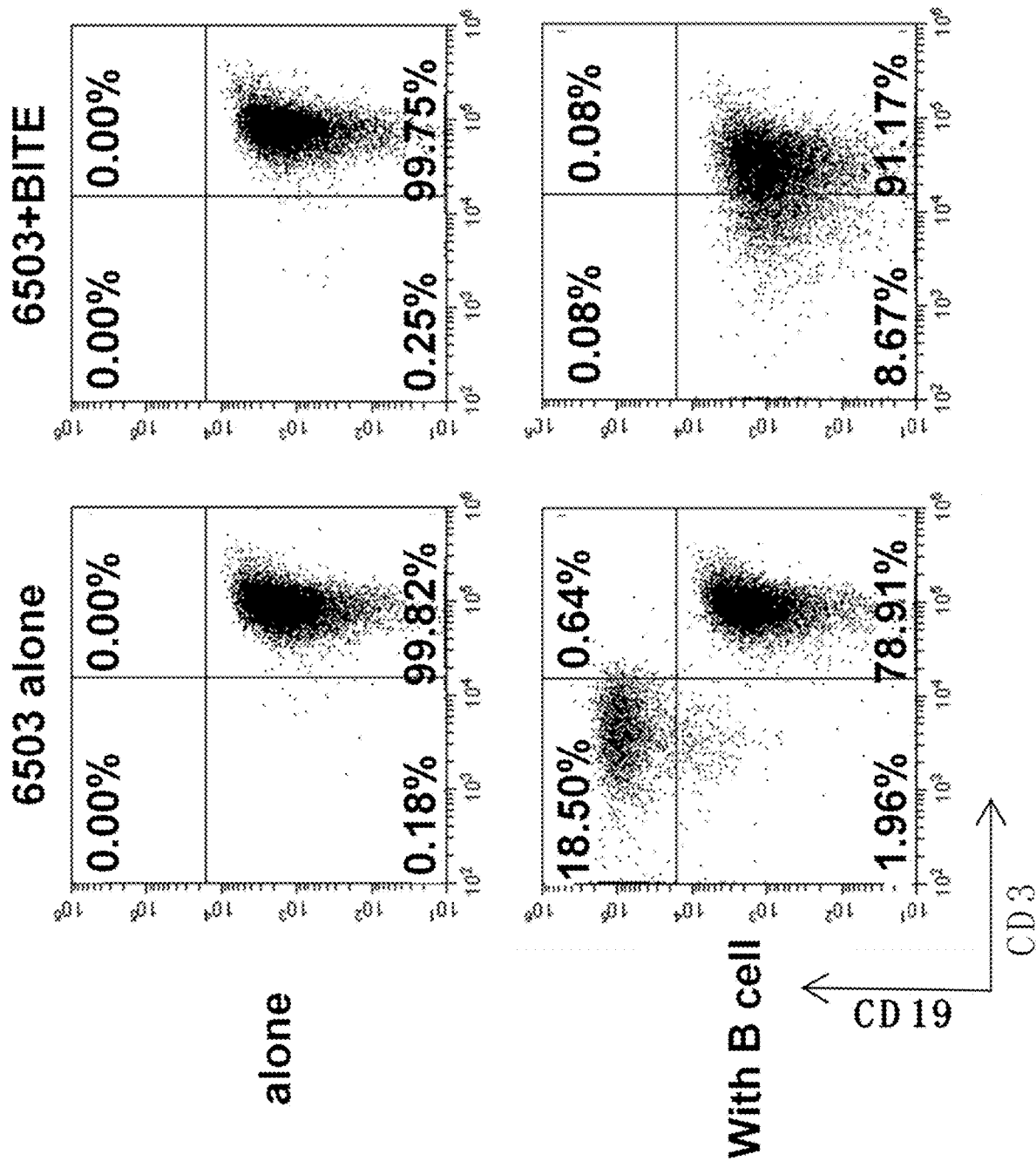
FIG. 12 shows results of flow cytometry analysis of PAP CART cells co-cultured with B cells in the presence or absence of CD3-CD19 bispecific antibody. PAP CAR T cells were generated and cultured for 7 days.

FIG. 12 shows results of flow cytometry analysis of PAP CART cells co-cultured with B cells with or without the presence of CD3-CD19 bispecific antibody. PAP CAR T cells were generated and cultured for 7 days. B cells were isolated from PMBCs. CD3-CD19 bispecific antibody was mixed with PAP CAR T cells or PAP CAR T cells co-cultured with B cells. It was observed that after the 6503 cells mixed with CD3-CD19 bispecific antibody killed the B cells, 6503 cells appeared to be activated. FIG. 13 shows histograms of results of flow cytometry analysis of expression of various markers on T cells and B cells in the experiments of FIG. 12. PAP CAR T cells were further co-cultured with B cells for 24 hours, and flow cytometry was used to detect the cell membrane markers. It was observed that the 6503 cells co-cultured with or without B cells did not appear to be activated. However, when CD3-CD19 bispecific antibody was added to the media, 6503 cells co-cultured with B cells were activated. 6503 cells alone mixed with CD3-CD19 bispecific antibody showed some activation, which might be caused by T cell Transact™ used in the transduction of lentivirus vectors into T cells to generate 6503 cells. Thus, these results show that CD3-CD19 bispecific antibody can cause solid tumor CART cells (e.g., PAP CART cells) to be activated, as CD19 CART cells were in the previous Examples. The activation of PAP CAR T cells was indicated by the expression of CD69, CD25, and CD137 on CD4 and CD8 subtype T cells, which was significantly increased. Also, CD40L expression of CD4 subtype T cells was up-regulated such as to allow these T cells to receive stimulation of CD40 positive APC cells. The amount of CD3-CD19 bispecific antibody is controllable; thus, these results indicate that CD3-CD19 bispecific antibody can cause the controllable activation of T cells by connecting and/or by narrowing the distance between T cells and B cells.

Figure 14:
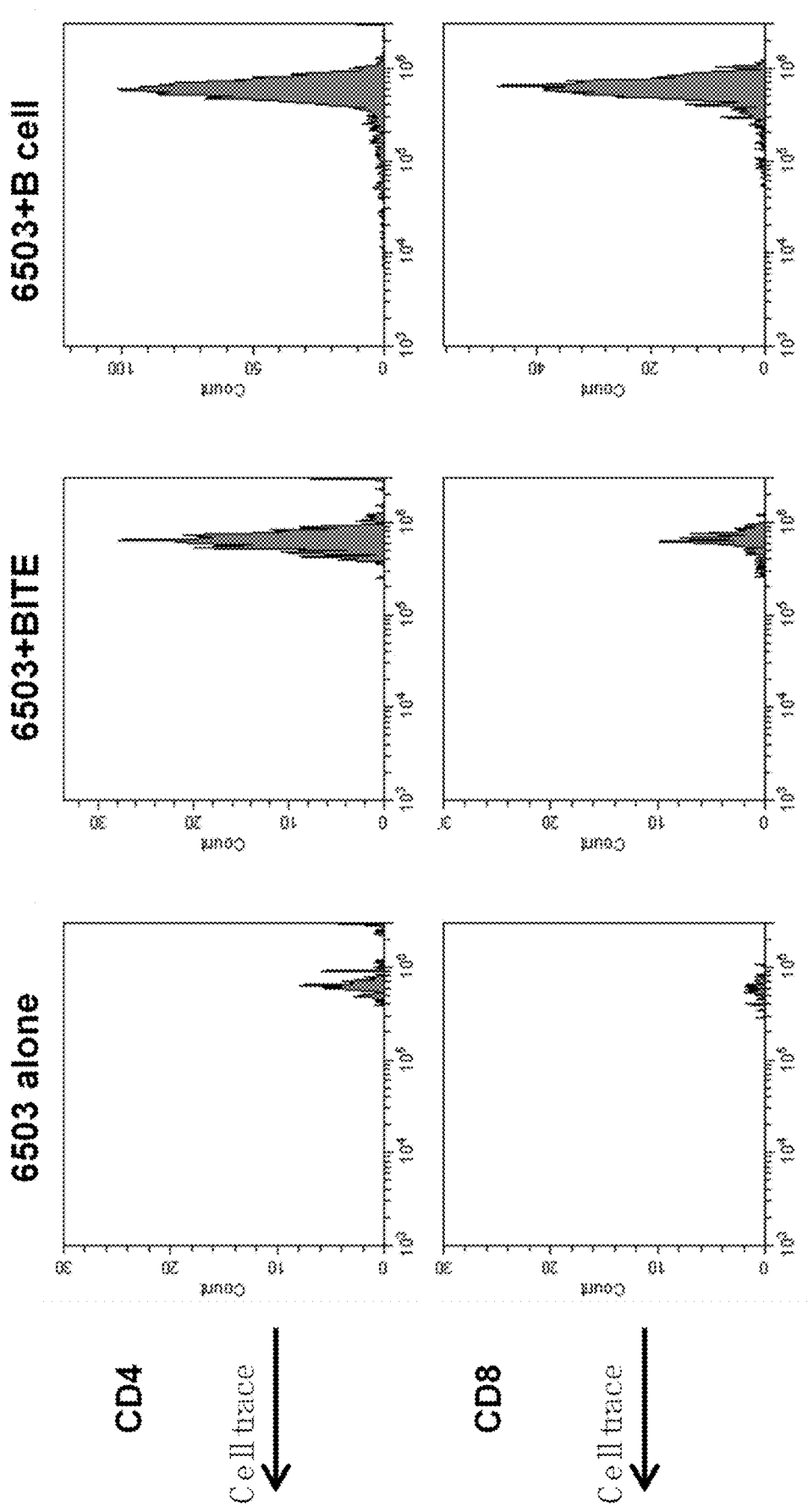
FIG. 14 shows CellTrace™ analysis of 6503 cells (i.e., ACPP CART cells) co-cultured with B cells in the presence or absence of CD3-CD19 bispecific antibody.
Figure 15:
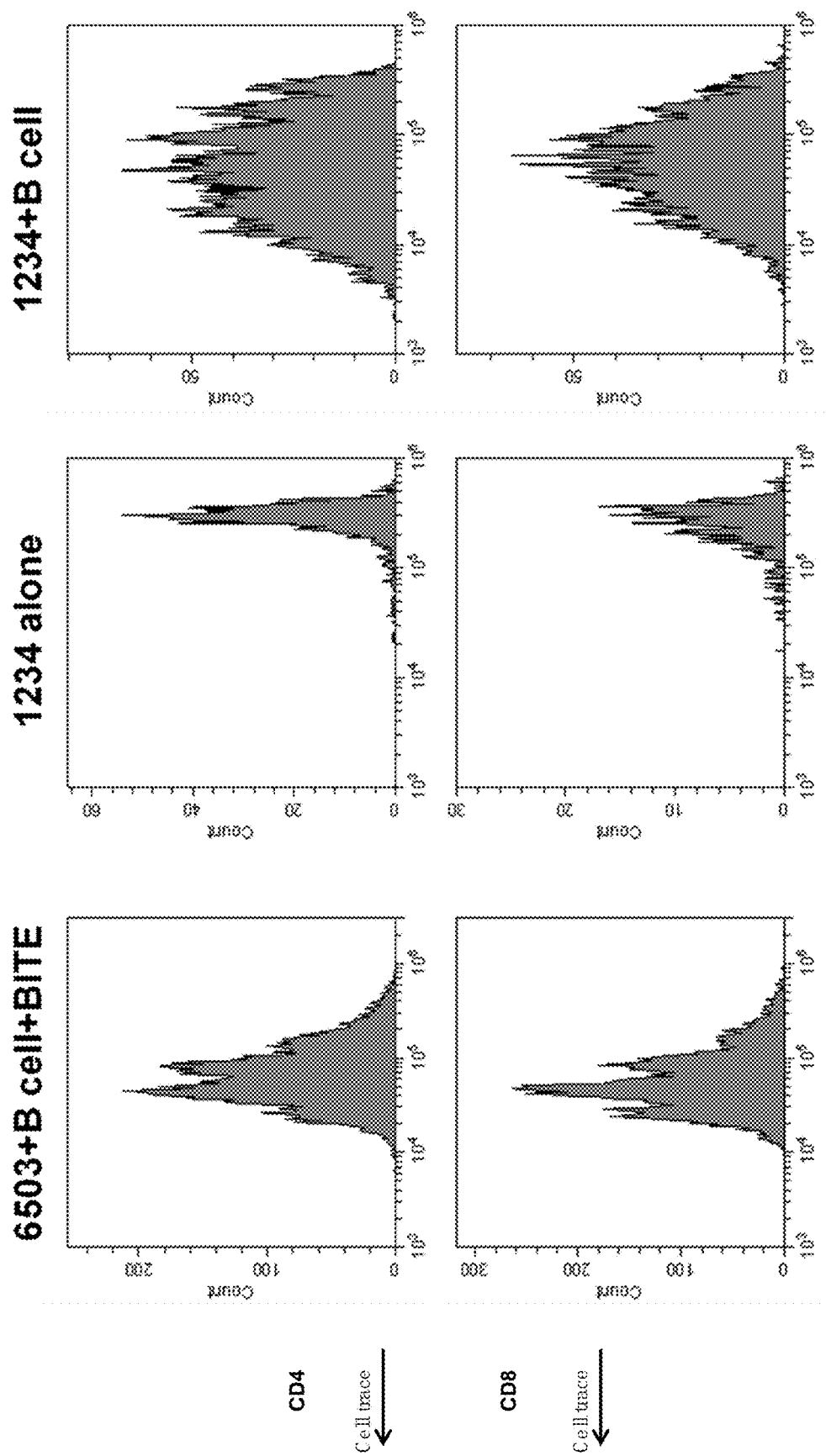
FIG. 15 shows CellTrace™ analysis of 6503 cells co-cultured with B cells in the presence or absence of CD3-CD19 bispecific antibody.
Figure 16A:
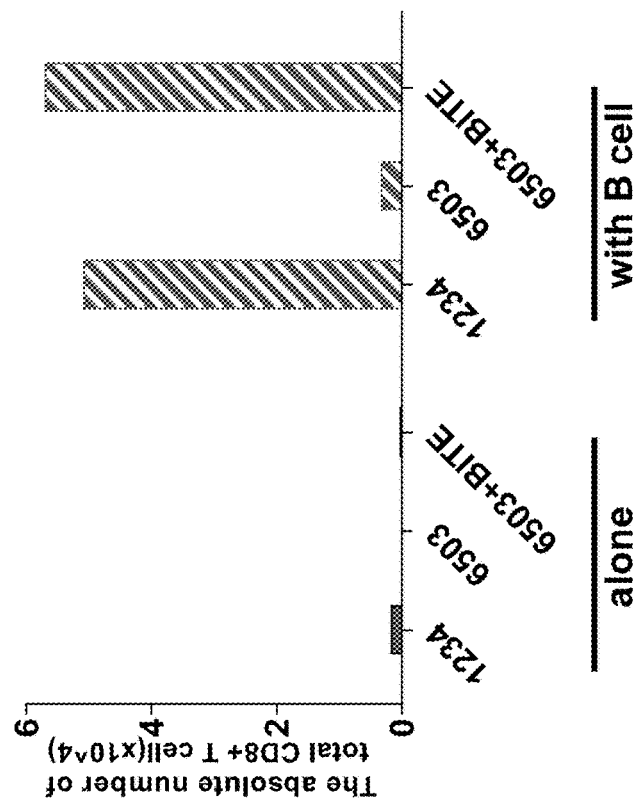
FIGS. 16A and 16B show CellTrace™ analysis of 6503 cells co-cultured with B cells in the presence or absence of CD3-CD19 bispecific antibody.
Figure 16B:
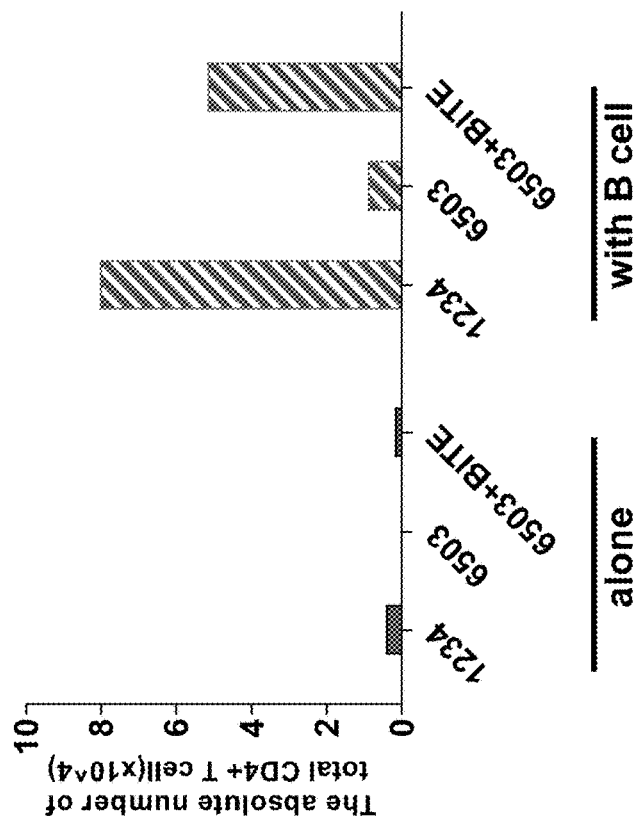
Figure 17A:
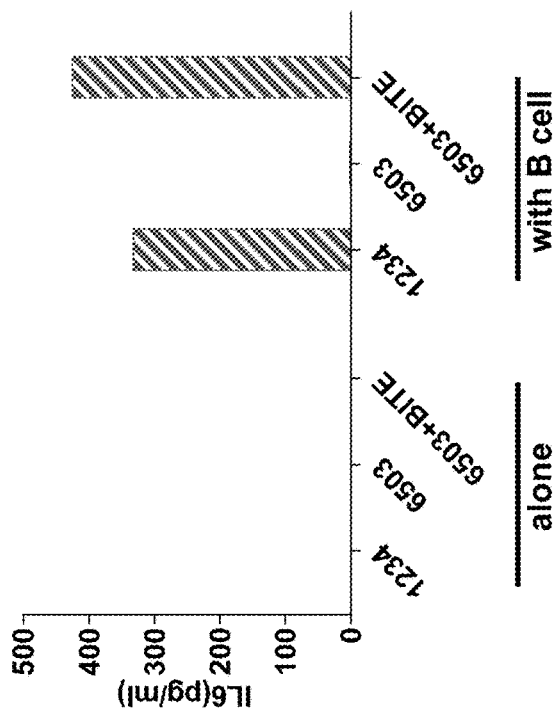
FIGS. 17A, 17B, 17C, and 17D show cytokine release results of CAR T cells co-cultured with B cells in the presence or absence of CD3-CD19 bispecific antibody.
Figure 17B:
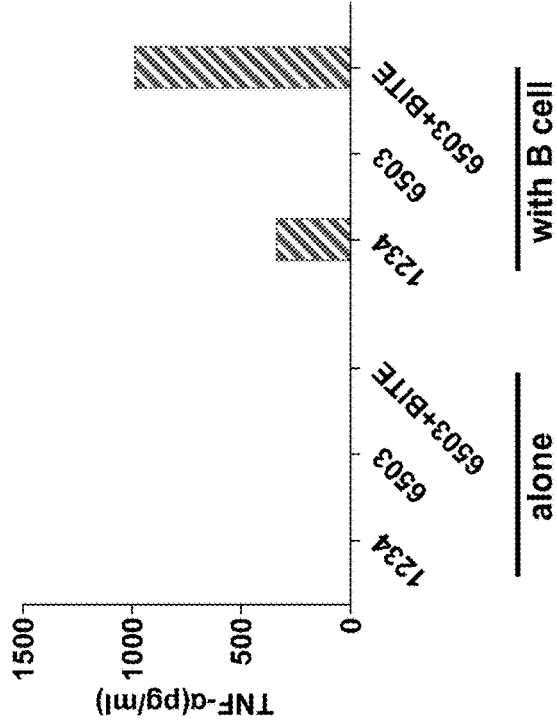
Figure 17C:
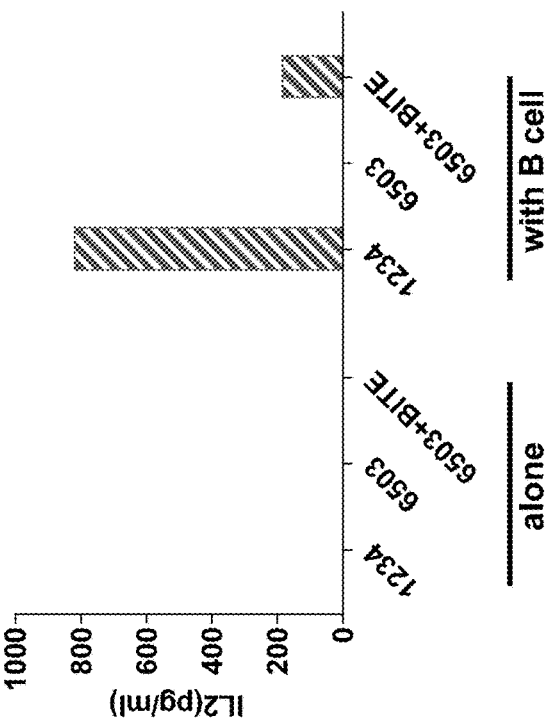
Figure 17D:
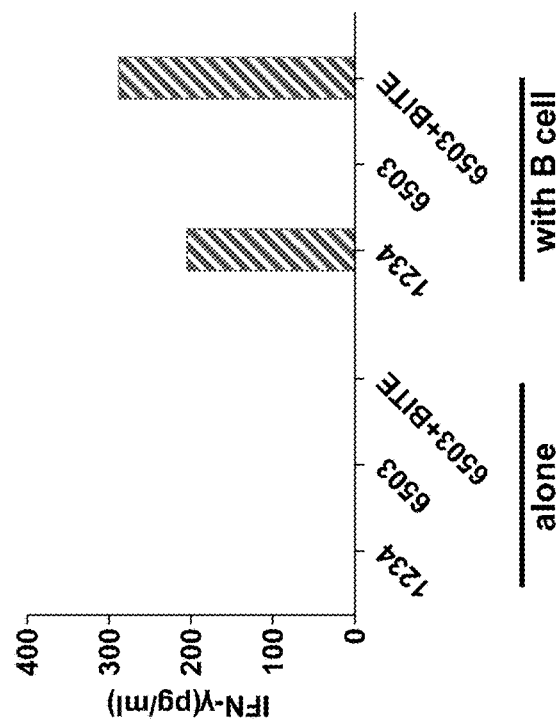
Figure 18:
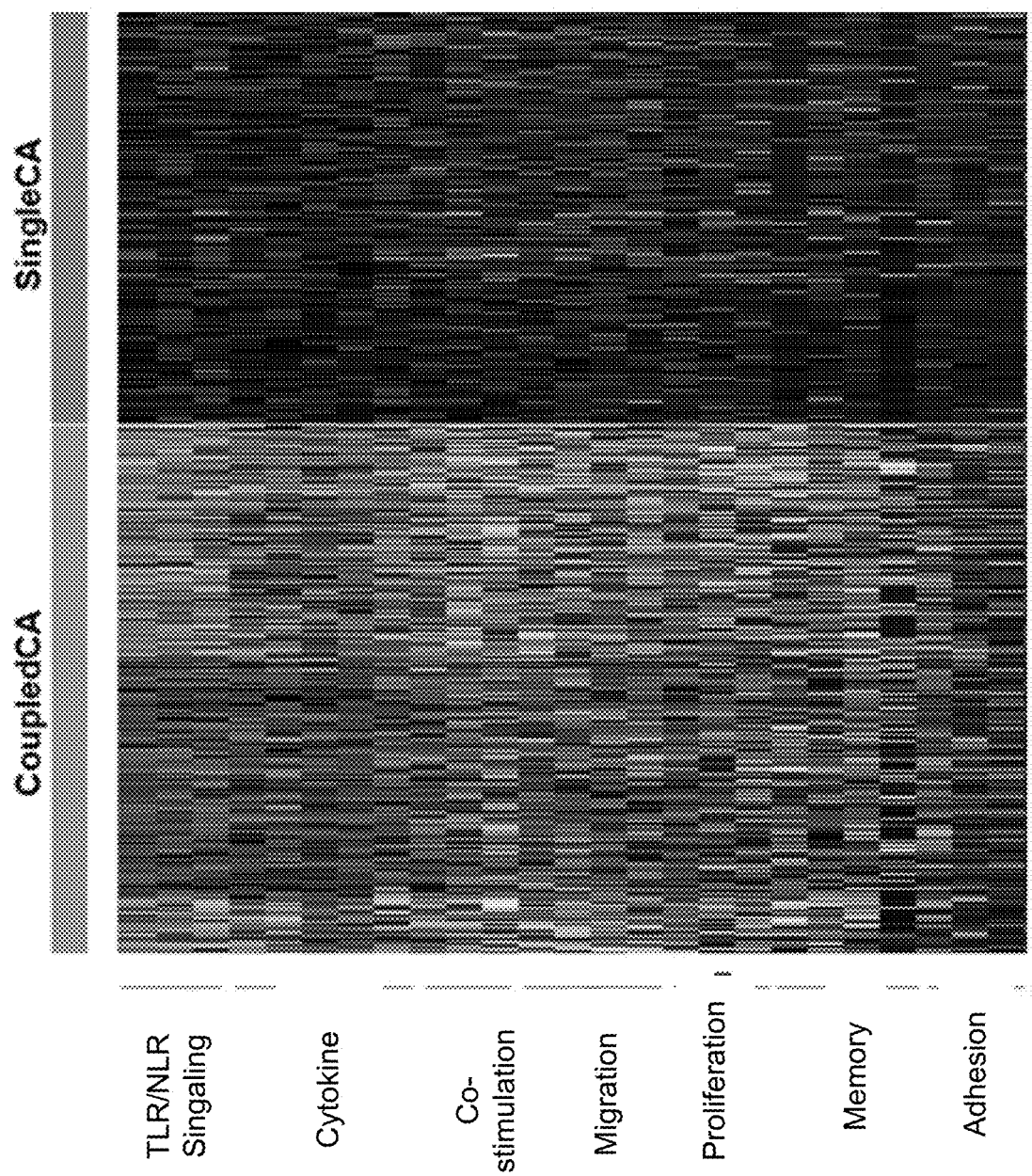
FIG. 18 shows gene expression profiling results of single-cell RNA (scRNA) analysis.
Figure 19:
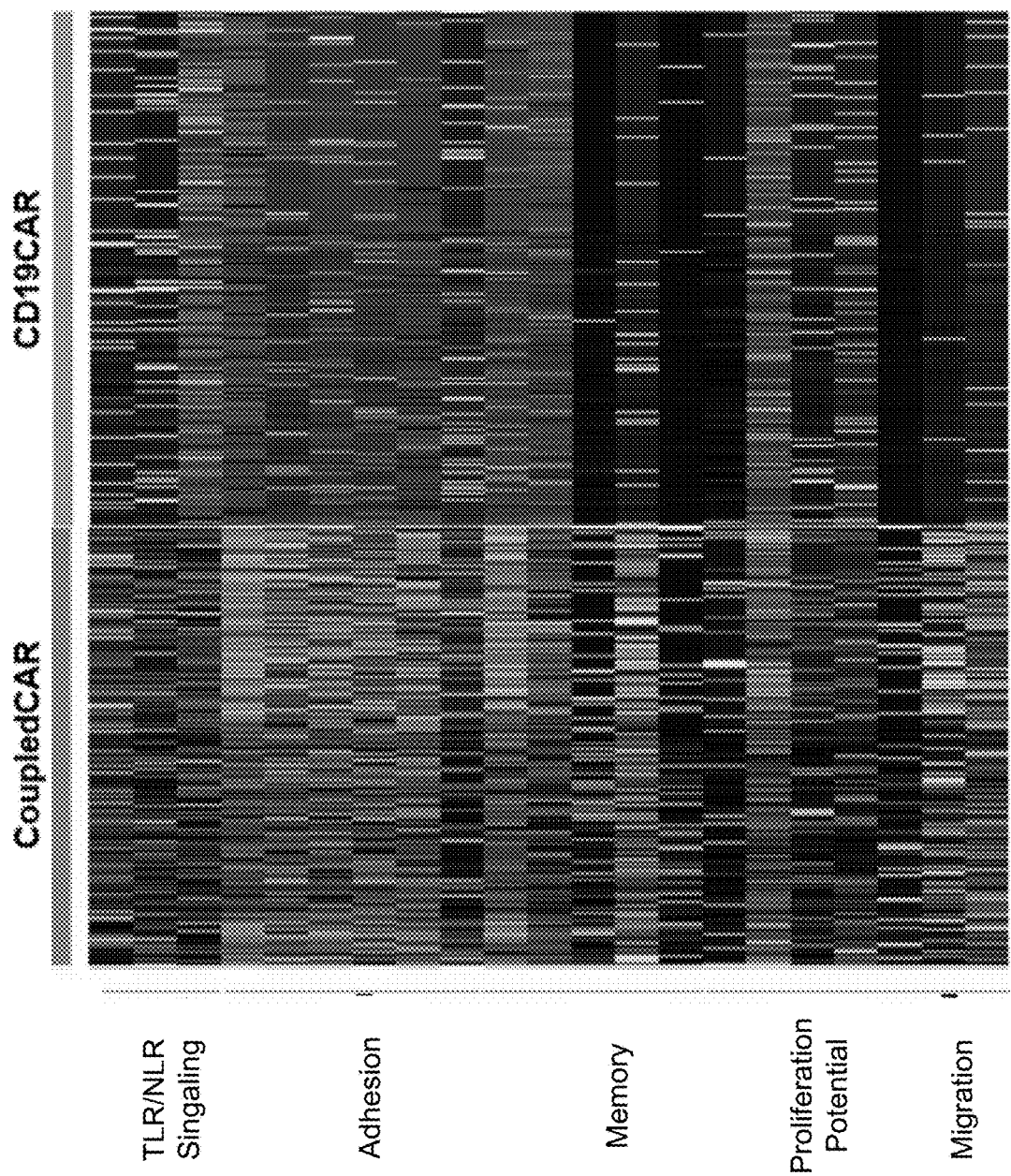
FIG. 19 shows gene expression profiling results of scRNA analysis.

FIGS. 14-16 show CellTrace™ analysis of the 6503 cells co-cultured with B cells in the presence or absence of CD3-CD19 bispecific antibody. 6503 cells alone or co-cultured with B cells were mixed with CD3-D19 bispecific antibody for 120 hours, and cell proliferation analysis was performed using CellTrace™. 1234 cells were used as a positive control. It was observed that neither the bispecific antibody nor the B cells alone could expand the T cells, while CD3-CD19 bispecific antibody caused the T cells co-cultured with B cell to be expanded.

FIG. 17 shows cytokine release results of CAR T cells co-cultured with B cells in the absence and presence of CD3-CD19 bispecific antibody. 6503 cells alone or co-cultured with B cells were mixed with CD3-CD19 bispecific antibody for 24 hours and then were analyzed using Cytometric Bead Array (CBA). 1234 cells were used as a positive control. It was observed that neither CD3-CD19 bispecific antibody alone nor B cells alone could make 6503 cells release cytokines, while 6503 cells co-cultured with B cells and CD3-CD19 bispecific antibody released cytokines. For example, the released cytokines included IL2 to promote activation and proliferation of T cells and IL6, TNF-α, and IFN-γ to provide an inflammatory environment. Thus, these results show that CD3-CD19 bispecific antibody can cause solid tumor CAR T cells (e.g., PAP CAR T cells) to be expanded, similar to the CD19 CAR T cells were in the previous Examples.

Figure 20:
FIG. 20 shows B cell clustering 24 hours after CD19 CART cells and PAP CAR T cells were co-cultured with these B cells.
Figure 21:
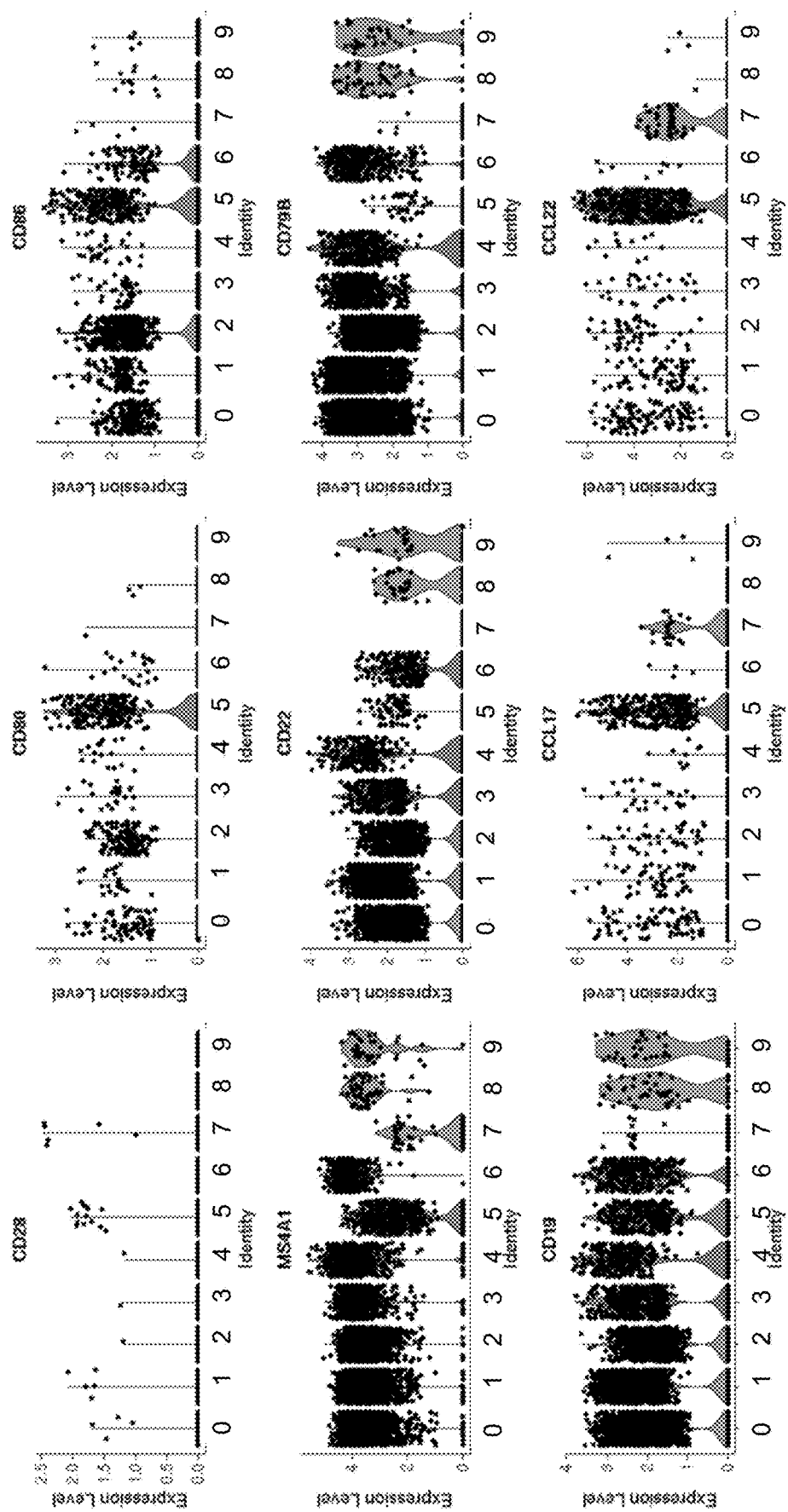
FIG. 21 shows the expression of surface markers of the B cells.
Figure 22:
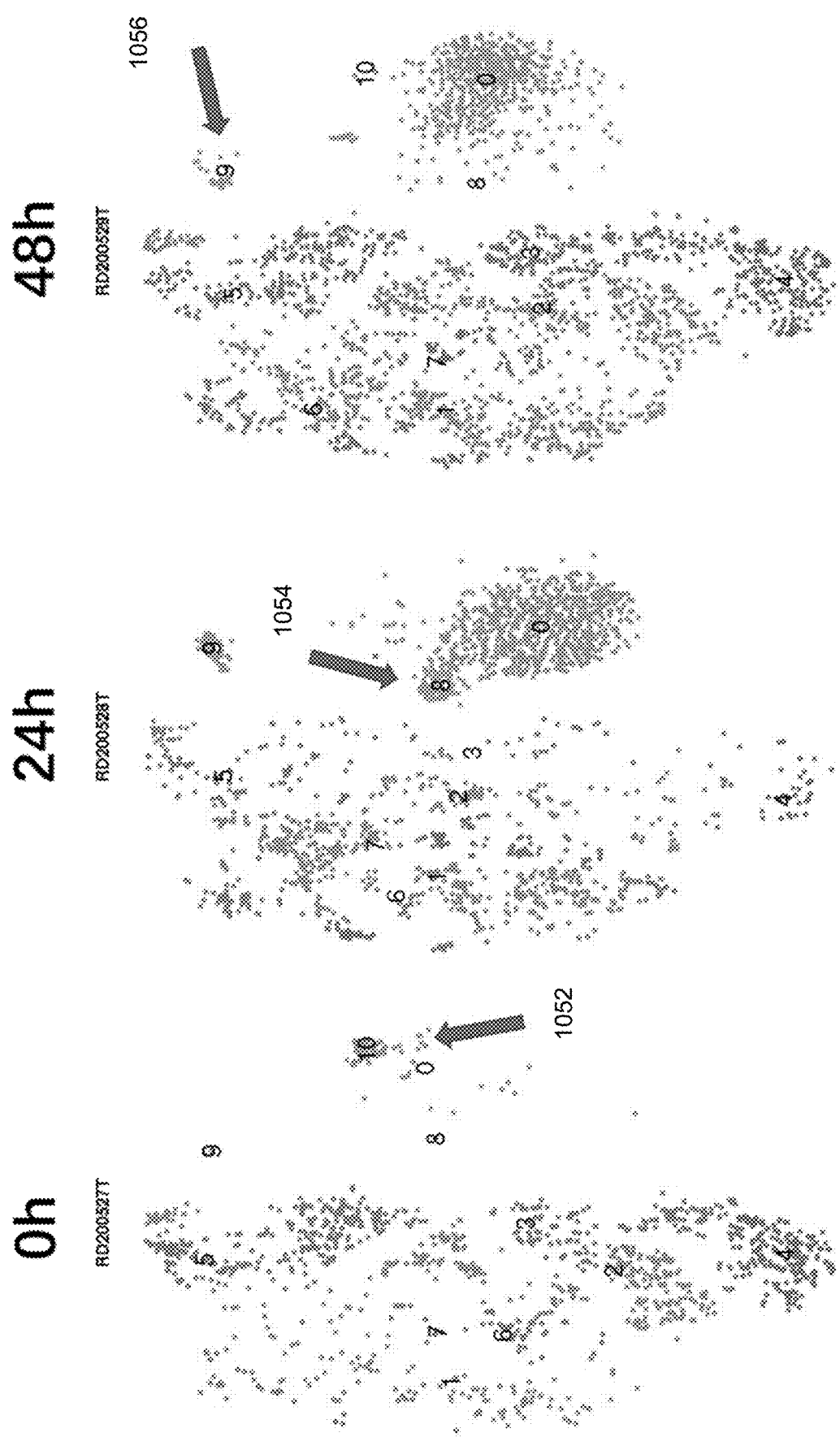
FIG. 22 shows PAP CART cells clustering 24 and 48 hours after CD19 CART cells and PAP CAR T cells were co-cultured with B cells.

Further, CD19 CART cells and PAP CART cells were co-cultured with B cells for 24 or 48 hrs (hours), and single cell RNA (scRNA) profiling assay was performed on T cells, including both CD19 CART cells and PAP CAR T cells as well as B cells. FIG. 20 shows B cell clustering 24 hours after CD19 CART cells and PAP CART cells were co-cultured with these B cells. Two clusters of B cells were found in the 24 hrs samples: BC5 and BC7 clusters. Further analysis was performed to identify the phenotypes of the B cells. FIG. 21 shows the expression of surface markers of the B cells. It appears that the cells of BC5 and BC7 were in an activated state: BC5 differentiating towards BC7, and BC7 differentiating towards plasma cell, but not fully differentiated into plasma cells. FIG. 22 shows PAP CAR T cells clustering 24 and 48 hrs after CD19 CART cells and PAP CART cells were co-cultured with B cells. It appears that, as compared to 0 h, 24 hrs and 48 hrs showed enrichment of multiple CAR T cells, including Cluster 0 (C0) and Cluster 1 (C1). The expansion cluster in CD19 CAR T cells is C0; the expansion clusters in PAP CAR T cells are C0 and C1; and the expansion clusters in NT cells are C2, C4, and C10. C10 appeared to be similar to C0. It is speculated that C0 was differentiated from C10. Both groups of cells are CD4/CD8 double negative. The proliferation of CD19 CAR T cell groups has low interaction with B cells; PAP CAR T cells of C1 and NT cells of C2 appear to interact with B cells. FIG. 23 shows highly expressed genes in PAP CAR T cells in CB1. For example, CCR4 is highly expressed in C1, and CCL17 and CCL22 bound to CCR4 were found to be highly expressed in B cells of C5. The interaction of the B cells and CAR T cells activates the JAK-STAT pathway, thereby inducing expansion of PAP CAR T cells, which is consistent with B cell ligand expression (CCL17 and CCL22) as shown in FIG. 23.

In sum, these results indicate several mechanisms involved in a CoupledCAR® system, which are shown in FIGS. 20-22. As shown in FIG. 20, B cells can be activated and become differentiated B cells, of which the expression of surface markers is shown in FIG. 21. The activation and differentiation of B cells can be implemented by various methods, for example, by using CD19 CART cells, CD19 antibody, bispecific antibody (e.g., CD3-CD19/BCMA), cytokines (e.g., IL4). T cells, including solid tumor CART cells, can also be activated to release cytokines to activate other APCs and DCs, and some B cells can be lysed, thereby releasing cell debris. These released cytokines and debris can activate APCs, including B cells and DCs. These APCs can upregulate co-stimulation molecules or ligands such as CD40, which can interact with T cells to cause or induce the expansion of T cells without corresponding binding antigens. Also, the interaction between differentiated B cells and T cells can cause or induce activation or expansion of T cells.

CoupledCAR®: Single-Cell RNA-Sequencing Analyses of Tumor Tissue from a Colorectal Cancer Patient with Thyroid Cancer after CAR T Cells Infusion CAR T cell therapy in solid tumors is limited by various intrinsic and extrinsic factors, including poor expansion and a low degree of infiltration to the tumor site. The limitation of CAR T cell expansion against difficult-to-treat solid tumors has been recently addressed. To confirm CAR T cell infiltration into a solid tumor, deep single-cell RNA sequencing on T cells isolated from tumor tissue (lung metastasis) and on adjacent peripheral blood (PB) from a patient with thyroid cancer was performed. This study was also designed to depict the baseline landscape of infiltrating CAR T cells, especially the TSHR CAR T cells in thyroid cancer.

The T cells in this study included CAR-negative T cells (normal T cells) and CAR-positive T cells, which consisted of CD19 CART cells (CD19 CAR), TSHR CART cells (TSHR CAR), and T cells incorporated with both of the two CAR constructs (a CoupledCAR® system). These CAR-positive T cells in tumor tissue were predominantly TSHR CAR T cells and have shown a significant proportion of proliferative and cytotoxic T cells, which was evidenced by the signature gene expression.

Subsequently, a group of TSHR CART cell infiltration was observed. These cells also showed a high degree of cytotoxicity and trafficking activity, characterized by the high expression of known functional markers. Additionally, a large diversity of TSHR CAR T cell clones in tumor tissue was observed, which was different from TSHR CAR T cell clones in PB. The inferred developmental trajectory of CAR-positive CD8 T cells in PB and tumor tissue indicate that CAR T cell products described herein can undergo extensive transitions.

Figures 24A, 24B:
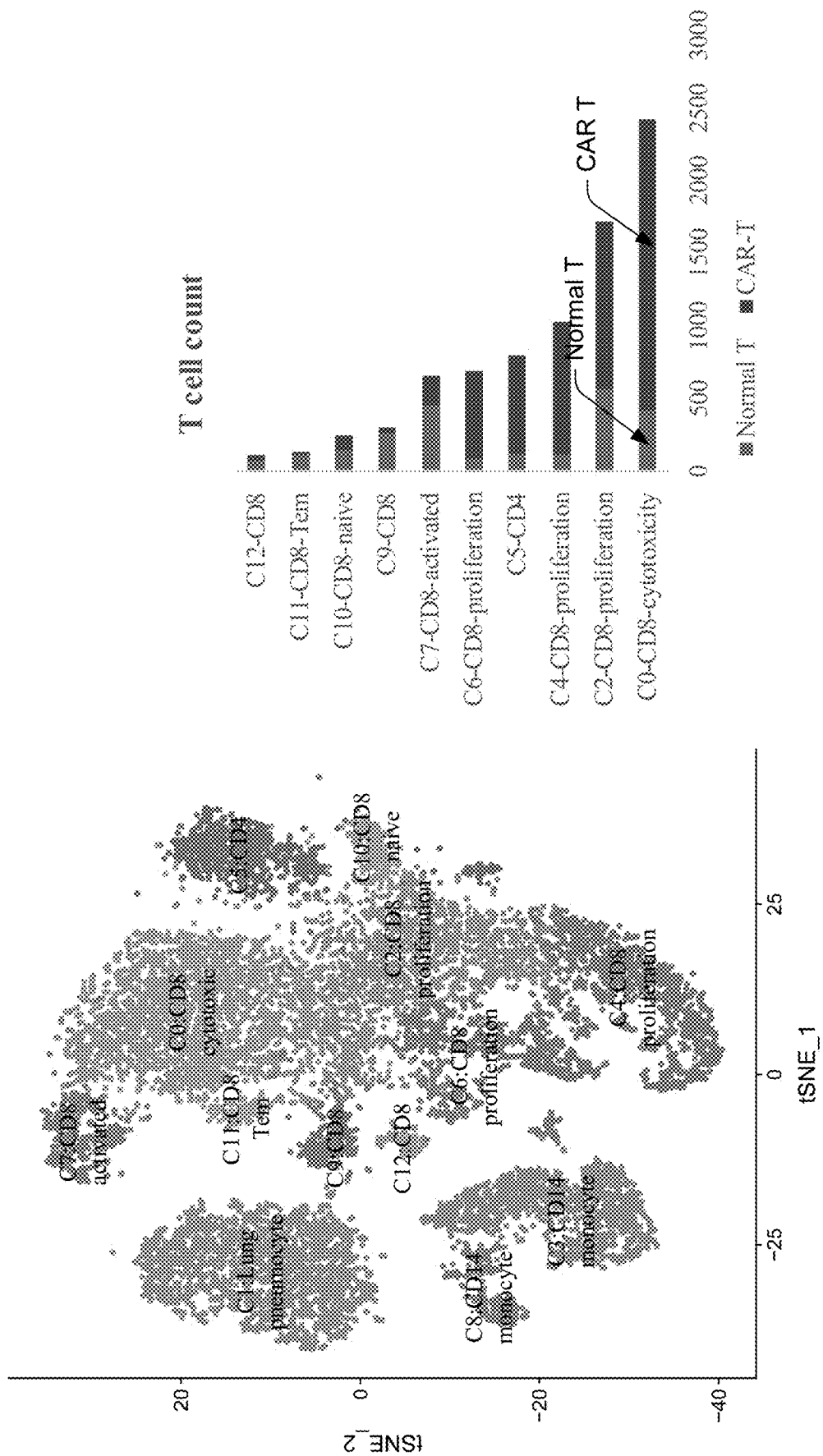
FIGS. 24A and 24B show that T cells derived from both peripheral blood (PB) and tumor tissue of a colorectal cancer patient with thyroid cancer are capable of robust proliferation and cytotoxicity.

FIGS. 24A and 24B show that T cells derived from both PB and tumor tissue of a colorectal cancer patient with thyroid cancer are capable of robust proliferation and cytotoxicity. These data are restricted to T cells, including TSHR CAR, CD19 CAR, the CoupledCAR® system, and normal T cells. The integrated expression datasets derived from both peripheral blood (PB) and tumor tissue (lung metastasis) of the patient were applied to dimensional reduction analysis (t-SNE). Ten T cell clusters, including clusters of CD8 (proliferation, cytotoxicity, naïve, and effector memory), were identified. FIG. 24B. These clusters appear to be almost exclusively proliferative and cytotoxic T cells. There were 3447 proliferative T cells, and 77.7% of which were CAR-positive T Cells. There were 2431 cytotoxic T cells, and 82.8% were CAR-positive. These results show most of these CAR-positive T cells are cytotoxic and proliferative T cells, providing compelling evidence of the proliferative and antitumor capacity of the CAR T products described herein.

Figure 25:
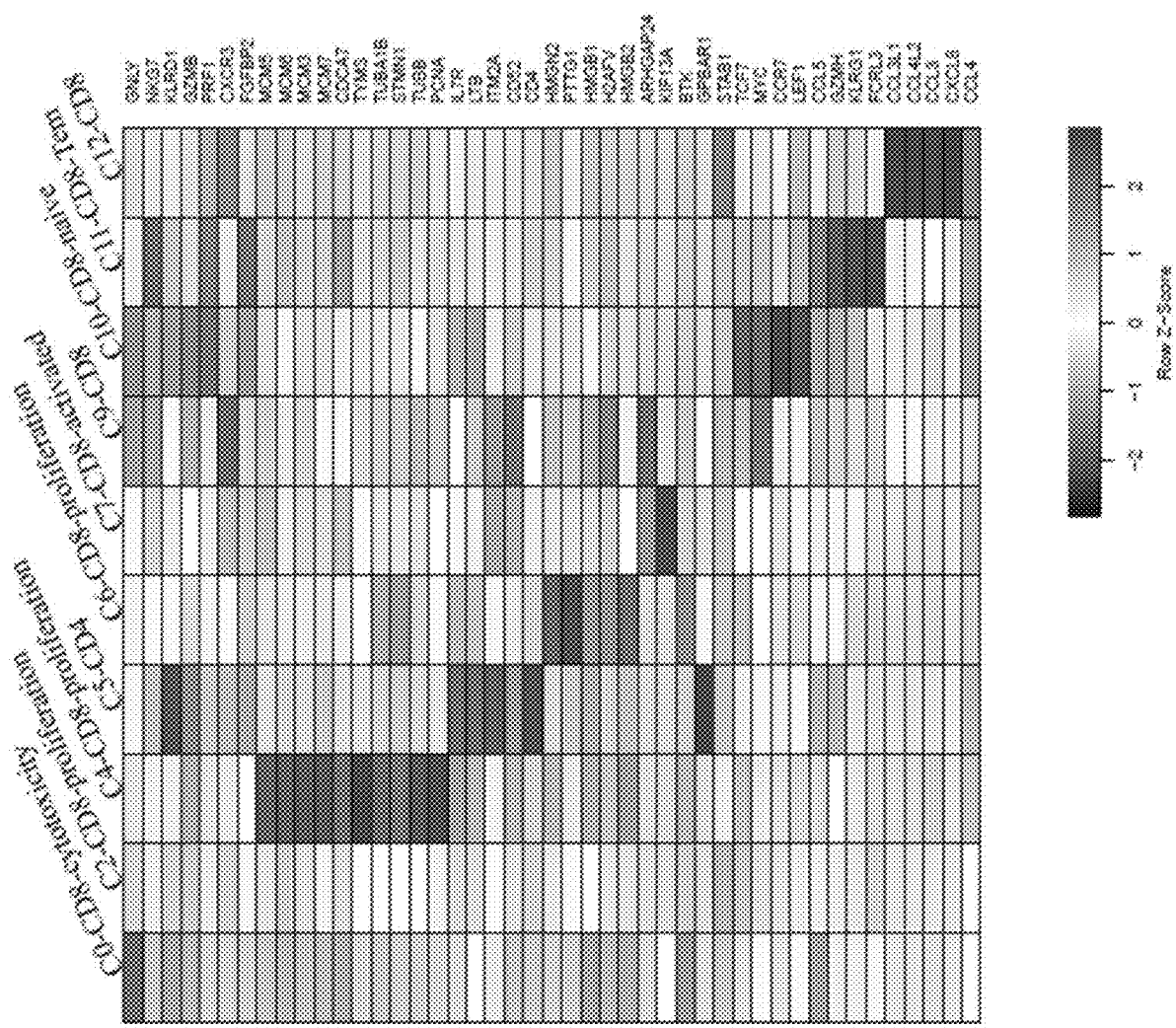
FIG. 25 shows that identification of all T cell clusters in PB and tumor tissue was evidenced by the expression of signature genes and known functional markers.

FIG. 25 shows that identification of all T cell clusters in PB and tumor tissue was evidenced by the expression of signature genes and known functional markers. These data are restricted to T cells, including TSHR CAR, CD19 CAR, the CoupledCAR® system, and normal T cells. Dynamic changes in gene expression between T cell clusters in peripheral blood (PB) and tumor tissue (lung metastasis) have been identified and were used for cluster analysis. It was observed that cytotoxic T cells in the C0 cluster were characterized by high expression of genes associated with cytotoxicity, including GNLY, GZMB, PRF1, CXCR3, and FGFBP2. Genes involved in the "cell cycle" and "proliferation" pathways, such as TYM, STMN1, MCM, HMGB1/2, and HMGN2, were highly expressed in corresponding clusters CD8-proliferation (C2, C4, C6). A well-defined subset of naïve T cells (C10) showed high expression of naïve markers (TCF7, CCR7, LEF1). Accordingly, the high expression of chemokines in the C12 cluster supported the potential migratory feature of these T cells.

FIGS. 26A-26C show that TSHR CAR T cells are significantly enriched in tumor tissue, confirming the capacity of CAR T cell infiltration into the tumor. These data are restricted to just TSHR CAR T cells. FIG. 26A. A total of 4670 single cells, including three subtypes, were isolated in the tumor tissue of the patient, among which pneumocytes accounted for 40.5%, monocytes for 14.5%, and T cells for 45.0%. FIG. 26B. CAR-positive T cells derived from tumor tissue appeared to be almost exclusively proliferative and cytotoxic T cells. FIG. 26C. The statistics of the TSHR CAR T cells in tumor tissue were compared with peripheral blood (PB) from the patient. TSHR CAR T cells in PB comprises 19.20% of T cells and 22.36% of CAR-positive T cells. Significant increases in levels of TSHR CAR T cells (38.38% of T cells and 70.60% of CAR-positive T cells) in tumor tissue, with an increase by a factor of 2-3 as compared with PB, was observed. CD19 CAR T cells were not enriched in tumor tissue (data not shown). These results show TSHR CART cells are significantly enriched in tumor tissue which confirms the capacity of CAR T cell infiltration into the tumor, and it is not surprising that tumor cells in the tumor tissue were not detected by deep single-cell RNA sequencing, given that the antitumor response against solid tumor-associated with cytotoxicity of the CART cells described herein.

FIGS. 27A-27D shows rare clonotype was found to be shared by TSHR CAR T cells in PB and tumor tissue. These data are restricted to just TSHR CAR T cells. FIG. 27A. 1055 and 501 TSHR CAR T cell clones in PB and tumor tissue, respectively, were identified. Only two clones with identical TCRs were detected. FIG. 27B. Only three clonotypes were present in at least two TSHR CAR T cells from PB. FIG. 27C. No clonotype was enriched in the TSHR CAR T cells from tumor tissue. FIG. 27D. One clonotype was found to be shared by TSHR CAR T cells in PB and tumor tissue. These results show one clonotype was found to be shared by TSHR CAR T cells in PB and tumor tissue, indicating diversity of TSHR CAR T cell clones between PB and tumor tissue.

Figures 28A, 28B:
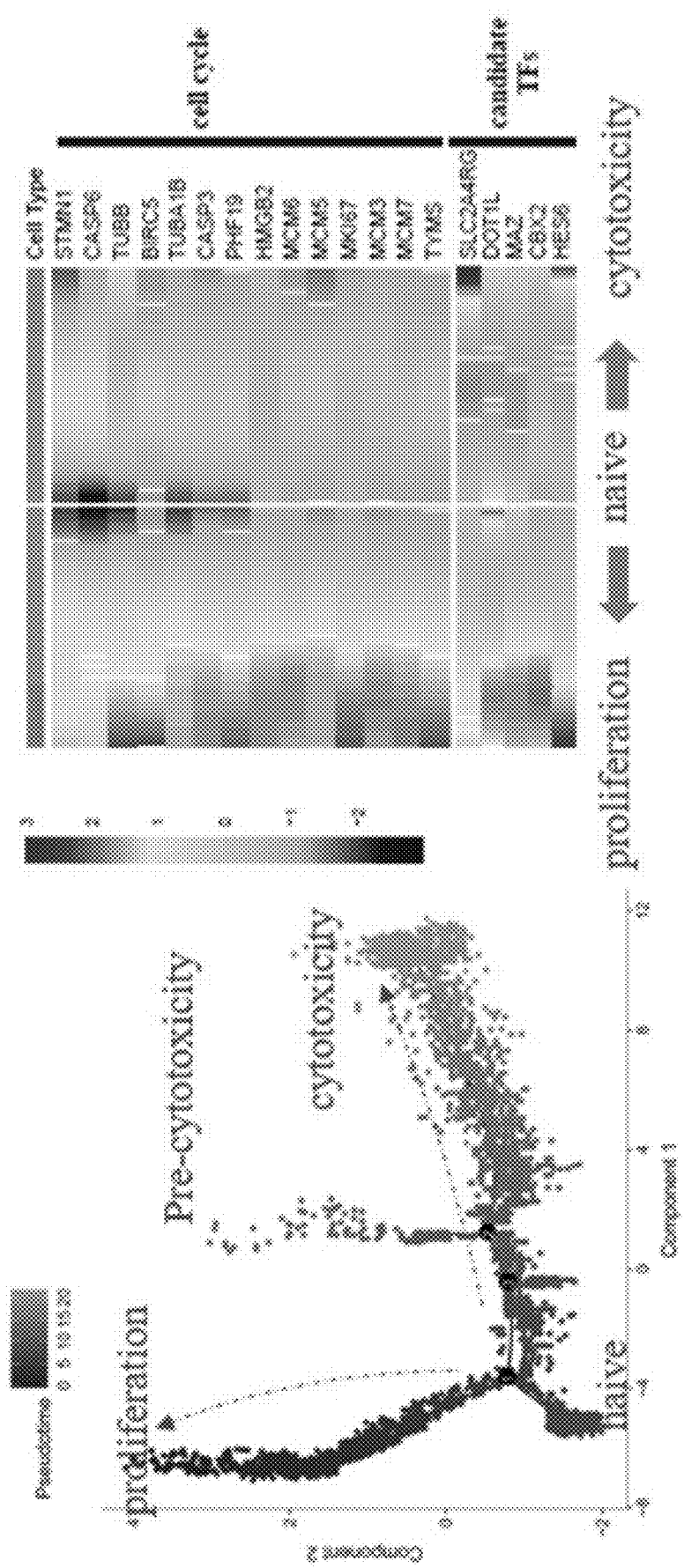
FIGS. 28A, 28B, 28C, and 28D show an inferred developmental trajectory of CAR+CD8 T cells in PB, suggesting a branched structure with differentiated proliferation and cytotoxicity of T cells.
Figures 28C, 28D:
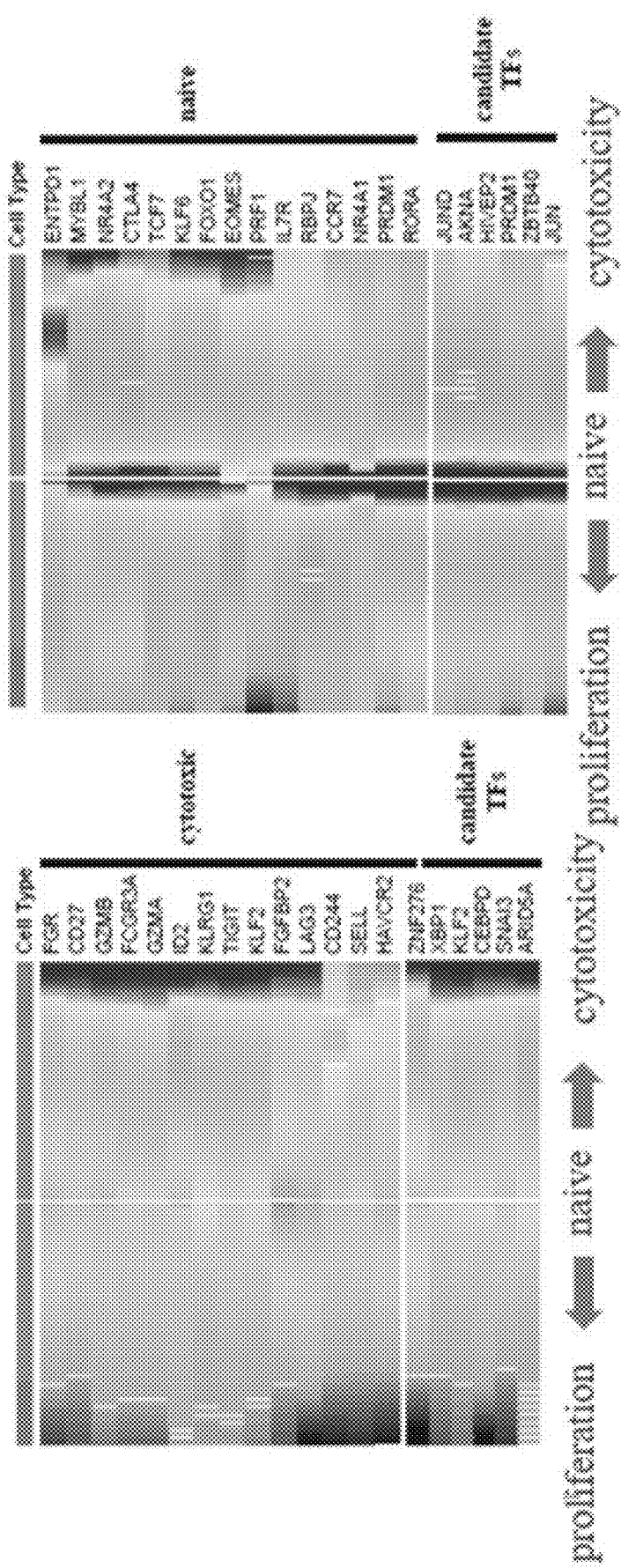

FIGS. 28A-28D shows an inferred developmental trajectory of CAR-positive CD8 T cell in PB suggested a branched structure with differentiated proliferation and cytotoxicity T cells. These data are restricted to all CAR-positive CD8 T cells. FIG. 28A. The branched trajectory of CAR-positive CD8 T cell state in PB transited in a two-dimensional state-space with arrows showing the increasing directions of certain T cell properties. According to the original state labeled as the naïve T cells, differentiated T cells could be classified as proliferation and cytotoxicity, which undergo two distinct state transitions. FIGS. 28B, 28C, and 28D. Highly expressed signature genes exhibited distinct expression patterns among the corresponding three CD8 clusters: proliferative T cells with high expression of proliferation-related genes, naïve T cells with high expression of naive-related genes, cytotoxic T cells with high expression of cytotoxicity-related genes. These results show CAR-positive CD8 T cells in PB will be differentiated into two different fates: proliferation and cytotoxicity. Cell fate decisions are regulated by the high expression of signature genes.

Figures 29A, 29B:
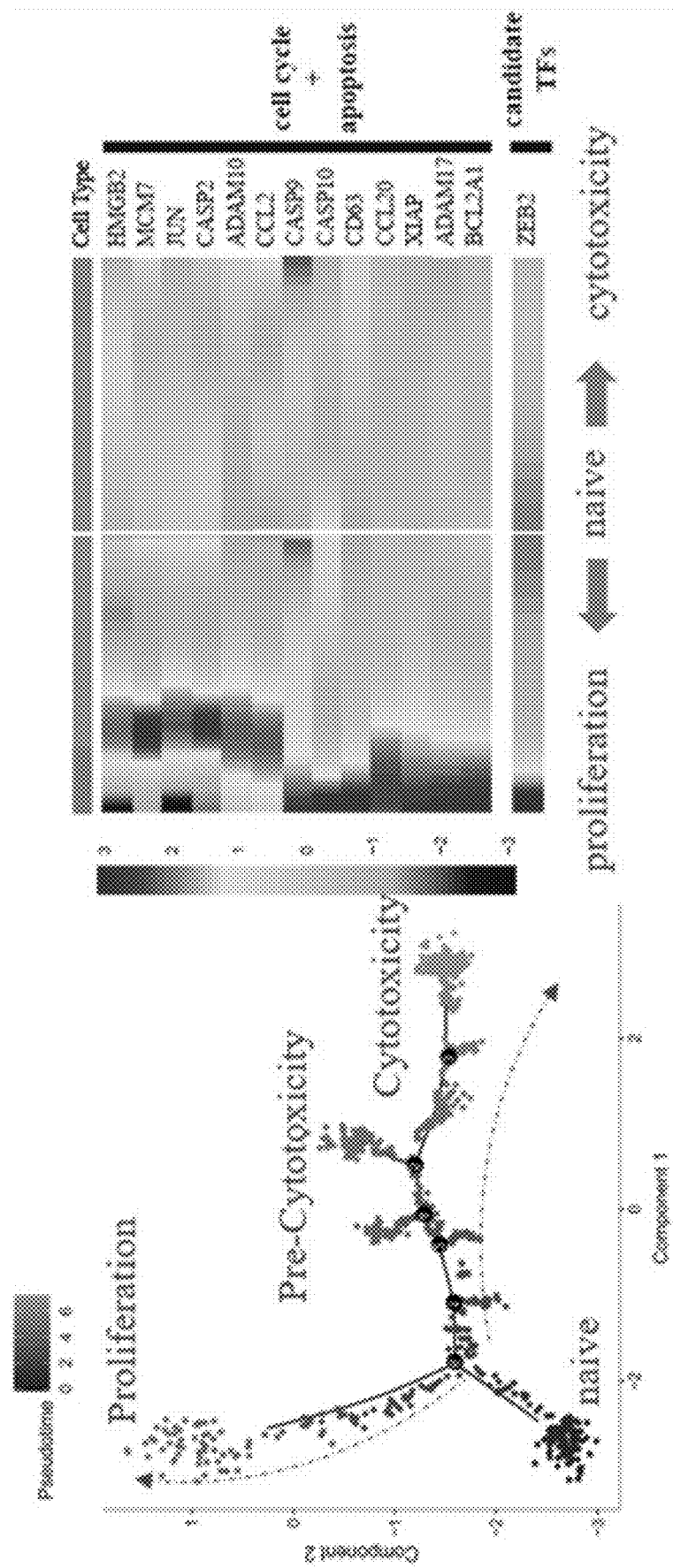
FIGS. 29A, 29B, 29C, and 29D show another inferred developmental trajectory of CAR+ CD8 T cell in tumor tissue suggesting a branched structure with differentiated proliferation and cytotoxicity of T cells.
Figures 29C, 29D:
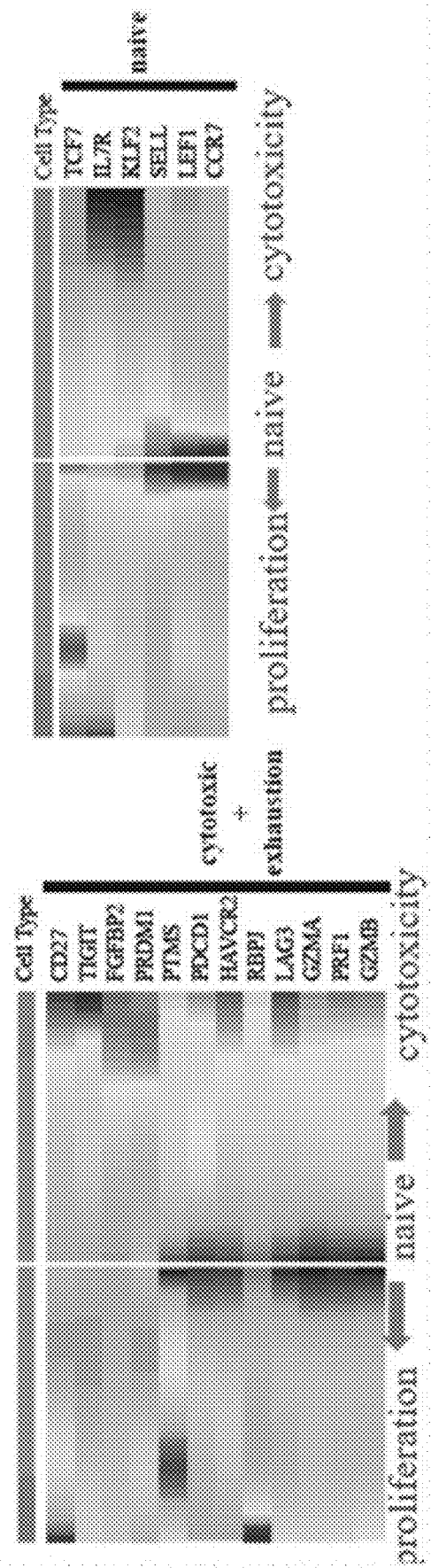

FIGS. 29A-29D shows another inferred developmental trajectory of CAR-positive CD8 T cells in tumor tissue, suggesting a branched structure with differentiated proliferation and cytotoxicity T cells. These data are restricted to CAR-positive CD8 T cells. FIG. 29A. The branched trajectory of CAR-positive CD8 T cell state in tumor tissue transited in a two-dimensional state-space with arrows showing the increasing directions of certain T cell properties. According to the original state labeled as the naïve T cells, differentiated T cells could be classified as proliferation and cytotoxicity, which undergo two distinct state transitions. FIGS. 29B, 29C, and 29D. Highly expressed signature genes exhibited distinct expression patterns among our corresponding three CD8 clusters: proliferative T cells with high expression of proliferation-related genes, naïve T cells with high expression of naive-related genes, cytotoxic T cells with high expression of cytotoxicity-related genes. As well as T cells in PB, two subtypes of differentiated CAR-positive CD8 T cells with properties of proliferation and cytotoxicity were present in tumor tissue. The proliferative T cells appeared to exhibit high degrees of expansion in vivo, and cytotoxic T cells displayed profound antitumor activity.

Figure 30:
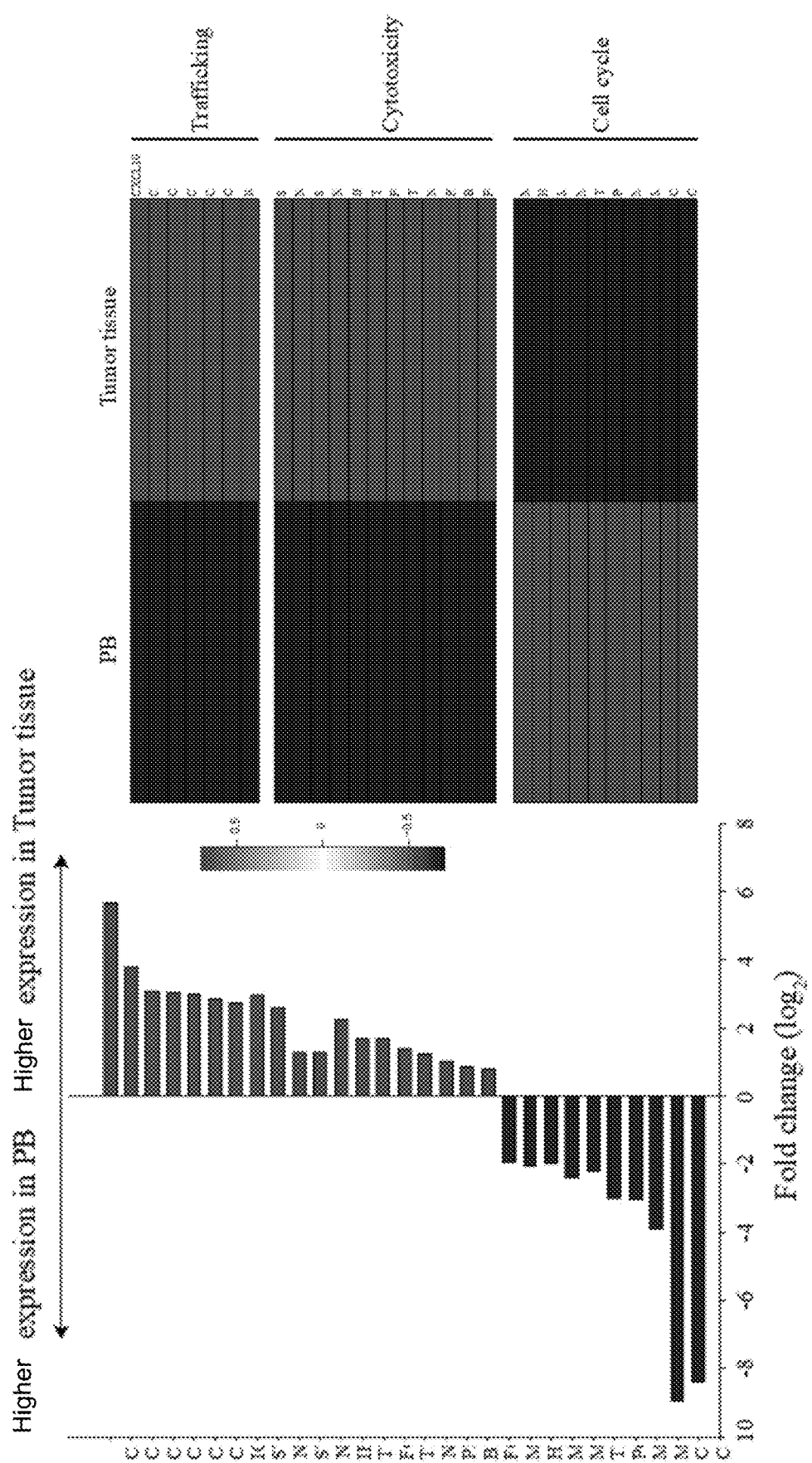
FIG. 30 shows TSHR CAR T cells in tumor tissue exhibited a higher degree of trafficking and cytotoxicity, as compared with TSHR CAR T cells from PB.

FIG. 30 shows TSHR CAR T cells in tumor tissue exhibited a higher degree of trafficking and cytotoxicity, as compared with TSHR CAR T cells from PB. These data are restricted to just TSHR CAR T cells. Differential expression analyses of RNA-sequencing data of TSHR CAR T cells from PB and tumor tissue were performed and showed higher expression of trafficking-related and cytotoxicity-related genes in tumor tissue as compared to TSHR CAR T cells in PB. Cell cycle-related genes were being expressed at a higher level in PB. TSHR CAR T cells in tumor tissue exhibited a higher degree of trafficking and cytotoxicity, as compared with TSHR CAR T cells from PB.

Deep single-cell RNA sequencing was applied to a lung sample of the patient with thyroid cancer and characterized the T cell landscaping, especially the TSHR CAR T cells, which showed a significant proportion of proliferative and cytotoxic T cells in tumor tissue. Multiple comparisons between TSHR CAR T cells in PB and tumor tissue were performed and indicated that TSHR CAR T cells in tumor tissue had a higher capacity of cell infiltration, trafficking, and cytotoxicity as compared to TSHR CAR T cells in PB. These findings provide a plausible explanation for the positive responses of TSHR CAR T cells to immunotherapies for thyroid cancer. Additionally, CAR T cell products described herein might undergo extensive state transitions, which appeared to be shaped by two distinct processes, the CAR T cells proliferation, and tumor-induced CAR T cells cytotoxicity. Overall, this large compendium of single-cell data can elucidate the tumor-immune interactions by providing insights into the composition, states, and dynamics of CoupledCAR® T cell products in thyroid cancer. This approach for high-dimension and high-resolution characterization of single immune cells are applicable to other types of cancer and the use of other products for treating different types of cancer.

Based on the results from single-cell RNA profiling, multiple molecules were identified that appeared to enhance or weaken the performance of T cells (e.g., levels of T cell response), and the following molecules were selected from the multiple molecules for further investigation including overexpression based on previous studies and reports: JAK2, STAT1, STAT2, STAT3, STAT4, PRKCA, PRKCQ, MAP3K1, MAP3K4, MAP3K8, MAPK14, BRAF, SMAD5, IL2RB, IL12RB2, IL18R1, IL21R, IL7R, CD28, Cavin3, ZBED2, MYC, EGFR, HER2, HER3, HER4, VEGFR2, VEGFR3, PDGFRα, PDGFRβ, gp130, IL-23R, IL-7R, CRLF2, βc, GHR, THPOR, EPOR, LepR, CSF3R, TNFR1, TGFBR1, TGFBR2, ACVR1A, BMPR2 ACVR1B, CXCR1, CXCR2, CXCR3, CXCR4, CCR2, and CCR5; and/or (knock out or knockdown) TOX, TOX2, TOX4, NR4A2, and NR4A3. For example, further studies specified the performance of T cells with modulation of Cavin3, ZBED2, MYC, TOX, TOX2, TOX4, NR4A2, NR4A3.

CAR T Cell Co-Expressing MYD88 and Intracellular Domain of CD40

Figure 31:
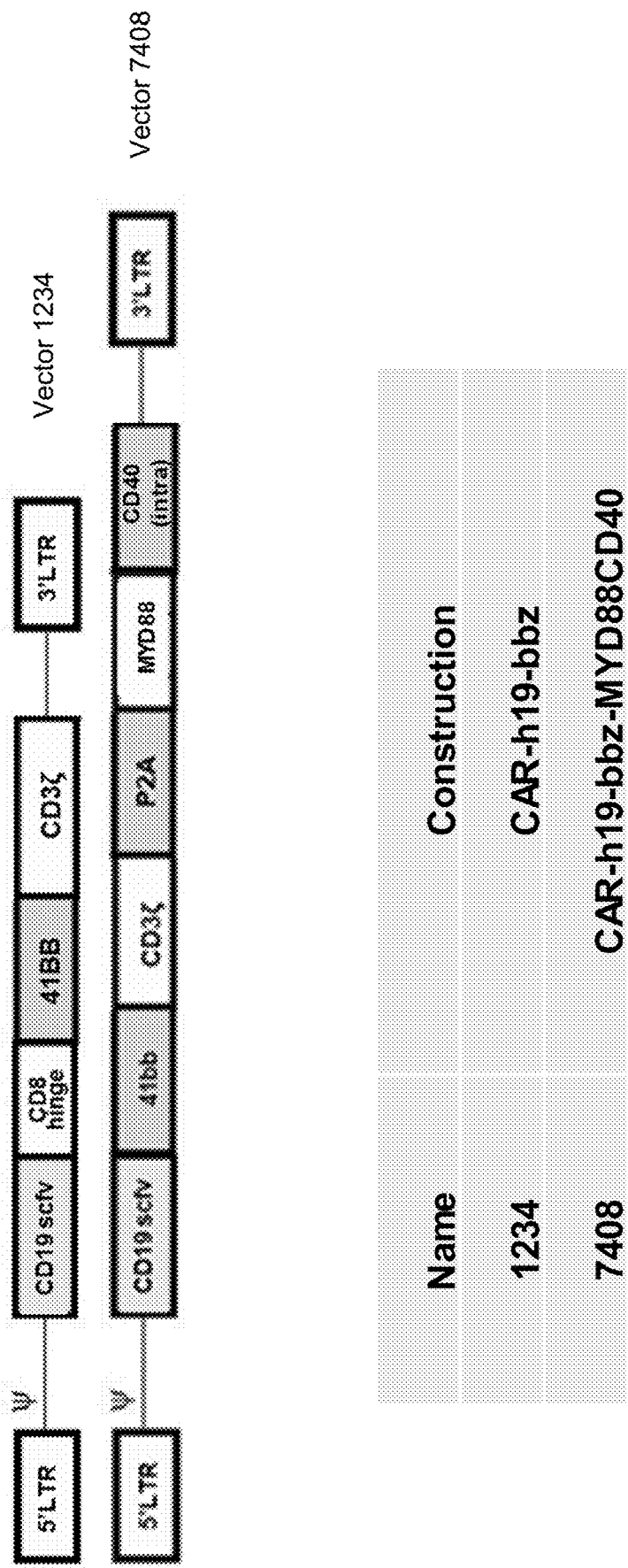
FIG. 31 shows a schematic diagram of vectors.
Figure 32:
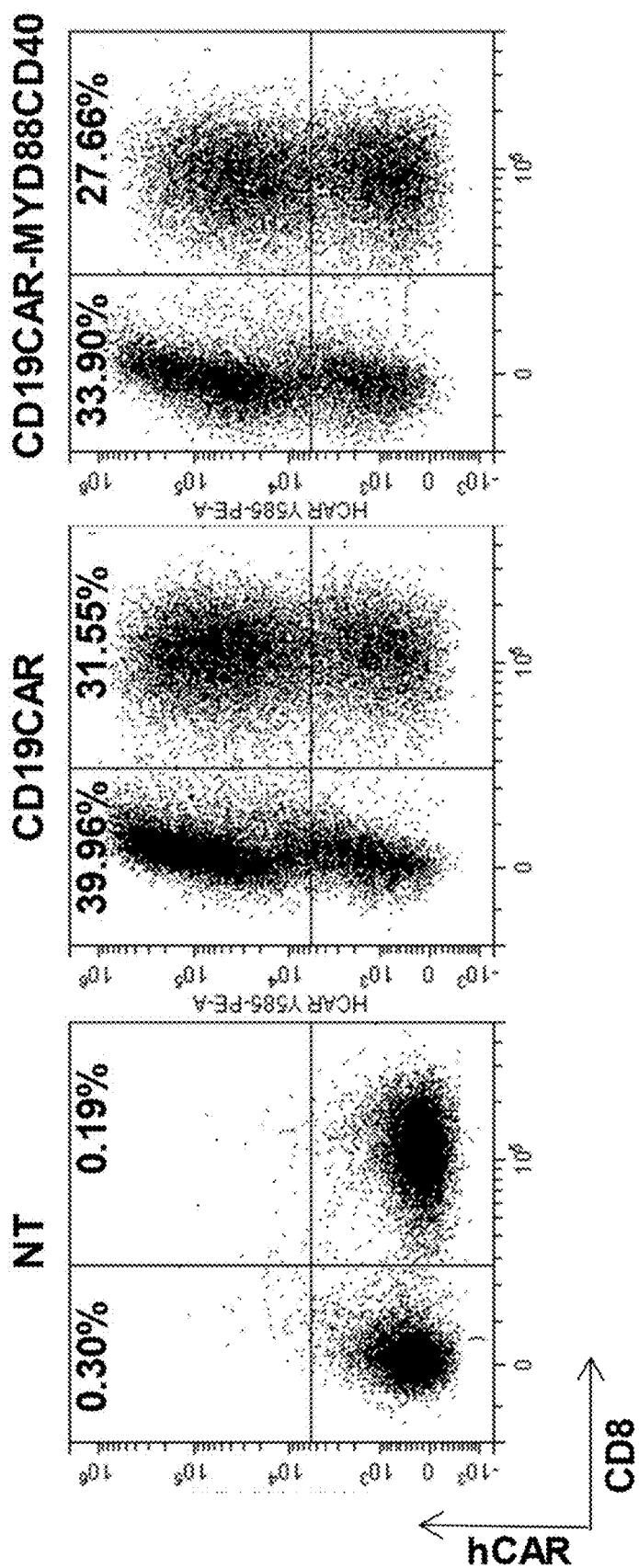
FIG. 32 shows results of flow cytometry analysis of T cells expressing CAR, MYD88, and the intracellular domain of CD40.
Figures 33A, 33B:
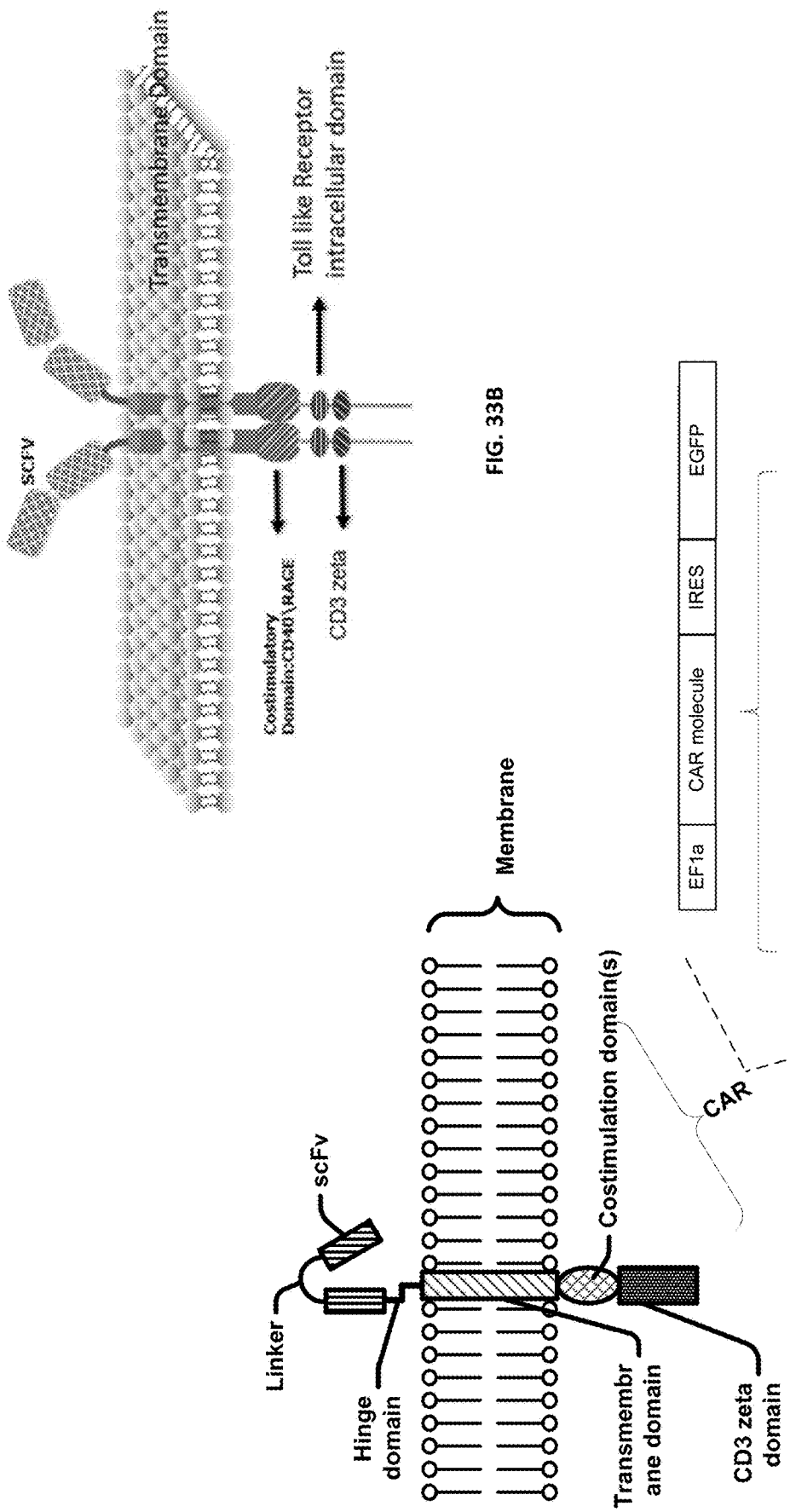
FIGS. 33A and 33B show a schematic diagram of CAR and a portion of a modified cell, and a schematic diagram of CAR-DC.

FIG. 31 shows a schematic diagram of vectors. FIG. 32 shows results of flow cytometry analysis of T cells expressing CAR, MYD88, and the intracellular domain of CD40. On day 0, Peripheral blood was extracted from healthy volunteers. CD3+ T cells were sorted by pan T Kit. 100 ul transAct™ per 1×10$^7$ T cells were added. On day 1, 4×10$^6$ T cells were transfected with a 1234 vector (M01=10). 4×10$^6$ T cells were transfected with 7408 vectors (MOI=34.65). On day 2, cultural media were changed. The lentivirus and TransAct™ were removed, and the cells were resuspended in fresh media (See Table 3). On day 7, flow detection of CAR expression was performed. Since both vectors are humanized antibodies, human CAR antibody detection is performed. The expression ratio of CAR T cells, including vector 1234, is 71.51%. The expression ratio of CART cells, including vector 7408, is 61.56%.

TABLE 3

|      | K562 | K562-CD19 | B cell | E:T | systems |
|------|------|-----------|--------|-----|---------|
| 1234 | −    | −         | −      | 60 × 10$^4$:20 × 10$^4$ | Resuspend in 800 |
|      | +    | −         | −      |     | ul texmacs |
|      | −    | +         | −      |     | medium without |
|      | −    | −         | +      |     | IL2 |
| 7408 | −    | −         | −      |     |  |
|      | +    | −         | −      |     |  |
|      | −    | +         | −      |     |  |
|      | −    | −         | +      |     |  |

CAR T Cell Expressing CAVIN3 or ZBED2

Figure 34A:
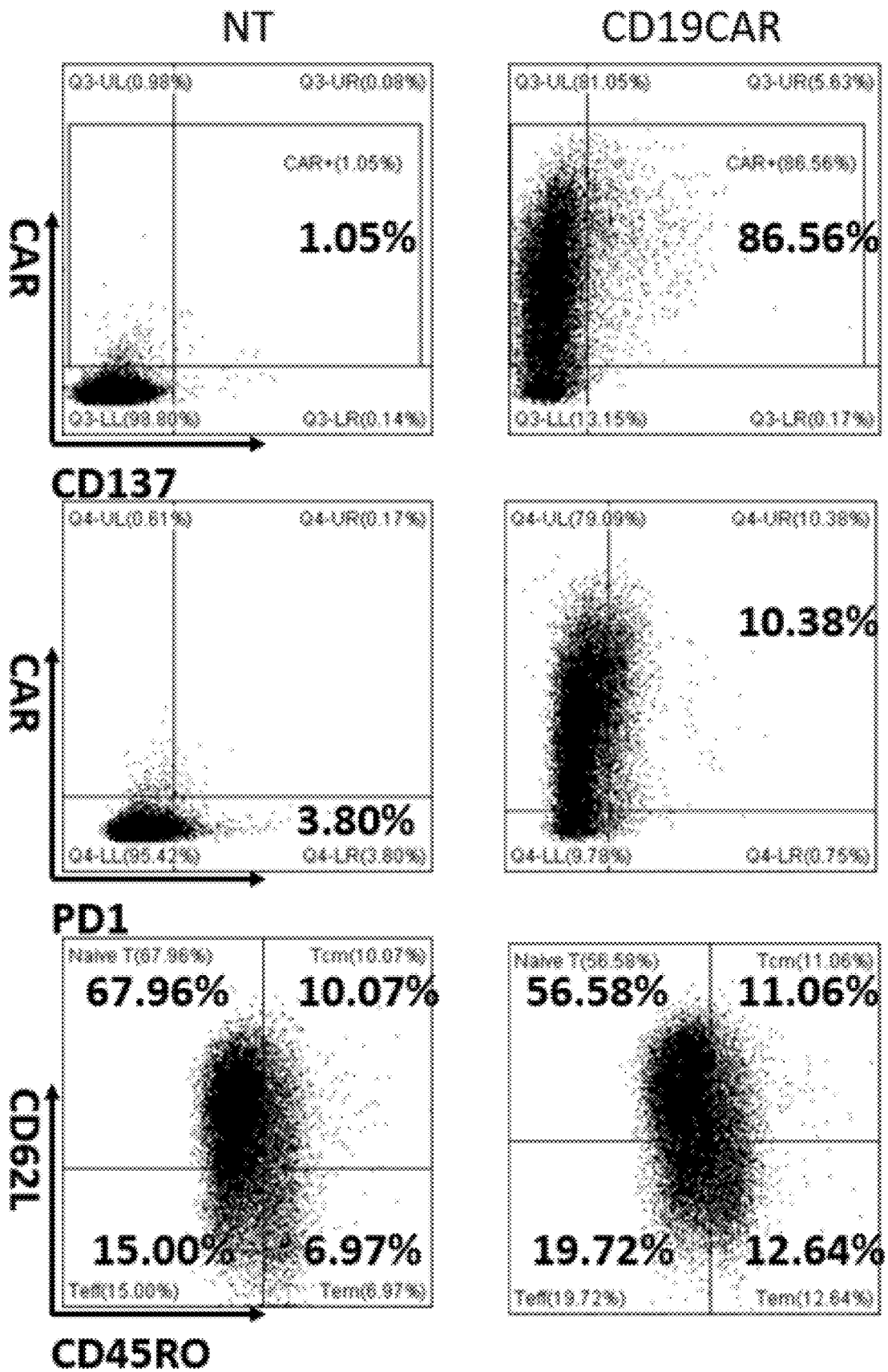
FIGS. 34A and 34B show CAR expression and phenotypes of CAR T cells expressing CAVIN3 or ZBED2.
Figure 34B:
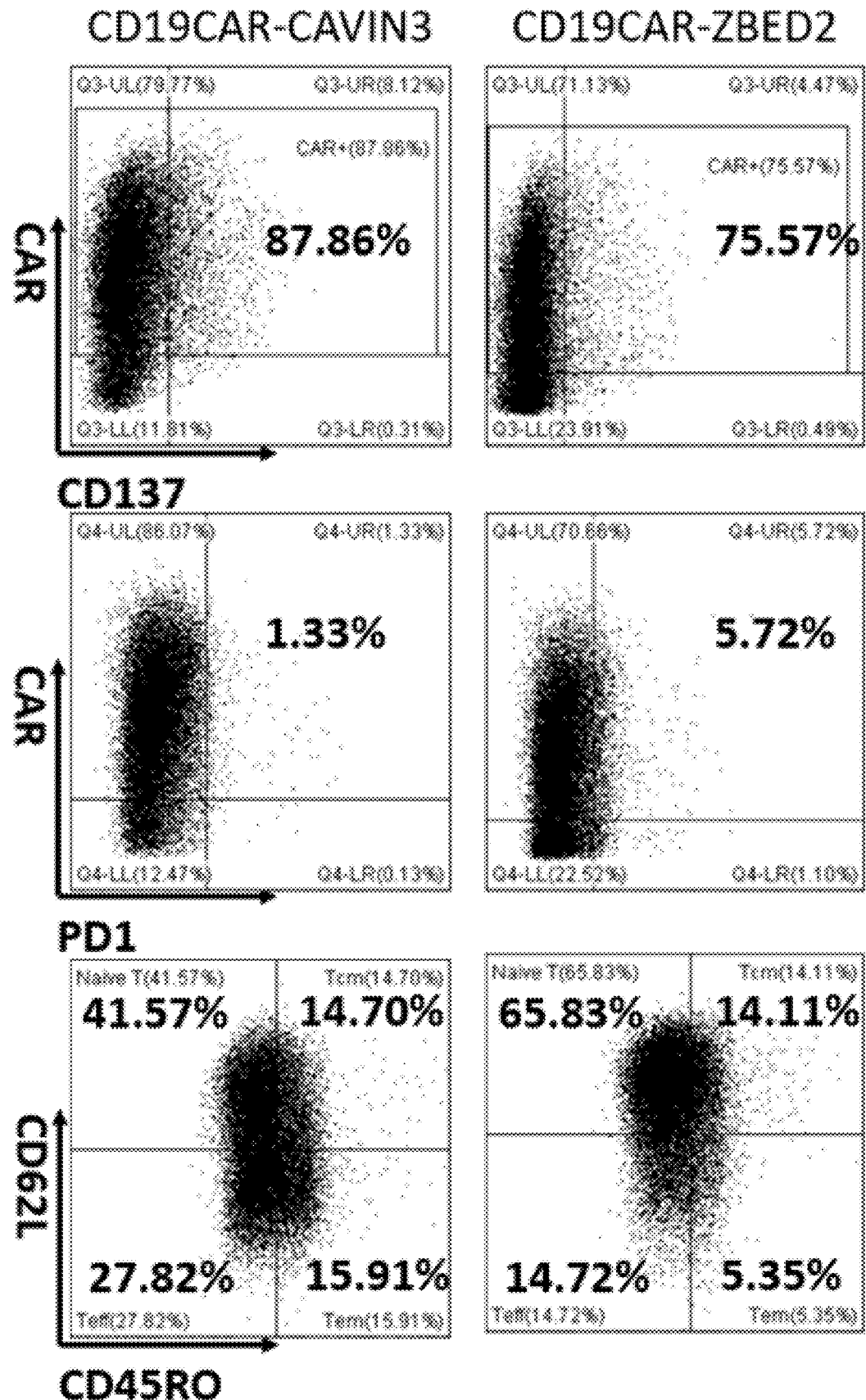

FIGS. 34A and 34B (FIG. 34) show CAR expression and phenotypes of CAR T cells expressing CAVIN3 or ZBED2. T cells were transduced with lentivirus containing vectors CD19 CAR and CAVIN3 or ZBED2, and CAR expression and phenotypes of CAR T cells were analyzed. As shown in FIG. 34, overexpression of CAVIN3 and ZBED2 did not affect the expression of CAR, and the exhaustion levels of CD19 CAR T cells expressing CAVIN3 or ZBED2 were lower than CD19 CAR T cells that did not overexpress CAVIN3 and ZBED2. CAR T cells expressing ZBED2 showed more Naïve and memory-like phenotypes. In sum, CAVIN3 and ZBED2 did not affect the functions of CART cells, and CAVIN3 made CAR T cells differentiate towards effector T cells, while ZBED2 made cells differentiate to memory CAR T cells.

Figure 35:
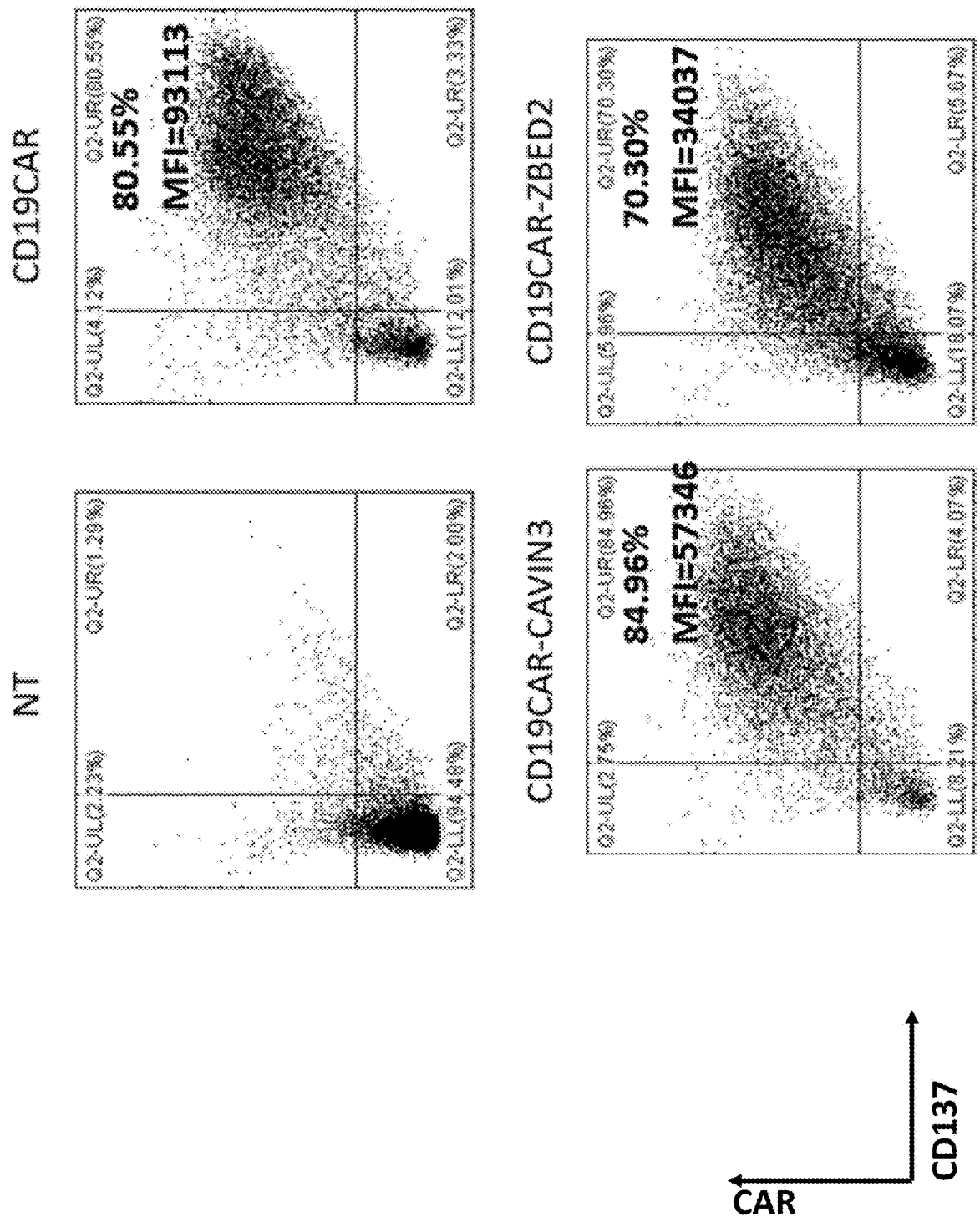
FIG. 35 shows cell activation of CAR T cells expressing CAVIN3 or ZBED2 after co-cultured with substrate cells NALM6.

FIG. 35 shows cell activation of CAR T cells expressing CAVIN3 or ZBED2 after being co-cultured with substrate cells NALM6. NT or CD19 CAR T cells expressing CAVIN3 or ZBED2 were co-cultured with NALM6 cells at a ratio of 1:1. The CAR T cells showed normal activation, and the activation of CD19 CART cells that did not overexpress CAVIN3 and ZBED2 was higher than that of CD19 CART cells expressing CAVIN3 or ZBED2, indicating that expression of CAVIN3 or ZBED2 protected the cells from being over-activated.

Figure 36:
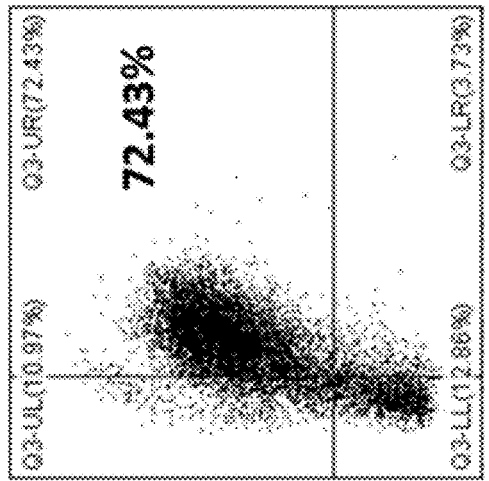
FIG. 36 shows cell exhaustion of CAR T cells expressing CAVIN3 or ZBED2 after co-cultured with substrate cells NALM6.
Figure 36:
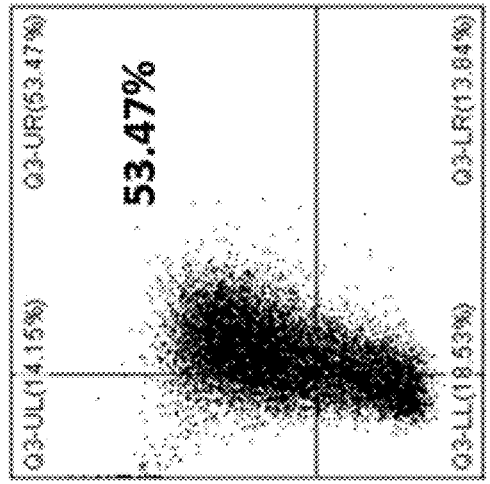
Figure 36:
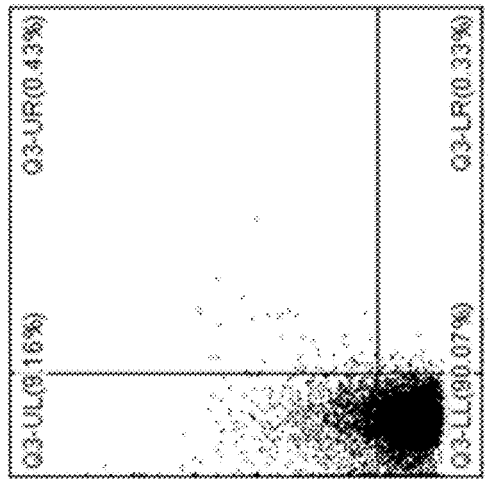
Figure 36:
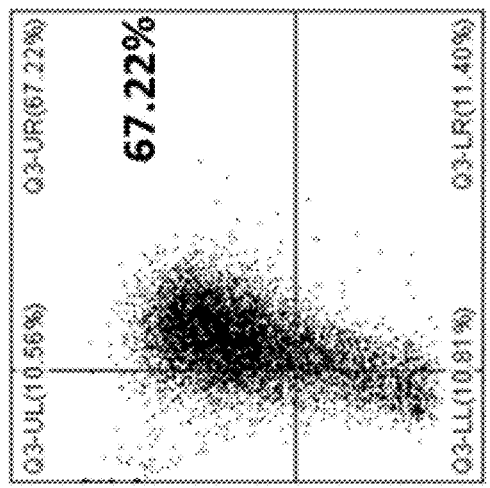

FIG. 36 shows cell exhaustion of CAR T cells expressing CAVIN3 or ZBED2 after being co-cultured with substrate cells NALM6. NT or CD19 CAR T cells expressing CAVIN3 or ZBED2 were co-cultured with NALM6 cells at a ratio of 1:1. As shown in FIG. 36, cell exhaustion levels of CAR T cells expressing CAVIN3 or ZBED2 were lower than that of CAR T cells that did not overexpress CAVIN3 and ZBED2. Thus, the expression of CAVIN3 or ZBED2 helps reduce the exhaustion of CAR T cells, promoting the persistence of CAR T cells.

Figure 37:
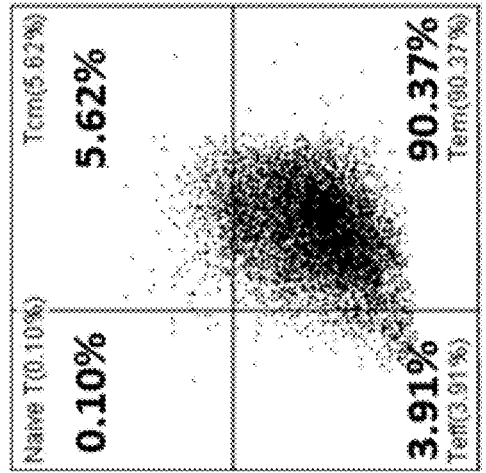
FIG. 37 shows cell phenotype changes of CAR T cells expressing CAVIN3 or ZBED2 after co-cultured with substrate cells NALM6.
Figure 37:
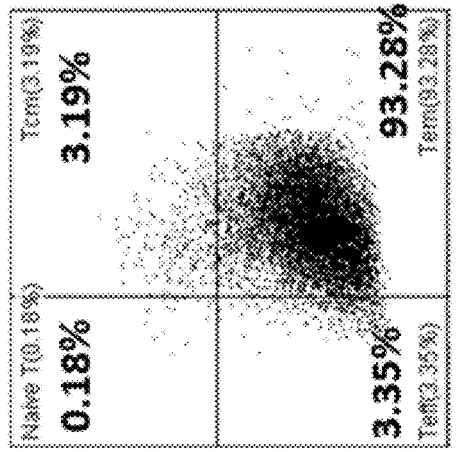
Figure 37:
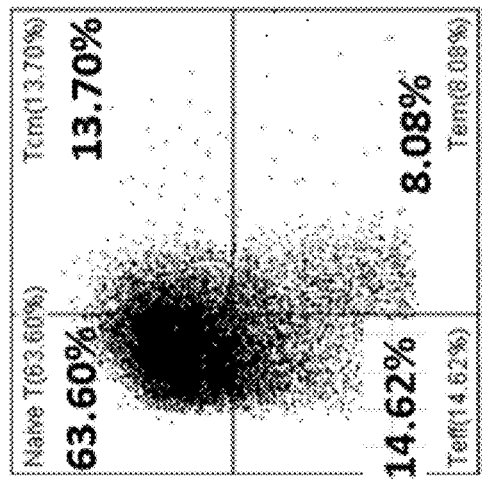
Figure 37:
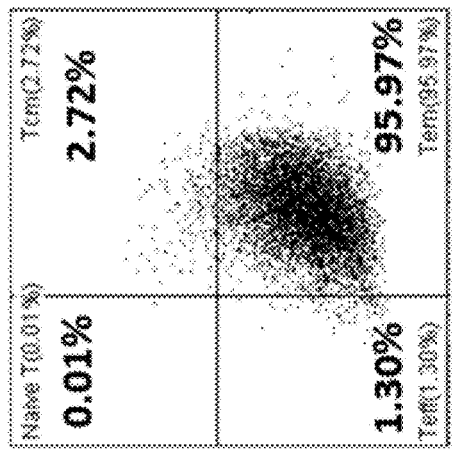

FIG. 37 shows cell phenotype changes of CAR T cells expressing CAVIN3 or ZBED2 after being co-cultured with substrate cells NALM6. NT or CD19 CART cells expressing CAVIN3 or ZBED2 were co-cultured with NALM6 cells at a ratio of 1:1. After co-culturing, while NT or CAR T cells differentiated towards effector cell phenotypes, CAR T cells CAVIN3 or ZBED2 maintained more cell phenotypes (less effector T cells like) than CAR T cells that did not overexpress CAVIN3 and ZBED2.

Figure 38A:
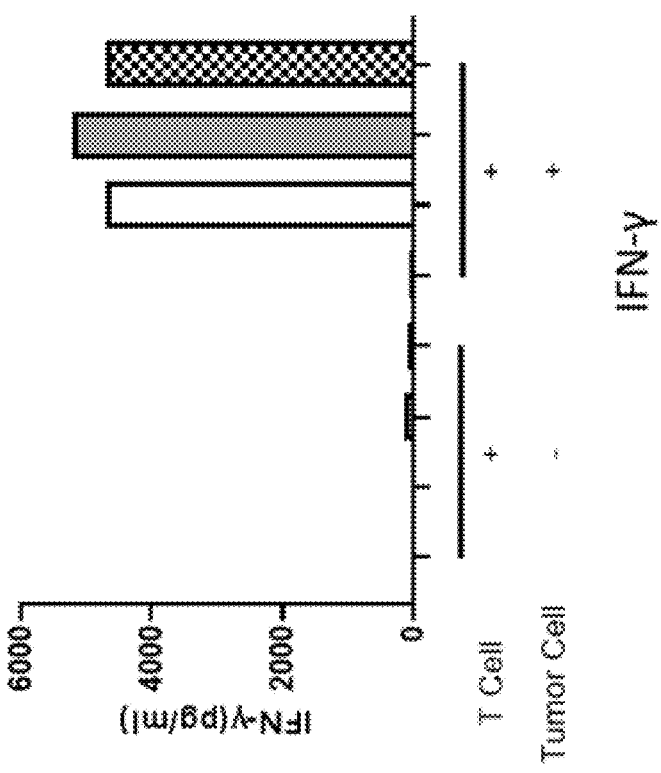
FIGS. 38A, 38B, and 38C show cytokine release of CAR T cells expressing CAVIN3 or ZBED2 after co-cultured with substrate cells NALM6.
Figure 38B:
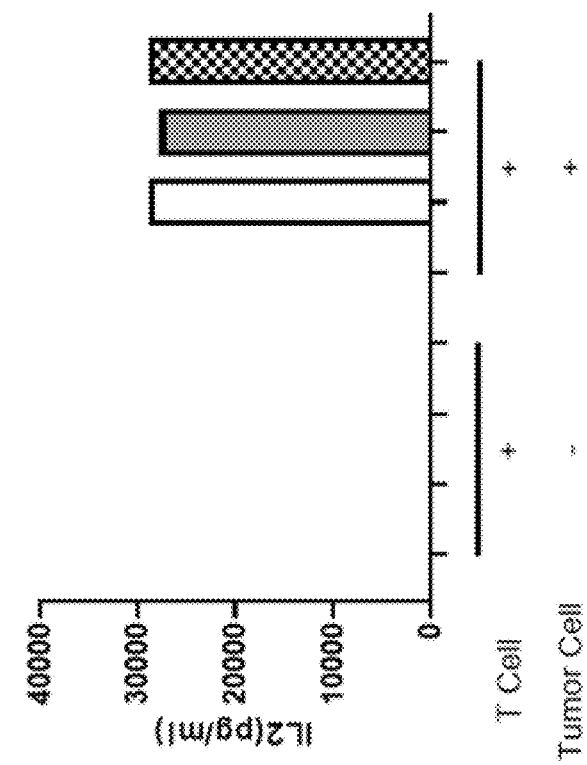
Figure 38C:
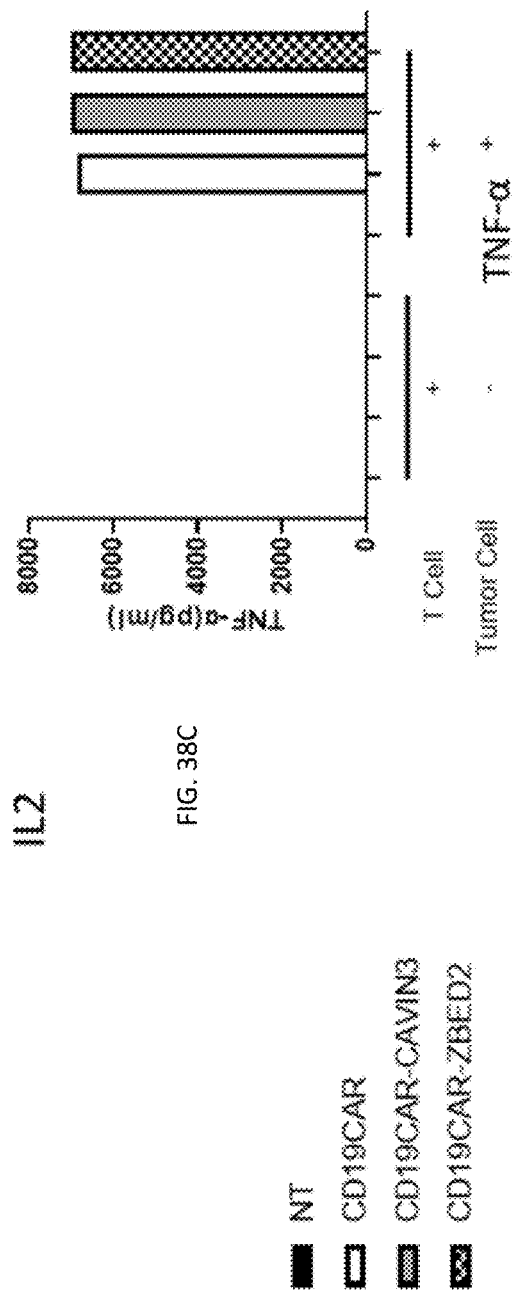

FIG. 38 shows cytokine release of CAR T cells expressing CAVIN3 or ZBED2 after being co-cultured with substrate cells NALM6. NT or CD19 CAR T cells expressing CAVIN3 or ZBED2 were co-cultured with NALM6 cells at a ratio of 1:1. After co-culturing, cytokines released by CAR T cells were measured. As shown in FIG. 38, these three types of CAR T cells showed similar cytokine release levels after being co-cultured with NALM6.

Figure 39:
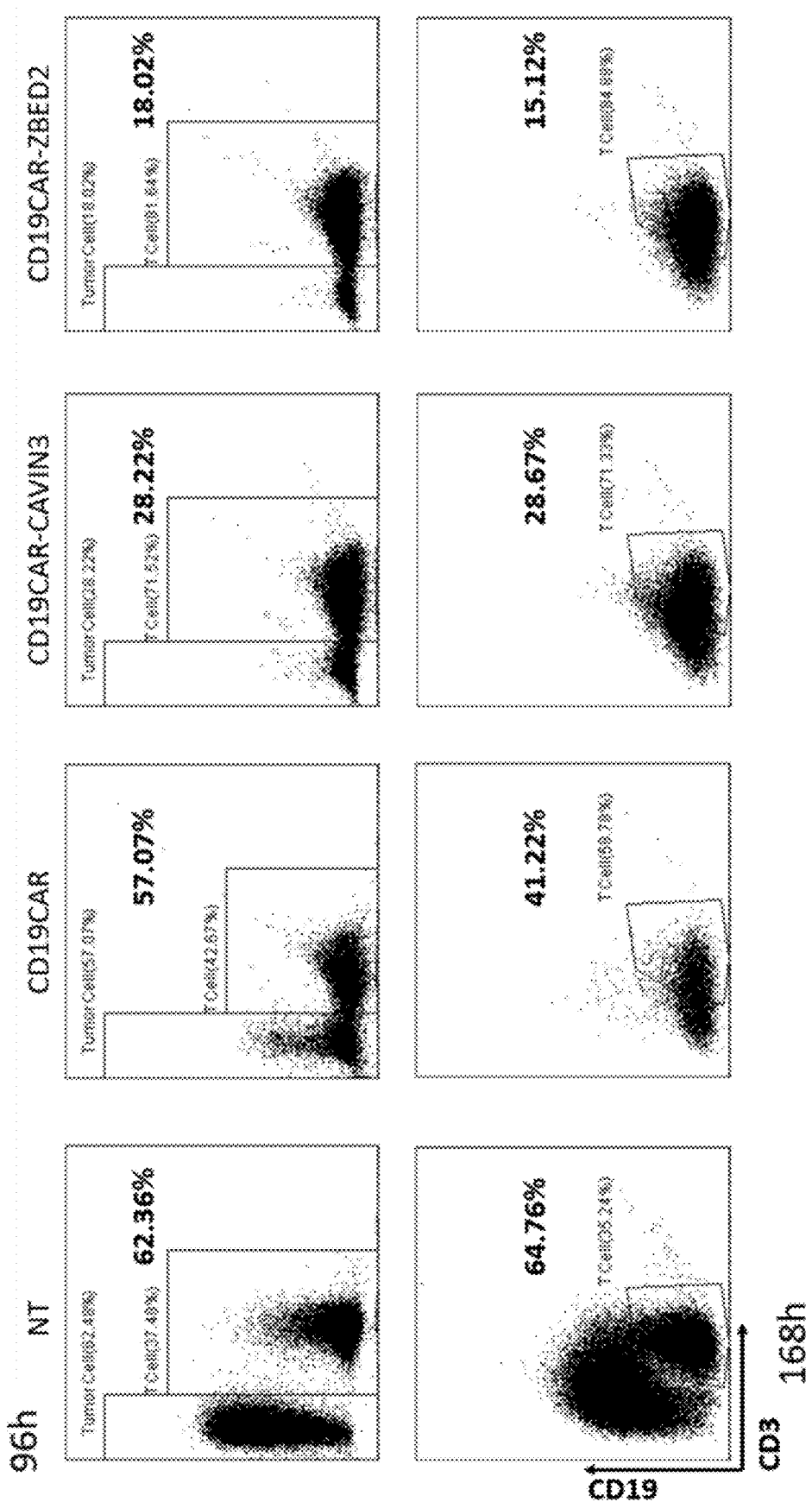
FIG. 39 shows tumor inhibition assay results of CAR T cells expressing CAVIN3 or ZBED2 after co-cultured with substrate cells NALM6.

FIG. 39 shows tumor inhibition assay results of CART cells expressing CAVIN3 or ZBED2 after being co-cultured with substrate cells NALM6. NT or CD19 CART cells expressing CAVIN3 or ZBED2 were co-cultured with NALM6 cells at a ratio of 1:1. After co-culturing for various times, populations of tumor cells (NALM6) were analyzed. As shown in FIG. 39, tumor inhibition levels of CAR T cells CAVIN3 or ZBED2 were higher than that of CAR T cells that did not overexpress CAVIN3 and ZBED2.

Figure 40:
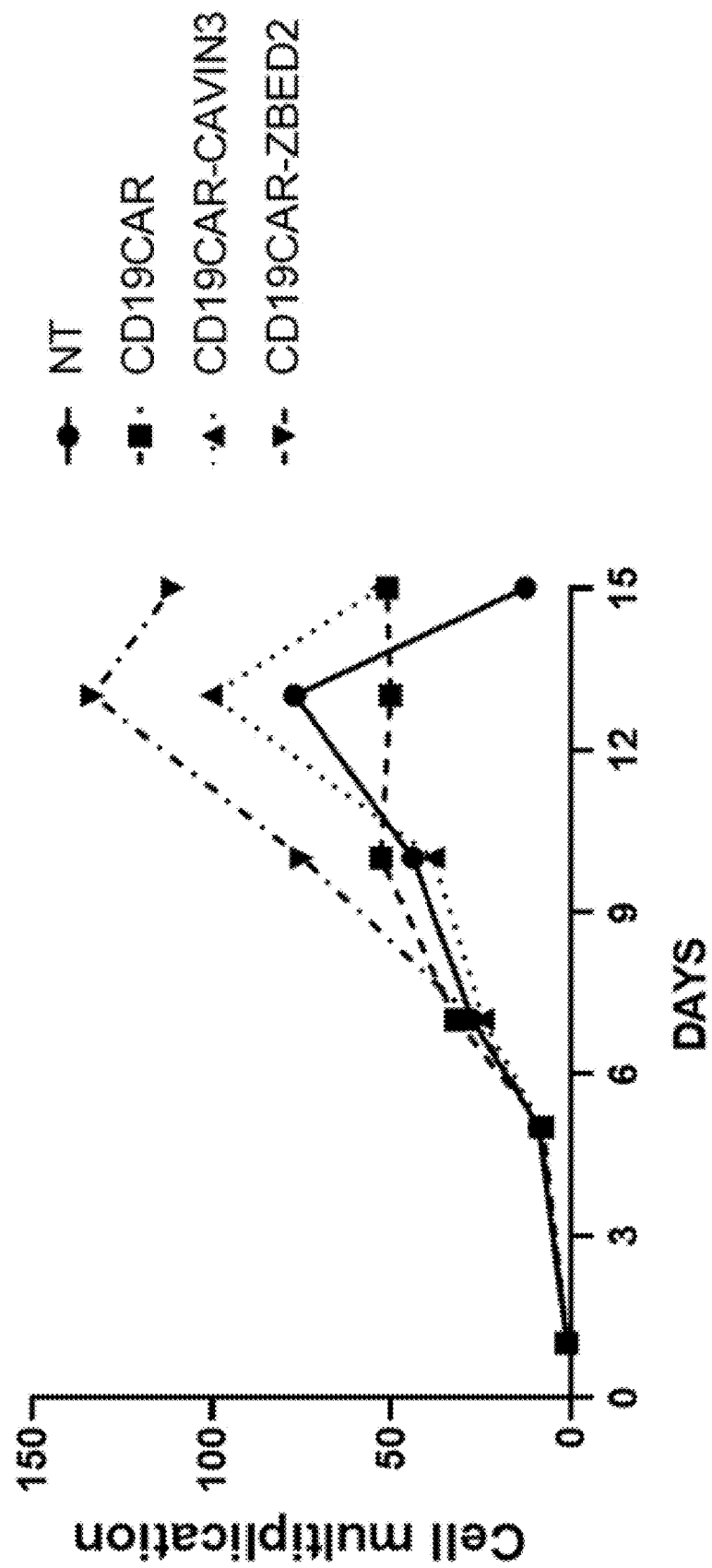
FIG. 40 shows cell expansion of CAR T cells expressing CAVIN3 or ZBED2.

FIG. 40 shows cell expansion of CAR T cells expressing CAVIN3 or ZBED2. NT or CD19 CAR T cells expressing CAVIN3 or ZBED2 were cultured with TEXMACS containing IL2 and counted on days 1, 5, 7, 10, 13, and 15. As shown in FIG. 39, cell expansion levels of CAR T cells CAVIN3 or ZBED2 were higher than that of CAR T cells without overexpressing CAVIN3 and ZBED2.

TABLE 4

| Identifiers | SEQ ID NO: |
| --- | --- |
| CD8b | SEQ ID NO: 1 |
| CD8a | SEQ ID NO: 2 |
| CD40 | SEQ ID NO: 3 |
| CD4 | SEQ ID NO: 4 |
| CD5 | SEQ ID NO: 5 |
| CD3zeta | SEQ ID NO: 6 |
| CD22 | SEQ ID NO: 7 |
| CD28 | SEQ ID NO: 8 |
| CD33 | SEQ ID NO: 9 |
| CD64 | SEQ ID NO: 10 |
| CD80 | SEQ ID NO: 11 |
| CD86 | SEQ ID NO: 12 |
| CD134 | SEQ ID NO: 13 |

TABLE 4-continued

| Identifiers | SEQ ID NO: |
| --- | --- |
| CD137 | SEQ ID NO: 14 |
| CD154 | SEQ ID NO: 15 |
| TLR1 | SEQ ID NO: 16 |
| TLR2 | SEQ ID NO: 17 |
| TLR3 | SEQ ID NO: 18 |
| TLR4 | SEQ ID NO: 19 |
| TLR5 | SEQ ID NO: 20 |
| TLR6 | SEQ ID NO: 21 |
| TLR7 | SEQ ID NO: 22 |
| TLR8 | SEQ ID NO: 23 |
| TLR9 | SEQ ID NO: 24 |
| TLR10 | SEQ ID NO: 25 |
| MYD88 | SEQ ID NO: 26 |
| TRIF | SEQ ID NO: 27 |
| TRAM | SEQ ID NO: 28 |
| TIRAP | SEQ ID NO: 29 |
| Linker | SEQ ID NO: 30 |
| Cavin3 | SEQ ID NO: 31 |
| ZBED2 | SEQ ID NO: 32 |
| MYC | SEQ ID NO: 33 |
| STAT1wt | SEQ ID NO: 34 |
| STAT1 D165G | SEQ ID NO: 35 |
| STAT1 N179K | SEQ ID NO: 36 |
| STAT1 R274Q | SEQ ID NO: 37 |
| STAT1 R274W | SEQ ID NO: 38 |
| STAT1 K278E | SEQ ID NO: 39 |
| STAT1 Q285R | SEQ ID NO: 40 |
| STAT1 K298N | SEQ ID NO: 41 |
| STAT1 G384D | SEQ ID NO: 42 |
| STAT1 T385M | SEQ ID NO: 43 |
| STAT3 wt | SEQ ID NO: 44 |
| STAT3 N647I | SEQ ID NO: 45 |
| STAT3 G421R | SEQ ID NO: 46 |
| STAT3 Q344H | SEQ ID NO: 47 |
| STAT3 E415K | SEQ ID NO: 48 |
| STAT3 R152W | SEQ ID NO: 49 |
| STAT3 T716M | SEQ ID NO: 50 |
| STAT3 N420K | SEQ ID NO: 51 |
| STAT3 V353F | SEQ ID NO: 52 |
| STAT4 wt | SEQ ID NO: 53 |
| STAT4 Y693D | SEQ ID NO: 54 |
| STAT4 S721D | SEQ ID NO: 55 |

All publications, patents, and patent applications cited in this specification are incorporated herein by reference in their entireties as if each individual publication, patent, or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A method of enhancing an anti-tumor effect of a lymphocyte, the method comprising:
introducing an exogenous polynucleotide encoding Caveolae Associated Protein 3 (CAVIN3) or Zinc finger bed-type containing 2 (ZBED2) into lymphocytes to obtain modified lymphocytes;
contacting the modified lymphocytes with tumor cells that the modified lymphocytes bind; and
allowing the modified lymphocytes to generate an anti-tumor effect, wherein the anti-tumor effect of the modified lymphocytes is enhanced as compared to lymphocytes that do not express an exogenous CAVIN3 and ZBED2.

2. The method of claim 1, wherein the lymphocytes are T cells or NK cells.

3. The method of claim 2, wherein the anti-tumor effect comprises at least one of reduced cell exhaustion, enhanced cell expansion, and enhanced tumor growth inhibition.

4. The method of claim 3, wherein the cell exhaustion level of the modified lymphocytes is lower than that of lymphocytes that do not express an exogenous CAVIN3 or ZBED2, the cell expansion level of the modified lymphocytes is higher than that of lymphocytes that do not express an exogenous CAVIN3 or ZBED2, and/or the tumor growth inhibition of the modified lymphocytes is greater than that of lymphocytes that do not express an exogenous CAVIN3 or ZBED2.

5. The method of claim 1, wherein the exogenous polynucleotide encodes amino acid SEQ ID NO: 31.

6. The method of claim 1, wherein the exogenous polynucleotide encodes amino acid SEQ ID NO: 32.

7. The method of claim 1, wherein the lymphocytes comprises an antigen binding molecule.

8. The method of claim 7, wherein the antigen binding molecule is a chimeric antigen receptor (CAR) comprising an antigen-binding domain, a transmembrane domain, and an intracellular signaling domain.

9. The method of claim 8, wherein the antigen-binding domain binds a tumor antigen comprising TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRCSD, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LACE-1a, legumain, HPV E6, E7, MAGE A1, ETV6-AML, sperm protein 17, XAGE1, Tie 2, MAD-CT-1, MAD-CT-2, Fos-related antigen 1 (Fra 1 or FosL1), p53, p53 mutant, prostein, survivin, telomerase, PCTA-1/Galectin 8, MelanA/MART1, Ras mutant, hTERT, sarcoma translocation breakpoints, ML-IAP, ERG, NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1.

10. The method of claim 8, wherein the intracellular signaling domain comprises a co-stimulatory signaling domain, or a primary signaling domain and a co-stimulatory signaling domain, and wherein the co-stimulatory signaling domain comprises a functional signaling domain of a protein comprising CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

11. The method of claim 7, wherein the antigen binding molecule is a modified T cell receptor (TCR) or tumor infiltrating lymphocyte (TIL).

12. The method of claim 11, wherein the TCR is obtained from spontaneously occurring tumor-specific T cells in subjects.

13. The method of claim 11, wherein the TCR binds a tumor antigen.

14. The method of claim 13, wherein the tumor antigen comprises CEA, gp100, MART-1, p53, MAGE-A3, or NY-ESO-1.

15. The method of claim 11, wherein the TCR comprises TCRγ and TCRδ chains, TCRα and TCRβ chains, or a combination thereof.

16. The method of claim 1, wherein the lymphocytes comprise a nucleic acid encoding a dominant negative form of an inhibitory immune checkpoint molecule or a receptor thereof, and wherein the inhibitory immune checkpoint molecule comprises programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRD, natural killer cell receptor 2B4 (2B4), or CD 160.

17. The method of claim 1, wherein the lymphocytes comprise a nucleic acid encoding human telomerase reverse transcriptase (hTERT), a nucleic acid encoding SV40 large T antigen (SV40LT), or a combination thereof.

18. The method of claim 1, wherein the lymphocytes comprise a nucleic acid encoding a cytokine.

19. The method of claim 18, wherein the cytokine comprises IL-6, IL-7, IL-15, IL-12, or IFNγ.

20. The method of claim 1, wherein the lymphocytes comprise a first population of T cells comprising a CAR binding a cell surface molecule of a white blood cell (WBC) and a second population of T cells comprising a CAR binding a solid tumor antigen.

* * * * *